(12) United States Patent
Miller, Jr. et al.

(10) Patent No.: US 7,217,537 B2
(45) Date of Patent: May 15, 2007

(54) METHOD TO INCREASE CAROTENOID PRODUCTION IN A MICROBIAL HOST CELL BY DOWN-REGULATING GLYCOGEN SYNTHASE

(75) Inventors: Edward S. Miller, Jr., Wilmington, DE (US); James M. Odom, Kennett Square, PA (US); Pamela L. Sharpe, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/227,613

(22) Filed: Sep. 15, 2005

(65) Prior Publication Data

US 2007/0059790 A1 Mar. 15, 2007

(51) Int. Cl.
- C12P 1/00 (2006.01)
- C12P 23/00 (2006.01)
- C12P 31/00 (2006.01)
- C12N 15/70 (2006.01)

(52) U.S. Cl. .......................... 435/41; 435/67; 435/471; 435/63

(58) Field of Classification Search .................. 435/41, 435/67, 471, 63; 536/23.2
See application file for complete search history.

(56) References Cited

U.S. PATENT DOCUMENTS

| | | | |
|---|---|---|---|
| 5,182,208 A | 1/1993 | Johnson et al. | |
| 5,429,939 A | 7/1995 | Misawa et al. | |
| 5,466,599 A | 11/1995 | Jacobson et al. | |
| 5,530,188 A | 6/1996 | Ausich et al. | |
| 5,530,189 A | 6/1996 | Ausich et al. | |
| 5,545,816 A | 8/1996 | Ausich et al. | |
| 5,656,472 A | 8/1997 | Ausich et al. | |
| 5,691,190 A | 11/1997 | Girard et al. | |
| 5,935,808 A | 8/1999 | Hirschberg et al. | |
| 5,972,642 A | 10/1999 | Fleno et al. | |
| 6,015,684 A | 1/2000 | Jacobson et al. | |
| 6,124,113 A | 9/2000 | Hohmann et al. | |
| 6,825,002 B2 | 11/2004 | Tsubokura et al. | |
| 2004/0078846 A1 | 4/2004 | Desouza et al. | |

OTHER PUBLICATIONS

Gallagher et al Surrogate biochemistry: use of *Escherichia coli* to identify plant cDNAs that impact metabolic engineering of carotenoid accumulation. (2003) Applied Microbiology and Biotechnology 60:713-719.*

DellaPenna et al, Plant Metabolic Engineering Plant Physiology, Jan. 2001, vol. 125, pp. 160-163.*

U.S. Appl. No. 09/941,947, filed Aug. 29, 2001, Patricia C. Brzostowicz et al.

U.S. Appl. No. 10/997,308, filed Nov. 24, 2004, Pamela L. Sharpe.

U.S. Appl. No. 10/997,844, filed Nov. 24, 2004, Pamela L. Sharpe et al.

U.S. Appl. No. 11/015,433, filed Dec. 17, 2004, Qiong Cheng et al.

U.S. Appl. No. 60/577,970, filed Jun. 8, 2004, Qiong Cheng et al.

U.S. Appl. No. 60/601,947, filed Aug. 16, 2004, Qiong Cheng et al.

G. Armstrong, Carotenoid Genetics and Biochemistry, Comprehensive Natural Products Chemistry, 1999, pp. 321-352, vol. 2.

P. C. Lee et. al., Metabolic Engineering Towards Biotechnological Production of Carotenoids in Microorganisms, Appl. Microbiol. Biotechnol., 2002, pp. 1-11, vol. 60.

Pyung Cheon Lee et. al., Biosynthesis of Structurally Novel Carotenoids in *Escherichia coli*. Chem. Biol., 2003, pp. 453-462, vol. 10.

Paul D. Fraser et. al., The Biosynthesis and Nutritional Uses of Carotenoids, Progress in Lipid Research, 2004, pp. 228-265, vol. 43.

W.R. Farmer et. al., Precursor Balancing for Metabolic Engineering of Lycopene Production in *Escherichia coli*, Biotechnol. Prog., 2001, pp. 57-61, vol. 17.

C. Wang et. al., Directed Evolution of Metabolically Engineered *Escherichia coli* for Carotenoid Production, Biotechnol. Prog., 2000, pp. 922-926, vol. 16.

N. Misawa et. al., Metabolic Engineering for the Production of Carotenoids in Non-Carotenogenic Bacteria and Yeasts, J. Biotechnol., 1998, pp. 169-181, vol. 59.

H. Shimada et. al., Increased Carotenoid Production by the Food Yeast *Candida Utilis* Through Metabolic Engineering of the Isoprenoid Pathway, Appl. Environ. Microbiol., 1998, pp. 2676-2680, vol. 64.

M. Albrecht et. al., Metabolic Engineering of the Terpenoid Biosynthetic Pathway of *Escherichia coli* for Production of the Carotenoids B-Parotene and Zeaxanthin, Biotechnol. Lett., 1999, pp. 791-795, vol. 21.

Y. Miura et. al., Production of the Carotenoids Lycopene, Beta-Carotene, and Astaxanthin in the Food Yeast *Candida Utilis*, Appl. Environ. Microbiol., 1998, pp. 1226-1229, vol. 64.

* cited by examiner

*Primary Examiner*—Kathleen M. Kerr
*Assistant Examiner*—Kagnew Gebreyesus

(57) ABSTRACT

A method to increase carotenoid production in carotenogenic microbial host cells is provided by down-regulating or disrupting glycogen synthesis. Disruption of glycogen synthase activity in a carotenogenic microbial host cell significantly increased carotenoid production. Carotenogenic microorganisms are also provided that have been optimized for the production of carotenoid compounds through the down-regulation and/or disruption of glycogen synthase activity.

19 Claims, 3 Drawing Sheets

Figure 1:
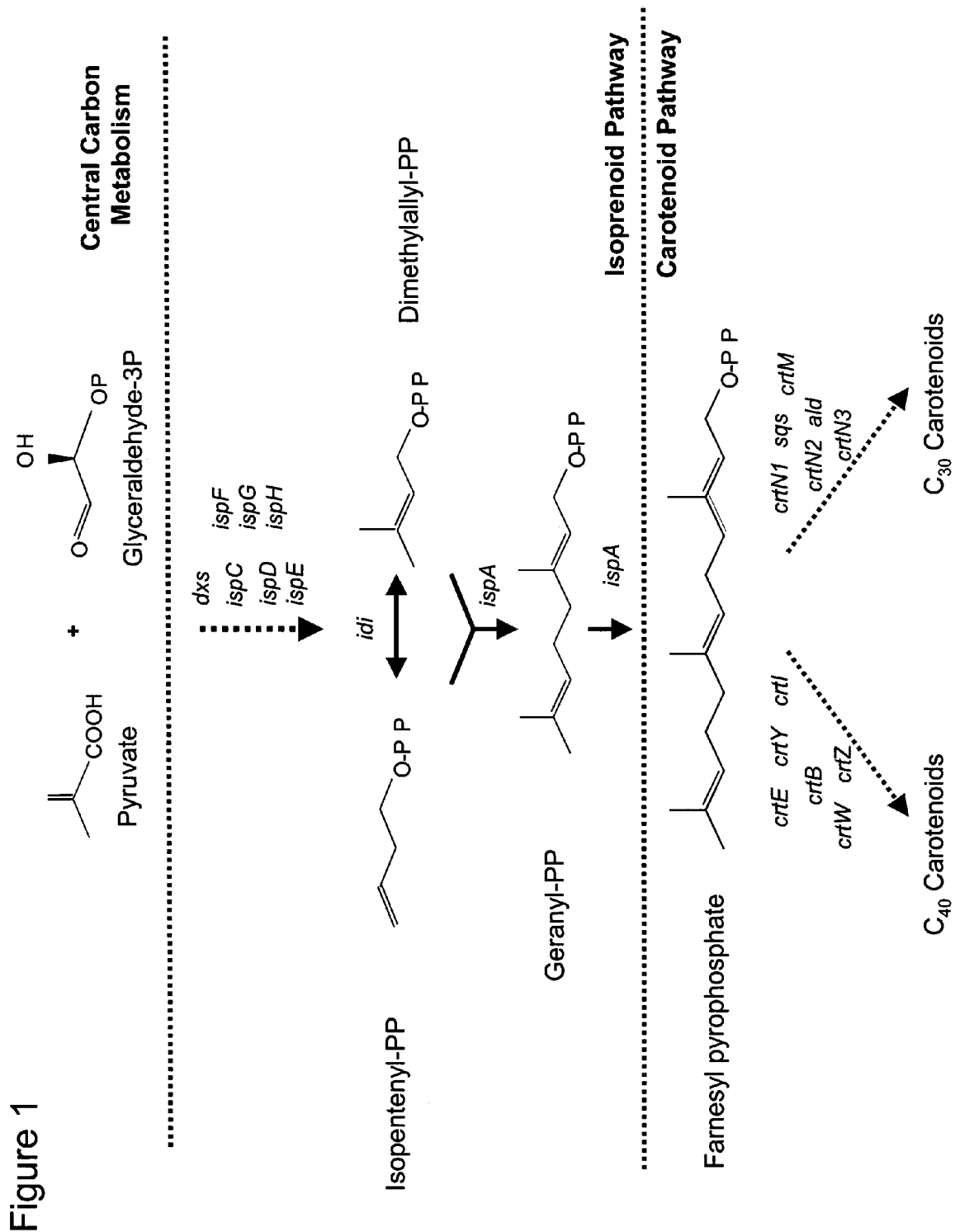

METHOD TO INCREASE CAROTENOID PRODUCTION IN A MICROBIAL HOST CELL BY DOWN-REGULATING GLYCOGEN SYNTHASE

FIELD OF THE INVENTION

The invention relates to the field of microbiology and molecular biology. More specifically, the invention relates to a methods for increasing carotenoid production in carotenogenic microorganisms by down regulating, disrupting or deleting the glycogen synthase gene (glgA).

BACKGROUND OF THE INVENTION

Carotenoids are pigments that are ubiquitous throughout nature and synthesized by all photosynthetic organisms, and in some heterotrophic bacteria and fungi. Carotenoids provide color for flowers, vegetables, insects, fish and birds. Colors of carotenoid range from yellow to red with variations of brown and purple. As precursors of vitamin A, carotenoids are fundamental components in the human diet and play an important role in human health. Animals are unable to synthesize carotenoids de novo and must obtain them by dietary means. Manipulation of carotenoid composition and production in plants or bacteria can provide new and/or improved sources of carotenoids. Industrial uses of carotenoids include, among others, pharmaceuticals, food supplements, animal feed additives, and colorants in cosmetics.

The genetics of carotenoid biosynthesis are well known (Armstrong, G., in *Comprehensive Natural Products Chemistry*, Elsevier Press, volume 2, pp 321–352 (1999)); Lee, P. and Schmidt-Dannert, C., *Appl Microbiol Biotechnol*, 60:1–11 (2002); Lee et al., *Chem Biol* 10:453–462 (2003), and Fraser, P. and Bramley, P., *Progress in Lipid Research*, 43:228–265 (2004)). This pathway is extremely well studied in the Gram-negative, pigmented bacteria of the genera *Pantoea*, formerly known as *Erwinia*. Of particular interest are the genes responsible for the production of $C_{40}$ carotenoids used as pigments in animal feed (e.g. canthaxanthin and astaxanthin).

The genes responsible for biosynthesis of $C_{40}$ carotenoids generally can be divided into two categories: 1) the $C_{40}$ carotenoid backbone biosynthesis genes responsible for the elongation, desaturation, and cyclization steps necessary for the synthesis of β-carotene (i.e. crtE, crtB, crtI, and crtY) and 2) subsequent backbone modification genes encoding enzymes involved in ketolation, hydroxylation, and glucosylation (i.e. crtW, crtO, crtZ, crtX, etc.).

A variety of methods for carotenoid production based on microbial platforms have been described in the art. Organisms such as *Escherichia coli, Candida utilis, Haematococcus pluvialis, Rhodobacter sphaeroides, Paracoccus* sp., and *Phaffia rhodozyma* have been used to produce a variety of carotenoids including, but not limited to lycopene, β-carotene, zeaxanthin, canthaxanthin, and astaxanthin (Farmer, W. R. and J. C. Liao., *Biotechnol. Prog.*, 17: 57–61 (2001); Wang, C. et al., *Biotechnol. Prog.*, 16: 922–926 (2000); Misawa, N. and H. Shimada., *J. Biotechnol.*, 59:169–181 (1998); Shimada, H. et al., *Appl. Environ. Microbiol.*, 64:2676–2680 (1998)); Albrecht, M. et al., *Biotechnol. Lett.*, 21: 791–795 (1999); Miura, Y. et al., *Appl. Environ. Microbiol.*, 64:1226–1229 (1998); U.S. Pat. Nos. 5,691,190; 5,466,599; 6,015,684; 5,182,208; 5,972,642; 5,656,472; 5,545,816; 5,530,189; 5,530,188; 5,429,939; 6,825,002; 5,935,808; US2004/0078846; and U.S. Pat. No. 6,124,113).

Odom et al. have demonstrated that the C1 metabolizing bacterium *Methylomonas* sp. 16a can be engineered for recombinant production of various $C_{40}$ carotenoids (U.S. Ser. No. 09/941,947). The native $C_{30}$ carotenoid biosynthetic pathway in this methylotrophic bacteria has been disrupted, creating a series of strains optimized for $C_{40}$ carotenoid production (U.S. Ser. Nos. 10/997,844 and 10/997,308; hereby incorporated by reference). One of the optimized host strains, *Methylomonas* sp. 16a MWM1200, has been used to recombinantly produce a variety of $C_{40}$ carotenoids (U.S. 60/601,947; U.S. Ser. No. 11/015,433; and U.S. 60/577,970).

Methods to increase carotenoid production in carotenogenic microbial host cells are needed to improve the economics of commercial fermentative production. One possible way to increase carotenoid production in a microbial host cell is to down-regulate and/or disrupt genes encoding enzymes involved in metabolic pathways that may compete for substrates, intermediates, and/or co-factors that influence carotenoid production.

The problem to be solved is to provide a method to increase carotenoid production in a microbial host cell by down-regulating and/or disrupting expression of one or more genes encoding enzymes involved in metabolic pathways that compete for substrates, intermediates, and/or co-factors that influence carotenoid production.

SUMMARY OF THE INVENTION

The problem has been solved by identifying the glycogen synthase gene (glgA) as a target for gene down-regulation/disruption. Disruption of endogenous glycogen synthase activity (E.C. 2.4.1.21) in several unrelated carotenogenic microorganisms increased carotenoid production. More specifically, a deletion in the glgA gene in a carotenogenic microbial host cell engineered to recombinantly produce at least one carotenoid compound (*Methylomonas* sp. and *Escherichia coli*) resulted in viable mutant cells characterized by a significant increase in carotenoid production.

Accordingly, in one aspect the invention provides a method for the production of carotenoid compounds comprising:
  a) providing a carotenogenic microbial host cell, having a gene encoding a glycogen synthase polypeptide comprising;
    i) a carotenoid biosynthetic pathway comprising carotenoid biosynthetic pathway genes; and
    ii) a disruption in the glycogen synthase gene;
  b) growing the host cell of (a) under conditions whereby at least one carotenoid compound is produced; and
  c) optionally isolating the carotenoid compound produced at step (b).

In another aspect the invention provides, a carotenogenic microbial host cell producing at least one carotenoid compound and comprising a disruption in a native glycogen synthase gene.

In another embodiment the invention provides a method of optimizing carotenoid production by a carotenogenic microbial host comprising:
  a) providing a first carotenogenic microbial host cell comprising:
    i) a carotenoid biosynthetic pathway; and
    ii) a gene encoding a glycogen synthase polypeptide;
  wherein said carotenogenic microbial host produces at least one carotenoid compound;

b) disrupting the gene encoding a glycogen synthase polypeptide to create a second, mutant carotenogenic microbial host cell;

c) growing said second mutant carotenogenic microbial host cell under conditions whereby at least one carotenoid compound is produced, wherein carotenoid production of said second mutant host is optimized.

In an alternate embodiment the invention provides a method of producing a high flux carotenogenic microbial host cell comprising:

a) providing a first carotenogenic microbial host cell comprising;
  i) a carotenoid biosynthetic pathway; and
  ii) a gene encoding a glycogen synthase polypeptide;
wherein said carotenogenic microbial host cell produces at least one carotenoid compound; and b) disrupting the gene encoding a glycogen synthase polypeptide in the host cell of step (a) whereby a high flux carotenoid microbial host cell is produced.

BRIEF DESCRIPTION OF THE FIGURES, SEQUENCE DESCRIPTIONS, AND BIOLOGICAL DEPOSITS

FIG. 1 shows the upper carotenoid and lower carotenoid biosynthetic pathways where pyruvate and glyceraldehyde-3-phosphate are converted to a variety of $C_{30}$ and $C_{40}$ carotenoids.

Figure 2:
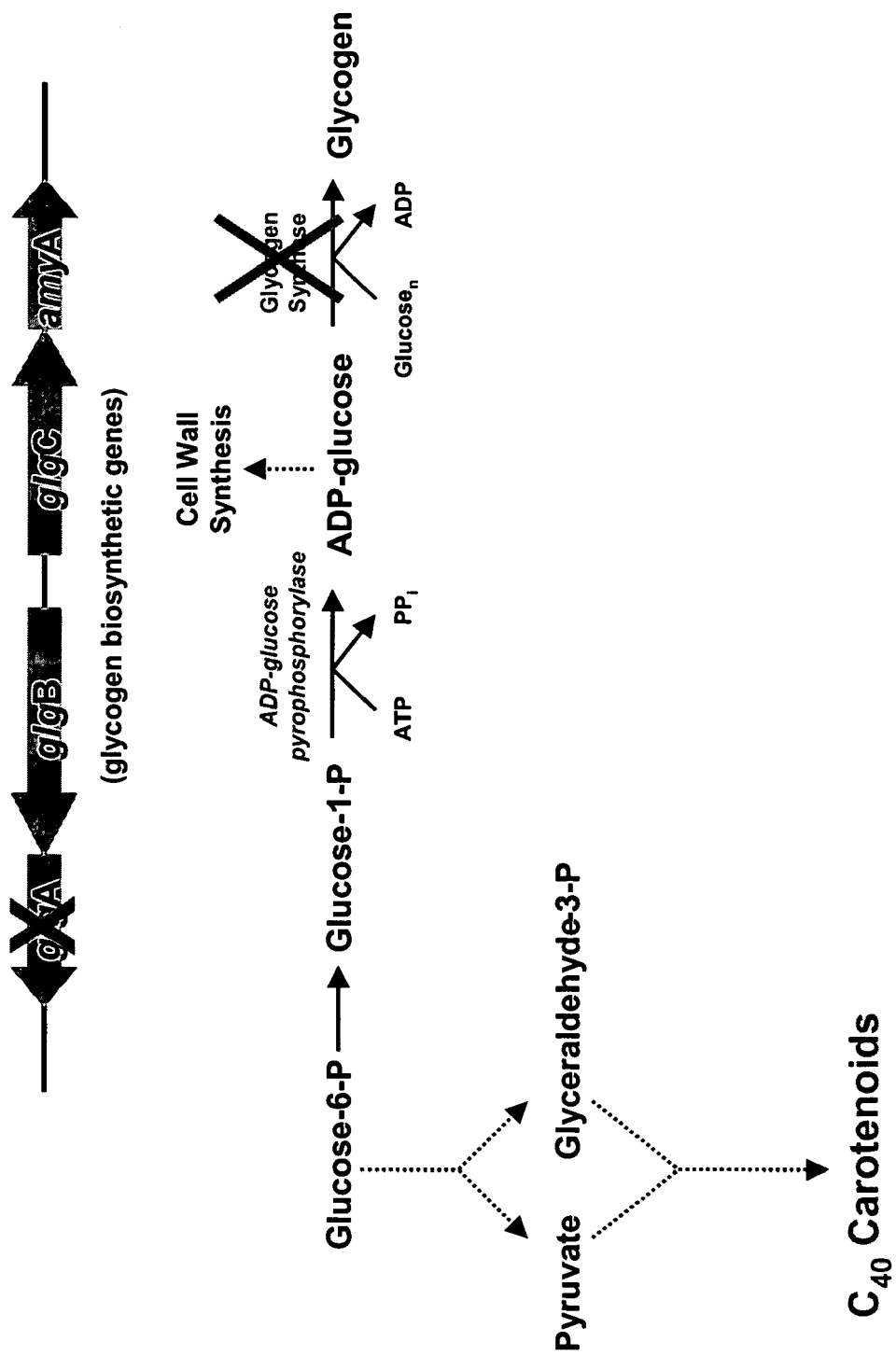

FIG. 2. Glycogen biosynthetic pathway genes. Down-regulating and/or disrupting glycogen synthase (glgA) expression increases the production of $C_{40}$ carotenoids in carotenogenic microorganisms.

Figure 3:
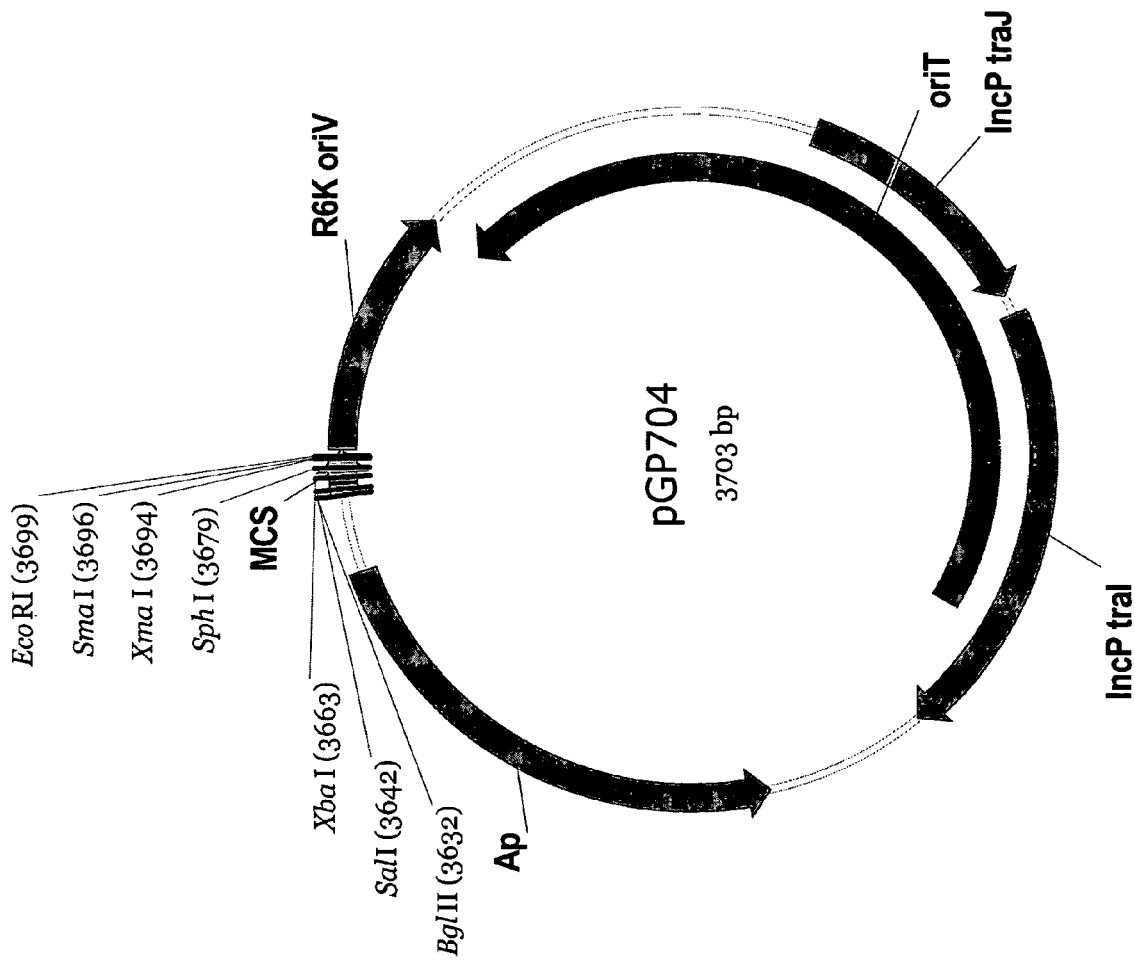

FIG. 3 is a plasmid map of pGP704.

The invention can be more fully understood from the following detailed description and the accompanying sequence descriptions, which form a part of this application.

The following sequences conform with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleotide sequence of the npr-sacB cassette amplified from plasmid pBE83.

SEQ ID NO: 2 is the nucleotide sequence of primer DrdI/npr-sacB.

SEQ ID NO: 3 is the nucleotide sequence of primer TthIII/npr-sacB.

SEQ ID NO: 4 is the nucleotide sequence of plasmid pGP704::sacB.

SEQ ID NO: 5 is the nucleotide sequence of plasmid pDCQ343.

SEQ ID NO: 6 is the nucleotide sequence of the crtW ketolase from Sphingomonas melonis DC18 (U.S. Ser. No. 11/015,433).

SEQ ID NO: 7 is the nucleotide sequence of the crtZ hydroxylase from Brevundimonas vesicularis DC263 (U.S. 60/601,947).

SEQ ID NO: 8 is the nucleotide sequence of "glgA deletion fragment #1".

SEQ ID NO: 9 is the nucleotide sequence of "glgA deletion fragment #2".

SEQ ID NO: 10 is the nucleotide sequence of primer "BglII/glgA (deletion) #1".

SEQ ID NO: 11 is the nucleotide sequence of primer "XbaI,SpeI,MluI/glgA (deletion) #1".

SEQ ID NO: 12 is the nucleotide sequence of primer "MluI,SpeI/glgA (deletion) #2".

SEQ ID NO: 13 is the nucleotide sequence of primer "XbaI/glgA (deletion) #2".

SEQ ID NO: 14 is the nucleotide sequence of plasmid pGP704::sacB::ΔglgA.

SEQ ID NO: 15 is the nucleotide sequence of the coding sequence of the glgA gene in Methylomonas sp. 16a.

SEQ ID NO: 16 is the deduced amino acid sequence encoded by the glgA gene in Methylomonas sp. 16a.

SEQ ID NO: 17 is the nucleotide sequence of the coding sequence of the glgA gene in Escherichia coli strain MC1061.

SEQ ID NO: 18 is the deduced amino acid sequence encoded by the glgA gene in Escherichia coli.

SEQ ID NO: 19 is the nucleotide sequence of "E. coli glgA deletion fragment #1".

SEQ ID NO: 20 is the nucleotide sequence of "E. coli glgA deletion fragment #2".

SEQ ID NO: 21 is the nucleotide sequence of primer "E. coli BglII/glgA (deletion) #1".

SEQ ID NO: 22 is the nucleotide sequence of primer "E. coli NotI,XbaI/glgA (deletion) #1".

SEQ ID NO: 23 is the nucleotide sequence of primer "E. coli NotI/glgA (deletion) #2"

SEQ ID NO: 24 is the nucleotide sequence of primer "E. coli XbaI/glgA (deletion) #2".

SEQ ID NO: 25 is the nucleotide sequence of plasmid "pGP704::sacB::E. coli ΔglgA".

SEQ ID NO: 26 is the 16s rRNA gene sequence from Methylomonas sp. 16a (ATCC PTA-2402) and derivatives thereof such as Methylomonas sp. MWM1200 (ATCC PTA-6887) and Methylomonas sp. MWM1500 (ATCC PTA-6888).

The following biological deposits were made under the terms of the Budapest Treaty on the International Recognition of the Deposit of Microorganisms for the Purposes of Patent Procedure:

| Depositor Identification Reference | International Depository Designation | Date of Deposit |
|---|---|---|
| Methylomonas 16a | ATCC PTA-2402 | Aug. 22, 2000 |
| Methylomonas sp. MWM1200 | ATCC PTA-6887 | Jul. 22, 2005 |
| Methylomonas sp. MWM1500 | ATCC PTA-6888 | Jul. 22, 2005 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

Definitions

In this disclosure, a number of terms and abbreviations are used. The following definitions are provided.

As used herein, the term "comprising" means the presence of the stated features, integers, steps, or components as referred to in the claims, but that it does not preclude the presence or addition of one or more other features, integers, steps, components or groups thereof.

"Open reading frame" is abbreviated ORF.

"Polymerase chain reaction" is abbreviated PCR.

"High Performance Liquid Chromatography" is abbreviated HPLC.

"Kanamycin" is abbreviated Kan.

"Ampicillin" is abbreviated Amp.

"Streptomycin" is abbreviated Str.

"Adenosine diphosphate" is abbreviated ADP.

"5-bromo-4-chloro-3-indolyl-β-D-galactopyranoside" is abbreviated X-gal.

As used herein, the terms "glycogen synthase", "bacterial glycogen synthase", "starch synthase", and "ADP-glucose-starch glucosyltransferase" will be used to describe the enzyme responsible for catalyzing glycogen chain elongation through the addition of adenylated glucose units in the form of ADP-glucose to a glycogen chain (E.C. 2.4.1.21).

As used herein, the term "glycogen" is used to describe a polysaccharide composed of a main chain of (α1-4)-linked glucose units with (α1→6)-linked branches occurring about every 8 to about 12 residues in the main polysaccharide chain. Glycogen is the main carbon and energy storage product in most animal cells, fungi, algae, and bacteria.

As used herein, the term "isoprenoid compound" or "carotenoid compound" refers to compounds formally derived from isoprene (2-methylbuta-1,3-diene; $CH_2=C(CH_3)CH=CH_2$), the skeleton of which can generally be discerned in repeated occurrence in the molecule. These compounds are produced biosynthetically via the isoprenoid/carotenoid pathway beginning with isopentenyl pyrophosphate (IPP) and formed by the head-to-tail condensation of isoprene units, leading to molecules which may be, for example, of 5, 10, 15, 20, 30, or 40 carbons in length.

As used herein, the terms "carotenogenic microorganism", "carotenogenic microbial host cell", and "carotenogenic host cell" refer to microorganisms capable of producing carotenoids and xanthophylls. In one aspect, the microorganisms of the present invention include those that naturally produce at least one carotenoid compound or those engineered to recombinantly produce at least one carotenoid compound. In another aspect, a carotenogenic microorganism may also include a microorganism comprising a downregulated and/or disrupted glycogen synthase gene that is subsequently engineered to recombinantly produce at least one carotenoid compound. In yet another aspect, carotenogenic microorganisms include carotenogenic bacteria, fungi, and algae. In yet another embodiment, the carotenogenic microorganism is a carotenogenic bacterium or carotenogenic yeast. In a further embodiment, the carotenogenic bacteria is a methylotroph. In yet a further embodiment, the carotenogenic bacteria is selected from the group consisting of *Escherichia coli*, *Methylomonas* sp. 16a, and derivatives thereof.

A used herein the term "high flux carotenogenic microbial host" will refer to a carotenogenic microbial host having the ability to produce carotenoid compounds and having a disruption in, or downregulation of, the native gene or genes encoding glycogen synthase.

As used herein, the term "carotenoid biosynthetic pathway" refers to those genes comprising members of the upper carotenoid pathway and/or lower carotenoid biosynthetic pathway, as illustrated in FIG. 1.

As used herein, the terms "upper carotenoid pathway" and "upper pathway" are used interchangeably and refer to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase; also known as ispC); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "lytB" gene (also known as ispH) involved in the formation of dimethylallyl diphosphate; the "gcpE" gene (also known as ispG) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid/carotenoid pathway.

As used herein, the terms "lower carotenoid biosynthetic pathway" and "lower pathway" will be used interchangeably and refer to those enzymes which convert FPP to a suite of carotenoids. These include those genes and gene products that are involved in the immediate synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$–$C_{40}$ carotenoids are included within the lower carotenoid biosynthetic pathway. These genes and gene products comprise all of the "crt" genes including, but not limited to: crtM, crtN1, crtN2, crtE, crtX, crtY, crtI, crtB, crtR, crtZ, crtW, bkt, crtO, crtA, crtC, crtD, crtF, and crtU. In one aspect, the lower carotenoid biosynthetic pathway genes are those involved in the production of $C_{40}$ carotenoids including, but not limited to crtB, crtE, crtI, crtO, crtW, bkt, crtY, and crtZ. As used herein, the term "lower carotenoid biosynthetic enzyme" is an inclusive term referring to any and all of the enzymes in the present lower pathway including, but not limited to: CrtM, CrtN1, CrtN2, CrtE, CrtX, CrtY, CrtI, CrtB, CrtR, CrtZ, CrtW, CrtO, CrtA, CrtC, CrtD, CrtF, and CrtU. In one aspect, the lower carotenoid biosynthetic pathway enzymes are those involved in the production of $C_{40}$ carotenoids including, but not limited to CrtB, CrtE, CrtI, CrtO, CrtW, CrtY, and CrtZ.

As used herein, the term "carotenoid" refers to a class of hydrocarbons having a conjugated polyene carbon skeleton formally derived from isoprene. This class of molecules is composed of $C_{30}$ diapocarotenoids and $C_{40}$ carotenoids and their oxygenated derivatives (xanthophylls).

As used herein, "$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure (hereinafter referred to as "diapophytoene"), having a long central chain of conjugated double bonds, by: (i) hydrogenation (ii) dehydrogenation (iii) cyclization, (iv) oxidation, (v) esterification/glycosylation, or any combination of these processes.

As used herein, "tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure. Non-limiting examples of $C_{40}$ carotenoids include: phytoene, lycopene, β-carotene, zeaxanthin, astaxanthin, and canthaxanthin.

The term "CrtE" refers to a geranylgeranyl pyrophosphate synthase enzyme encoded by the crtE gene and which converts trans-trans-farnesyl diphosphate and isopentenyl diphosphate to pyrophosphate and geranylgeranyl diphosphate.

The term "Idi" refers to an isopentenyl diphosphate isomerase enzyme (E.C. 5.3.3.2) encoded by the idi gene.

The term "CrtY" refers to a lycopene cyclase enzyme encoded by the crtY gene which converts lycopene to β-carotene.

The term "CrtI" refers to a phytoene desaturase enzyme encoded by the crtI gene. CrtI converts phytoene into lycopene via the intermediaries of phytofluene, ζ-carotene and neurosporene by the introduction of 4 double bonds.

The term "CrtB" refers to a phytoene synthase enzyme encoded by the crtB gene which catalyzes the reaction from prephytoene diphosphate to phytoene.

The term "CrtZ" refers to a carotenoid hydroxylase enzyme (e.g. β-carotene hydroxylase) encoded by the crtZ gene which catalyzes a hydroxylation reaction. The oxidation reaction adds a hydroxyl group to cyclic carotenoids having a β-ionone type ring. This reaction converts cyclic carotenoids, such as β-carotene or canthaxanthin, into the hydroxylated carotenoids zeaxanthin or astaxanthin, respectively. Intermediates in the process typically include β-cryptoxanthin and adonirubin. It is known that CrtZ hydroxylases typically exhibit substrate flexibility, enabling production of a variety of hydroxylated carotenoids depending upon the available substrates.

The term "CrtW" refers to a β-carotene ketolase enzyme encoded by the crtW gene which catalyzes an oxidation reaction where a keto group is introduced on the β-ionone type ring of cyclic carotenoids. This reaction converts cyclic carotenoids, such as β-carotene or zeaxanthin, into the ketocarotenoids canthaxanthin or astaxanthin, respectively. Intermediates in the process typically include echinenone and adonixanthin. It is known that CrtW ketolases typically exhibit substrate flexibility, enabling production of a variety of ketocarotenoids depending upon the available substrates.

The term "CrtX" refers to a zeaxanthin glucosyl transferase enzyme encoded by the crtX gene and which converts zeaxanthin to zeaxanthin-β-diglucoside.

As used here, the term "$C_1$ carbon substrate" refers to any carbon-containing molecule that lacks a carbon-carbon bond. Non-limiting examples are methane, methanol, formaldehyde, formic acid, formate, methylated amines (e.g., mono-, di-, and tri-methyl amine), methylated thiols, and carbon dioxide. In a preferred embodiment, the $C_1$ carbon substrates are selected from the group consisting of methanol and methane.

As used herein, the term "$C_1$ metabolizing bacteria" refers to bacteria that have the ability to use a single carbon substrate as their sole source of energy and biomass. $C_1$ metabolizing bacteria, a subset of $C_1$ metabolizers, will typically be methylotrophs and/or methanotrophs.

As used herein, the term "methylotroph" means an organism capable of oxidizing organic compounds that do not contain carbon-carbon bonds. In one embodiment, the methylotroph is a methylotrophic bacteria capable of using a methanol and/or methane as a primary carbon source.

As used herein, the term "methanotroph" or "methanotrophic bacteria" means a methylotrophic bacteria capable of utilizing methane as its primary source of carbon and energy. Complete oxidation of methane to carbon dioxide occurs by aerobic degradation pathways (U.S. Pat. Nos. 6,555,353; 6,689,601). Typical examples of methanotrophs useful in the present invention include (but are not limited to) the genera *Methylomonas*, *Methylobacter*, *Methylococcus*, and *Methylosinus*. In one embodiment, the methanotrophic bacteria utilizes methane and/or methanol as its primary carbon source.

As used herein, the term "high growth methanotrophic bacterial strain" refers to a bacterium capable of growth with methane and/or methanol as the sole carbon and energy source and which possesses a functional Embden-Meyerhof carbon flux pathway, resulting in a high rate of growth and yield of cell mass per gram of $C_1$ substrate metabolized (U.S. Pat. No. 6,689,601; hereby incorporated by reference). The specific "high growth methanotrophic bacterial strain" described herein is referred to as "*Methylomonas* 16a ATCC PTA-2402", "16a" or "*Methylomonas* sp. 16a", which terms are used interchangeably and which refer to the *Methylomonas* strain (and derivatives thereof) used in the present invention. In one aspect, the term "mutant derivatives of *Methylomonas* sp. 16a" or "derivatives of *Methylomonas* sp. 16a" refers to *Methylomonas* strains developed from *Methylomonas* sp. 16a (ATCC PTA-2402). In a further aspect, the mutant derivatives of *Methylomonas* sp. 16a are comprised of the 16s rRNA gene sequence as represented by SEQ ID NO: 26 (U.S. Pat. No. 6,689,601; hereby incorporated by reference).

As used herein, the terms "crtN1 gene cluster", "$C_{30}$ crt gene cluster", "crt gene cluster", and "endogenous *Methylomonas* 16a crt gene cluster" refer to an operon comprising crtN1, ald, and crtN2 genes that is active in the native $C_{30}$ carotenoid biosynthetic pathway of *Methylomonas* sp. 16a (U.S. Ser. No. 10/997,844).

As used herein, the term "CrtN1" refers to an enzyme encoded by the crtN1 gene, active in the native carotenoid biosynthetic pathway of *Methylomonas* sp. 16a. This gene is located within an operon comprising crtN2 and ald.

As used herein, the term "ALD" refers to an enzyme (an aldehyde dehydrogenase) encoded by the ald gene, active in the native carotenoid biosynthetic pathway of *Methylomonas* sp. 16a. This gene is located within an operon comprising crtN1 and crtN2. As used herein, the gene and gene product of the ald gene may be optionally referred to as "aldehyde dehydrogenase".

As used herein, the term "CrtN2" refers to an enzyme encoded by the crtN2 gene, active in the native carotenoid biosynthetic pathway of *Methylomonas* sp. 16a. This gene is located within an operon comprising crtN1 and ald.

As used herein, the term "CrtN3" refers to an enzyme encoded by the crtN3 gene, active in the native carotenoid biosynthetic pathway of *Methylomonas* sp. 16a. Disruption of the crtN3 gene significantly increases carotenoid production (U.S. Ser. No. 10/997,844).

As used herein, the term "pigmentless" or "white mutant" refers to a *Methylomonas* sp. 16a bacterium wherein the native pink pigment (e.g., a $C_{30}$ carotenoid) is not produced (U.S. Ser. No. 10/997,844; incorporated herein by reference). Thus, the bacterial cells appear white in color, as opposed to pink. Exemplified herein is the use of a *Methylomonas* sp. 16a derivative "MWM1200". As used herein, the term "MWM1200 (Δcrt cluster promoter+ΔcrtN3)" or "*Methylomonas* sp. MWM1200" refers to a derivative of *Methylomonas* sp. 16a in which the crtN1 gene cluster and the crtN3 gene have been disrupted. *Methylomonas* MWM1200 was created by disrupting expression of the native $C_{30}$ carotenoid pathway genes crtN1, ald, crtN2, and crtN3 (U.S. Ser. No. 10/997,844). *Methylomonas* sp. MWM1200 has been deposited to the American Type Culture Collection (ATCC®) under deposit number PTA-6887.

As used herein, the terms "*Methylomonas* sp. MWM1500" and "MWM1500" are used to describe a *Methylomonas* sp. 16a (ATCC PTA-2402) derivative created by down-regulating/disrupting expression of the glgA gene in *Methylomonas* MWM1200. *Methylomonas* sp. MWM1500 has been deposited to ATCC under deposit number PTA-6888.

The term "disruption" as used herein in the context of gene or genetic construct encoding a polypeptide means any action at the nucleic acid level that results in; a) a decrease in activity of an encoded polypeptide; b) elimination of the encoded polypeptide activity, c) transcription of an incomplete polypeptide sequence; d) incorrect folding of an encoded polypeptide; e) interference with the encoded RNA transcript, or any other activity resulting in a down-regulation of the gene. A gene my be disrupted for example by insertion of a foreign set of base pairs in a coding region, deletion of any portion of the gene, or by the presence of antisense sequences that interfere with transcription or translation of the gene. Disrupted genes re down-regulated. As used herein, the term "down-regulated" refers to a gene that has been mutated, altered, and/or disrupted such that the expression of the gene is less than that associated with the native gene sequence. In another aspect, the term down-regulated may include any mutation that decreases or eliminates the activity of the enzyme encoded by the mutant gene. In another embodiment, down-regulated includes elimination of the gene's expression (i.e. gene knockout). As used herein, the symbol "Δ" will be used to denote a mutation in the specified coding sequence and/or promoter wherein at least a portion (up to and including all) of said coding sequence and/or promoter has been disrupted by a deletion, mutation, or insertion. In another embodiment, the disruption can occur by optionally inserting a nucleic acid molecule into the native sequence whereby the expression of the mutated gene is down-regulated (either partially or completely). In yet another embodiment, down-regulation of glycogen synthase expression can occur by down-regulating, altering, or disruption expression of one or more transcription factors influencing expression of the glycogen synthase gene.

As used herein, the term "ΔglgA" will be used to describe microorganism having a deletion in a portion of the glycogen synthase gene (glgA) whereby glycogen synthase activity (E.C. 2.4.1.21) is decreased, down-regulated, and/or disrupted. As exemplified herein, the effects of deleting the glycogen synthase gene (glgA) were evaluated in two divergent microorganisms (*Methylomonas* sp. 16a ATCC PTA 2402, SEQ ID NO: 15; and *Escherichia coli* MC1061, SEQ ID NO: 17) engineered to recombinantly produce $C_{40}$ carotenoids. As used herein, "down-regulated" includes any decrease in glycogen synthase activity as the result of an addition, deletion, or mutation to the native glycogen synthase gene and may include a partial or complete disruption in glycogen synthase activity. Methods to decrease and/or disrupt gene expression are well known in the art. In one aspect, glycogen synthase activity can be decreased and/or disrupted by deleting the entire glgA gene. In another aspect, a portion of the glgA gene is deleted. In yet another aspect, the promoter operably linked to the glgA open reading frame is mutated to decrease and/or disrupt glycogen synthase expression. In still another aspect, the ribosomal binding site is altered to decrease and/or disrupt glycogen synthase expression. In a further embodiment, glycogen synthase activity is decreased, down regulated, and/or disrupted by inserting one or more nucleic acid fragments into a portion of the endogenous glgA gene. In a preferred aspect, glycogen synthase activity is disrupted. In yet a further embodiment, the glycogen synthase activity is down regulated, decreased, and/or disrupted using antisense RNA expression.

As used herein, the term "positive selection" means a selection method that enables only those cells that carry a DNA insert integrated at a specific chromosomal location to grow under particular conditions. In contrast, negative selection is based on selection methods whereby only those individuals that do not possess a certain character (e.g., cells that do not carry a DNA insert integrated at a specific chromosomal location) are selected.

As used herein, the term "homologous recombination" refers to the exchange of DNA fragments between two DNA molecules (during cross over). The fragments that are exchanged are flanked by sites of identical nucleotide sequences between the two DNA molecules (i.e., homologous DNA regions). Homologous recombination is the most common means for generated genetic diversity in microbes.

As used herein, the term "chromosomal integration" means that a chromosomal integration vector becomes congruent with the chromosome of a microorganism through recombination between homologous DNA regions on the chromosomal integration vector and within the chromosome.

As used herein, the term "chromosomal integration vector" or "integration vector" means an extra-chromosomal vector that is capable of integrating into the host's genome through homologous recombination.

As used herein, the term "suicide vector" or "positive selection vector" refers to a type of chromosomal integration vector that is capable of replicating in one host but not in another. Thus, the vector is conditional for its replication.

As used herein, the terms "single-crossover event" and "plasmid integration" are used interchangeably and mean the incorporation of a chromosomal integration vector into the genome of a host via homologous recombination between regions of homology between DNA present within the chromosomal integration vector and the host's chromosomal DNA. A "single-crossover mutant" refers to a cell that has undergone a single-crossover event.

As used herein, the terms "double-crossover event", "allelic exchange", and "gene replacement" are used interchangeably and mean the homologous recombination between a DNA region within the chromosomal integration vector and a region within the chromosome that results in the replacement of the functional chromosomal nucleotide sequence of interest (i.e., chr-NSI) with a homologous plasmid region (i.e., the replacement nucleotide sequence of interest, or re-NSI). A "double-crossover mutant" or "allelic exchange mutant" is the result of a double-crossover event. This mutant can be generated by two simultaneous reciprocal breakage and reunion events between the same two DNA fragments; alternatively, a double-crossover mutant can be the result of two single-crossovers that occur non-simultaneously.

As used herein, the term "chromosomal nucleotide sequence of interest" or "chr-NSI" refers to a specific chromosomal sequence that is targeted for homologous recombination. In one embodiment, the chr-NSI encodes is a microbial glycogen synthase gene (glgA) encoding an enzyme having glycogen synthase activity (E.C. 2.4.1.21). In preferred embodiment, the chr-NSI is the glycogen synthase gene (glgA) in *Methylomonas* sp. 16a or *Escherichia coli*.

As used herein, the term "replacement nucleotide sequence of interest" or "re-NSI" refers to a nucleotide sequence of interest that is cloned into a chromosomal integration vector for the purpose of inducing homologous recombination with a chromosomal sequence. The re-NSI is modified with respect to chr-NSI by the addition, deletion, or substitution of at least one nucleotide. Sufficient homology must exist, however, between the two nucleotide sequences of interest to enable homologous recombination to occur. For the purposes herein, re-NSI will enable production of a mutant microbial host cell having a deletion (partial or complete) in at least one glycogen synthase gene (glgA) or a deletion in the promoter driving transcription of the endogenous glycogen synthase coding sequence.

As used herein, the term "genetic marker" or "selectable marker" means a phenotypic trait that can be visualized under special conditions. For example, an antibiotic resistance marker serves as a useful selectable marker, since it enables detection of cells which are resistant to the antibiotic, when cells are grown on media containing that particular antibiotic.

As used herein, the term "SacB" means a *Bacillus* encoded protein that catalyzes the conversion of sucrose into levan, a product that is toxic to most Gram-negative microorganisms. The term "sacB" means a gene that encodes the "SacB" protein.

A "nucleic acid" is a polymeric compound comprised of covalently linked subunits called nucleotides. Nucleic acids include polyribonucleic acid (RNA) and polydeoxyribonucleic acid (DNA), both of which may be single-stranded or double-stranded. DNA includes cDNA, genomic DNA, synthetic DNA, and semi-synthetic DNA.

As used herein, an "isolated nucleic acid fragment" or "isolated nucleic acid molecule" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. In one aspect, the isolated nucleic acid molecule is a coding region or gene encoding a polypeptide.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. In one embodiment, substantially similar nucleic acid fragments of the instant invention are those nucleic acid fragments encoding polypeptides having at least 80% identity to the amino acid sequences reported herein. In another embodiment, substantially similar nucleic acid fragments are those encoding polypeptides having at least about 90% identity to the amino acid sequences of the glycogen synthases described herein. In yet a further embodiment, substantially similar nucleic acid fragments encode polypeptides having an amino acid sequence having at least about 95% identity to the amino acid sequences reported herein. In still yet a further embodiment, substantially similar nucleic acid fragments encode polypeptides having an amino acid sequence having at least about 99% identity to the amino acid sequences reported herein.

In one aspect, substantially similar nucleic acid fragments of the instant invention are those nucleic acid fragments whose DNA sequences are at least about 80% identical to the DNA sequence of the nucleic acid fragments reported herein. In another aspect, substantially similar nucleic acid fragments are at least about 90% identical to the DNA sequence of the nucleic acid fragments reported herein. In yet a further aspect, substantially similar nucleic acid fragments are at least about 95% identical to the DNA sequence of the nucleic acid fragments reported herein. In still yet a further aspect, substantially similar nucleic acid fragments are at least about 99% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. In one embodiment, the stringency conditions use a series of washes starting with 6×SSC, 0.5% SDS at room temperature for about 15 min, then repeated with 2×SSC, 0.5% SDS at about 45° C. for about 30 min, and then repeated twice with 0.2×SSC, 0.5% SDS at about 50° C. for about 30 min. In another embodiment, the stringency conditions use higher temperatures in which the washes are identical to those above except for the temperature of the final two 30 min washes in 0.2×SSC, 0.5% SDS was increased to about 60° C. In yet another embodiment, highly stringent conditions use two final washes in 0.1×SSC, 0.1% SDS at about 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well-known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment, the length for a hybridizable nucleic acid is at least about 10 nucleotides. In another embodiment, the minimum length for a hybridizable nucleic acid is at least about 15 nucleotides; in yet another embodiment at least about 20 nucleotides; and in yet a further embodiment, the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene sufficient to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising about 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of about 12–15 bases may be used as amplification primers in PCR in order to obtain a particular nucleic acid fragment comprising the primers. Accordingly, a substantial portion of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing As used herein, "gene" refers to a nucleic acid fragment that expresses a specific protein. It may or may not include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, the term "homolog" or "homologue", as applied to a gene, means any gene derived from the same or a different microbe having the same function. A homologous gene may have significant sequence similarity. In one embodiment, glgA homologs are substantially similar to the sequences reported herein and encode enzymes having glycogen synthase activity (E.C. 2.4.1.21). The sequences reported herein can be used to identify glycogen synthase genes in other organisms for the purpose of disrupting or down-regulating glycogen synthase activity.

As used herein, the term "coding sequence" or "coding region of interest" refers to a DNA sequence that codes for a specific amino acid sequence.

As used herein, the term "suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing sites, effector binding sites, and stem-loop structures.

As used herein, the term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

As used herein, the term "3' non-coding sequences" refers to DNA sequences located downstream of a coding sequence and include sequences encoding regulatory signals capable of affecting mRNA processing or gene expression.

As used herein, the term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

"Transformation" refers to the transfer of a nucleic acid fragment into the genome of a host organism, resulting in genetic inheritance. In the present invention, the host cell's genome is comprised of chromosomal and extrachromosomal (e.g. plasmid) genes. Host organisms containing the transformed nucleic acid fragments are referred to as "transgenic", "recombinant" or "transformed" organisms.

As used herein, "conjugation" refers to a particular type of transformation in which a unidirectional transfer of DNA (e.g., from a bacterial plasmid) occurs from one bacterium cell (i.e., the "donor") to another (i.e., the "recipient"). The process involves direct cell-to-cell contact.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction. "Transformation cassette" refers to a specific vector containing a foreign gene and having elements (in addition to the foreign gene) that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package Version 9.0, Genetics Computer Group (GCG), Madison, Wis.); BLASTP, BLASTN, BLASTX (Altschul et al., *J. Mol. Biol.* 215:403–410 (1990)); DNASTAR (DNASTAR, Inc., Madison, Wis.); and the FASTA program incorporating the Smith-Waterman algorithm (W. R. Pearson, *Comput. Methods Genome Res.*, [Proc. Int. Symp.], Meeting Date 1992, 111–20. Suhai, Sandor, Ed.; Plenum: New York, N.Y. (1994)). Within the context of this application it will be understood that where sequence analysis software is used for analysis, the results of the analysis are based on the "default values" of the program referenced, unless otherwise specified. As used herein "default values" will mean any set of values or parameters (set by the software manufacturer) which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

Glycogen Synthesis

Glycogen is a polysaccharide composed of a main chain of ($\alpha$1–4)-linked glucose units with ($\alpha$1→6)-linked branches occurring about every 8 to about 12 residues in the main polysaccharide chain. Glycogen is the main carbon and energy storage product in most animals, fungi, algae, and bacteria. In many microorganisms, glycogen is typically made in response to non-carbon nutrient limitations, especially ammonia limitation and aids in sporulation and spore recovery.

Glycogen chain elongation typically requires an activated glycosyl monomer. The activated monomer (glycosyl donor) used in glycogen synthesis is uridine diphosphate (UDP)-glucose (vertebrate animals, typically in muscle or liver cells) or an adenosine diphosphate (ADP)-glucose (bacteria, fungi, etc.). The activated monomer in most microorganisms is typically synthesized from glucose-1-phosphate and adenosine triphosphate (ATP).

Glucose-6-phosphate (G-6-P), a common metabolite found nearly all microorganisms, is converted into glucose-1-phosphate (G-1-P) by the enzyme activity of a phosphoglucomutase (FIG. 2). The addition of ATP to G-1-P via the enzymatic activity of an ADP-glucose synthase forms ADP-glucose plus pyrophosphate. The enzyme glycogen synthase (E.C. 2.4.1.21), encoded by the gene glgA, is responsible for catalyzing glycogen chain elongation through the addition of adenylated glucose units in the form of ADP-glucose to a glycogen chain as shown in Formula 1.

Formula 1:

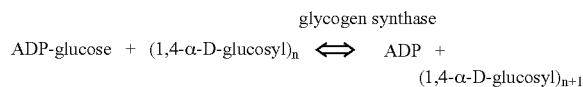

Disruption of glgA

Disruption of the glgA gene in the glycogen biosynthetic pathway was targeted to eliminate glycogen production while preserving the production of ADP-glucose, an intermediate that assumes a key role in the interconversion of sugars and biosynthesis of more complex extracellular polysaccharides and cell wall constituents necessary for cell growth.

As exemplified herein, down-regulation and/or disruption of the glgA gene increased carotenoid production in two unrelated carotenogenic microorganisms (*E. coli* and *Methylomonas* sp.). Given the ubiquitous nature of glycogen synthesis and the number of microorganisms currently used to produce carotenoids (either naturally or recombinantly), the present method should be widely applicable to any carotenogenic microorganism having a glycogen synthase gene (glgA).

The effect of glgA down-regulation/disruption/deletion is currently exemplified in two different carotenogenic bacterial strains engineered to produce at least one carotenoid compound. The *E. coli* glgA gene (SEQ ID NO: 17) and the *Methylomonas* sp. 16a glgA gene (SEQ ID NO: 15) were independently disrupted and evaluated in each host. In both carotenogenic hosts, disruption/deletion of the native glgA gene resulted in a significant increase in carotenoid production. In one embodiment, one or more of the lower carotenoid pathway genes are extrachromosomally expressed. In another embodiment, one or more of the lower carotenoid pathway genes are chromosomally expressed.

In addition to the exemplified glgA genes, there are a variety of techniques known by one of skill in the art to identify glycogen synthase genes in other microorganisms suitable for carotenoid production. A number of organisms reported to have at least one glycogen synthase gene including, but not limited to those listed in Table 1.

TABLE 1

Glycogen synthase genes reported in a variety of organisms.
Glycogen Synthase Genes (E.C. 2.4.1.21)
(Source organism and GenBank ® Accession Information)

*Escherichia coli*; CAA23545, AE016768, J02616, AAA23870, NP_756080
*Bacillus subtilis*; Z25795
*Agrobacterium tumefaciens*; P0A3F2, AF033856, L24117, U38977
*Bradyrhizobium japonicum*; Q89RJ4, Q89G86
*Synechocystis* sp. (strain PCC 6803); P74521, P72623
*Bacillus cereus*; Q72YJ6

TABLE 1-continued

Glycogen synthase genes reported in a variety of organisms.
Glycogen Synthase Genes (E.C. 2.4.1.21)
(Source organism and GenBank ® Accession Information)

*Rhizobium tropici*; AJ291603.1
*Streptomyces coelicolor* A3(2); AJ243803.1
*Ipomoea batatas*; U44126.1
*Methanococcus maripaludis* S2; NC_005791.1
*Mesorhizobium loti*; AF268969.1
*Sulfolobus acidocaldarius*; AJ294724.1
*Xanthomonas axonopodis* pv. Citri; AE01669.1
*Geobacillus stearothermophilus*; D87026.1
*Streptococcus pneumoniae* R6; AE008475.1
*Thermus caldophilus*; AF289823.1
*Rhodobacter sphaeroides*; AF181035.1
*Shigella flexneri*; NP_709205.1
*Salmonella enterica*; YP_152511.1
*Erwinia carotovora*; YP_052235.1
*Yersinia pseudotuberculosis*; YP_072265.1
*Haemophilus influenzae*; NP_439511.1
*Francisella tularensis* subsp. tularensis; YP_169460.1
*Bradyrhizobium japonicum*; NP_773099.1

Where it is desired to disrupt the glgA gene in a host selected for the production of carotenoid compounds it will be necessary to identify and isolate those glycogen synthase encoding genes. Isolation of homologous genes using sequence-dependent protocols is well-known in the art.

Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Natl. Acad. Sci. USA*, 82:1074 (1985)) or strand displacement amplification (SDA, Walker, et al., *Proc. Natl. Acad. Sci. U.S.A.*, 89:392 (1992)).

For example, genes encoding similar glycogen synthase proteins or polypeptides can be isolated directly by using all or a portion of the nucleic acid fragments described herein as DNA hybridization probes to screen libraries from any desired bacteria using methodology well known to those skilled in the art. Specific oligonucleotide probes based upon the nucleic acid sequences described herein can be designed and synthesized by methods known in the art (Maniatis). Moreover, the entire sequences can be used directly to synthesize DNA probes by methods known to the skilled artisan such as random primers DNA labeling, nick translation, end-labeling techniques, or RNA probes using available in vitro transcription systems. In addition, specific primers can be designed and used to amplify a part of or the full-length of the sequences described herein. The resulting amplification products can be labeled directly during amplification reactions or labeled after amplification reactions, and used as probes to isolate full length DNA fragments under conditions of appropriate stringency.

Typically in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W., in *Methods in Molecular Biology: PCR Protocols: Current Methods and Applications*, Vol. 15, pages 31–39, White, B. A. (ed.), (1993) Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor of a eukaryotic gene. In the case of microbial genes which lack polyadenylated mRNA, random primers may be used. Random primers may also be useful for amplification from DNA.

Alternatively, the second primer sequence may be based upon sequences derived from a cloning vector. For example, the skilled artisan can follow the RACE protocol (Frohman et al., *Proc. Natl. Acad. Sci. USA*, 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci. USA*, 86:5673 (1989); Loh et al., *Science*, 243: 217 (1989)).

Alternatively, the sequences described herein may be employed as hybridization reagents for the identification of homologs. The basic components of a nucleic acid hybridization test include a probe, a sample suspected of containing a glgA gene, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically, a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.*, 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kD), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Suitable host cells comprised of structurally similar glycogen synthase genes may also be identified using the present sequences. BLASTP analysis using the *Methylomonas* sp. 16a glgA gene (SEQ ID NO: 15) or the *E. coli* glgA gene (SEQ ID NO: 17) revealed that there are numerous structurally related glycogen synthases in GenBank®. The closest "hit" for each sequence is provided in Table 2.

TABLE 2

Top BLASTP Hits for the Glycogen Synthase Genes Isolated from Different Bacterial Species

| ORF Name | Gene Name | Similarity Identified | SEQ ID Nucleotide | SEQ ID Peptide | % Identity[a] | % Similarity[b] | E-value[c] | Citation |
|---|---|---|---|---|---|---|---|---|
| 1 | glgA *Escherichia coli* | Glycogen ssynthase gi\|26250040\|ref\|NP_756080.1\| *Escherichia coli* CFT073 | 17 | 18 | 100 | 100 | 0 | Welch et al., Proc. Natl. Acad. Sci. U.S.A., 99 (26), 17020–17024 (2002) |
| 2 | glgA *Methylomonas* sp. | Glycogen synthase gi\|53804456\|ref\|YP_113933.1\| *Methylococcus capsulatus* str. Bath | 15 | 16 | 54 | 71 | 7e-151 | Ward et al., PLoS Biol., 2 (10), E303 (2004) |

[a]% Identity is defined as percentage of amino acids that are identical between the two proteins.
[b]% Similarity iss defined as percentage of amino acids that are identical or conserved between the two proteins.
[c]Expected value. The Expected value estimates the statistical significance of the match, specifying the number of matches, with a given score, that are expected in a search of a database of this ssize absolutely by chance.

Disruption Involving the Creation of Allelic Exchange Mutants via Homologous Recombination and Positive Selection Methods of screening in microbiology are discussed at length in Brock, supra. The ability to produce specific defined mutations in a microorganism frequently relies on exploitation of the native homologous recombination properties of the cell to replace a chromosomal nucleotide sequence of interest (chr-NSI) with a replacement nucleotide sequence of interest (re-NSI). Typically, the re-NSI (i.e. ΔglgA) is a modified version of the wild type chr-NSI (i.e. glgA). As exemplified herein, this method can be used in a variety of bacteria including *Methylomonas* sp. (U.S. Ser. Nos. 10/997,309 and 10/997,844, each hereby incorporated by reference).

Briefly, the positive selection (or direct genetic selection) of mutant bacteria is possible whenever survival of the recombinant bacteria depends upon the presence or absence of a particular function encoded by the DNA that is introduced into the organism. The advantage of a selection method over a screening method is that growth of bacteria with the specific desired mutation is greatly favored over bacteria lacking that specific mutation, thus facilitating the identification of the preferred mutants.

Direct or positive selection vectors containing genes that convey lethality to the host are well known. For example, expression of the *Bacillus subtilis* or the *B. amyloliquefaciens* sacB genes in the presence of sucrose is lethal to *E. coli* and a variety of other Gram-negative and Gram-positive bacteria. The sacB gene encodes levansucrase, which catalyzes both the hydrolysis of sucrose and the polymerization of sucrose to form the lethal product levan. The inability of *E. coli* and many other gram negative bacteria to grow when sacB is expressed can be exploited to directly select for cells that have lost the sacB gene via homologous recombination. Numerous methods have been developed for the selection of various bacterial mutants, based on sacB. See for example: U.S. Pat. No. 6,048,694 (issued to Bramucci et al.) concerning *Bacillus*; U.S. Pat. No. 5,843,664 (issued to Pelicic et al.) concerning *mycobacterium*; U.S. Pat. No. 5,380,657 (issued to Schaefer et al.) concerning *Coryneform* bacteria; Hoang et al. (*Gene*, 212(1):77–86 (1998)) concerning *Pseudomonas aeruginosa*; Copass et al. (*Infection and Immun.*, 65(5): 1949–1952 (1997)) concerning *Helicobacter pylori*; and Kamoun et al. (*Mol. Microbiol.*, 6(6):809–816 (1992)) concerning *Xanthomonas*.

The principle of the two-step positive selection strategy based on use of sacB for bacteria relies on the application of a positive selection vector, in a preferred embodiment derived from the suicide delivery vector pGP704, which is able to integrate into the bacteria's chromosome to produce mutations that are the result of both single- or double-crossover events (FIG. 3). Specifically, the positive selection vector comprises:

(i) at least one gene encoding resistance to a first selectable marker (e.g., Amp, Kan, etc.);
(ii) a sacB coding region encoding a levansucrase enzyme under the control of a suitable promoter; and
(iii) a replacement nucleotide sequence of interest (re-NSI; ΔglgA), which one desires to insert into the chromosome of the bacteria as a replacement to an existing nucleotide sequence of interest in the bacterial chromosome (chr-NSI; glgA). Thus, re-NSI is modified with respect to chr-NSI by the addition, substitution, or deletion of at least one nucleotide.

Upon transformation of bacteria with the positive selection vector described above, a single-crossover event by homologous recombination occurs between chr-NSI and re-NSI, such that the entire positive selection vector is integrated into the bacterial chromosome at the site of crossover. These events can be selected by growth on the first selectable marker (e.g., Amp or Kan), whereby a complete copy of chr-NSI and a complete copy of re-NSI are present in the chromosome. Upon removal of selection by the first selectable marker, a second crossover event may occur, resulting in the "looping out" of the positive selection vector, to yield transformants containing either the chr-NSI or the re-NSI in the chromosome. Direct selection of these allelic exchange transformants is possible by growing the transformants in the presence of sucrose, since single-crossover mutants will be killed under these conditions.

One factor to consider regardless of the specific type of re-NSI generated is the overall homology between the re-NSI and the chr-NSI. In general, it is well known in the art that homologous recombination requires a minimum of about 50 nucleotides of homology on each side of the site of a crossover. When preparing a re-NSI for use in the selection processes described herein, it is preferable to have regions homologous to the chr-NSI flanking (both 5' and 3') the site of the addition, substitution, or deletion. More preferably, a 1 kB region of homology is preferred on both sides of the addition, substitution, or deletion. In contrast, re-NSI is not expected to be limited in length, beyond the limitations inherent to homologous recombination.

Generation of a re-NSI containing an addition, substitution, or deletion of at least one nucleotide with respect to the chr-NSI can be accomplished using numerous techniques known to a skilled artisan in the field of molecular biology. Although not intended to be limiting, deletions and additions may be generated by the use of restriction endonucleases, in vitro transposition reactions, or PCR methodologies; all techniques well known to one of skill in the art.

A preferred method for generation of a re-NSI is via PCR methodologies. Alternatively, substitutions may be generated by mutagenesis of the re-NSI. Two suitable approaches include error-prone PCR (Leung et al., *Technique*, 1:11–15 (1989); Zhou et al., *Nucleic Acids Res.*, 19:6052–6052 (1991); and Spee et al., *Nucleic Acids Res.*, 21:777–778 (1993)) and in vivo mutagenesis. The principal advantage of error-prone PCR is that all mutations introduced by this method will be within the re-NSI, and any change may be easily controlled by changing the PCR conditions. Alternatively, in vivo mutagenesis may be employed using commercially available materials such as *E. coli* XL1-Red strain, and the *Epicurian coli* XL1-Red mutator strain from Stratagene (La Jolla, Calif.; Greener and Callahan, *Strategies*, 7:32–34 (1994)). This strain is deficient in three of the primary DNA repair pathways (mutS, mutD, and mutT), resulting in a mutation rate 5000-fold higher than that of wild-type. In vivo mutagenesis does not depend on ligation efficiency (as with error-prone PCR); however, a mutation may occur at any region of the vector and the mutation rates are generally much lower.

It is also contemplated that it may be desirable to replace a wild-type gene of interest (i.e., chr-NSI) in the carotenogenic microorganism with a mutant gene (i.e., re-NSI) that has been constructed using the method of "gene shuffling" (U.S. Pat. Nos. 5,605,793; 5,811,238; 5,830,721; and 5,837, 458). The method of gene shuffling is particularly attractive due to its facile implementation, and high rate of mutagenesis. The process of gene shuffling involves the restriction of a gene of interest into fragments of specific size in the presence of additional populations of DNA regions of both similarity to, or difference to, the gene of interest. This pool of fragments is then denatured and reannealed to create a mutated gene. The mutated gene is subsequently screened for altered activity.

One factor to consider during the preparation of a re-NSI for use in the two-step selection strategy concerns the placement of the addition, deletion, or substitution within the sequence of interest. Specifically, the re-NSI is first inserted into the chromosome by integration of the chromosomal integration vector (a single-crossover event). The second crossover event that occurs can result in either a mutant or wildtype sequence in the chromosome, since the single-crossover contains two copies of the nucleotide sequence of interest. In order to increase the percentage of segregants that retain the re-NSI, as opposed to reverting to the wildtype encoded by the chr-NSI, it is desirable to "center" the mutation with respect to the flanking DNA that has homology to the chr-NSI. For example, if a point mutation was perfectly centered within a re-NSI, about 50% of the segregants would be expected to retain the mutation in the chromosome (thus producing a 1:1 ratio of double-crossover mutants to wild-type cells.

Differentiation between allelic exchange mutants containing the wildtype and mutant allele is then possible using standard molecular techniques (e.g., PCR), well known to one of skill in the art. One preferred advantage of the two-step selection strategy described above is that allelic exchange transformants that are produced are markerless (i.e., lacking any antibiotic or other genetic marker indicative of the allelic exchange).

As exemplified herein, a series of glgA deletion fragments were prepared (re-NSIs) and incorporated into the integration vector pGP704::sacB. The deletion fragments were prepared to have regions of homology to the wild type glgA gene. Tri-parental conjugation was used to introduce the integration vector into the host cell. Double crossover events resulting in the deletion of a functional glgA gene were determined using sucrose selection. PCR amplification reactions were conducted to confirm those colonies having a glgA deletion.

Alternative Methods to Disrupt, or Down-Regulate, glgA Expression

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Carotenogenic Microbial Host Cells

The present method involves the disruption of a glycogen synthase encoding gene (glgA) in a carotenogenic microbial host. "Carotenogenic microbial hosts" are those microbes that either possess the native genetic machinery to make carotenoid compounds or can be genetically engineered to do so. Thus, the present methods are suitable for any microorganism that endogenously or recombinantly produces compounds derived from farnesyl pyrophosphate (FPP). Recombinant expression of carotenoid biosynthetic pathway genes for recombinant carotenoid production is well known in the art. In one aspect, the FPP derived compounds are $C_{30}$ and/or $C_{40}$ carotenoids. In a preferred embodiment, the carotenoid compound is a $C_{40}$ carotenoid selected from the group consisting of antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin. In a preferred embodiment, the $C_{40}$ carotenoid is selected from the group consisting of β-carotene, lycopene, canthaxanthin, astaxanthin, and lutein.

Glycogen synthesis is common in many organisms including, but not limited to animals, fungi, bacteria, and cyanobacteria. Many microorganisms are known to produce, either endogenously or recombinantly, carotenoid compounds. In one aspect of the present invention, the carotenogenic host cell is a microorganism selected from the group consisting of fungi, bacteria, algae, and cyanobacteria. In a preferred embodiment, suitable carotenogenic microorganisms include, but are not limited to bacterial, algal, fungal or yeast species such as *Aspergillus, Trichoderma, Saccharomyces, Pichia, Phaffia, Candida, Hansenula,* or algal species such as *Haematococcus,* or bacterial species such as *Salmonella, Bacillus, Acinetobacter, Zymomonas, Agrobacterium, Erythrobacter, Erwinia, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus.* In one embodiment, the carotenogenic microorganism is selected from the group consisting of *Phaffia, Haematococcus, Escherichia, Methylomonas, Methylobacter, Methylococcus, Methylosinus, Methylomicrobium,* and *Methylocystis.* In yet another embodiment, the carotenogenic microorganism is a methylotrophic bacteria. In still another aspect, the carotenogenic microorganism is a carotenogenic bacteria selected from the group consisting of *Escherichia* and *Methylomonas.* In yet a further aspect, the carotenogenic bacteria is selected from the group consisting of *Escherichia coli, Methylomonas* sp. 16a (ATCC PTA-2402), and derivatives thereof.

*Methylomonas* sp. 16a

Methylotrophic bacteria represent an attractive microbial platform to produce carotenoids due to their ability to grow on inexpensive $C_1$ substrates such as methane and/or methanol. Methylotrophic bacteria can be engineered to produce carotenoids. As described in U.S. Ser. No. 09/941,947, *Methylomonas* sp. 16a ATCC PTA-2402 has been engineered to produce a variety of $C_{40}$ carotenoids. This strain (and derivatives thereof) is particularly useful for carbon flux manipulation as is has both Embden-Meyerhof and the Entner-Douderoff pathway enzymes (U.S. Pat. No. 6,689, 601; hereby incorporated by reference). As used herein, methylotrophic bacteria having a functional Embden-Meyerhof pathway are referred to as "high growth" methylotrophic (or methanotrophic if capable of utilizing methane as a primary carbon source) bacteria. Additional methanotrophic bacteria having this characteristic include, but are not limited to *Methylomonas clara* and *Methylosinus sporium.*

The Native $C_{30}$ Carotenoid Pathway of *Methylomonas* sp. 16a

*Methylomonas* sp. 16a (ATCC PTA-2402) naturally produces a $C_{30}$ carotenoid in very high concentrations within the cell. Production of this pigment is indicative of naturally high carbon flow through the isoprenoid/carotenoid pathway. The $C_{30}$ pathway has been disrupted in *Methylomonas* sp. 16a, creating a series of non-pigmented "white mutants" suitable for $C_{40}$ pathway engineering (U.S. Ser. No. 10/997, 844; hereby incorporated by reference). Exemplified herein is *Methylomonas* sp. MWM1200 (ATCC PTA-6887), a "white mutant" comprised of a deletion disrupting expression of the endogenous crtN1 gene cluster (i.e. crtN1-aldcrtN2) and a deletion in crtN3 gene. This strain produces significant quantities of the isoprenoid intermediates required for carotenoid biosynthesis. Expression of $C_{40}$ lower carotenoid biosynthesis pathway genes in MWM1200 results in the production of $C_{40}$ carotenoids. In one aspect, the $C_{40}$ carotenoid biosynthesis genes may be extrachromosomally expressed (i.e. vector based expression) or chromosomally integrated and expressed into the host cell. *Methylomonas* sp. 16a MWM1200 is comprised of a wild type glgA gene and produces significant amounts of glycogen (Example 5). Disruption of the glycogen synthase gene in *Methylomonas* sp. MWM1200 resulted in the creation of *Methylomonas* sp. MWM1500 (ATCC PTA-6888).

Genes Involved in Carotenoid Production

Once a suitable carotenogenic microbial host is identified, the production of carentoid compounds will be effected from that host either through the manipulation or enhancement of native pathways or the introduction of new pathways for the synthesis of carotenoids.

The enzyme pathway involved in the biosynthesis of carotenoid compounds can be conveniently viewed in two parts, the upper carotenoid pathway (providing for the conversion of pyruvate and glyceraldehyde-3-phosphate to farnesyl pyrophosphate) and the lower carotenoid biosynthetic pathway (which provides for the synthesis of either diapophytoene ($C_{30}$) or phytoene ($C_{40}$) and all subsequently produced carotenoids) (FIG. 1).

The upper carotenoid biosynthetic pathway leads to the production of a $C_5$ isoprene subunit, isopentenyl pyrophosphate (IPP); however, this biosynthetic process may occur through either of two pathways. First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.*, 111:135–140 (1993); Rohmer et al, *Biochem.*, 295: 517–524 (1993); Schwender et al., *Biochem.*, 316: 73–80 (1996); and Eisenreich et al., *Proc. Natl. Acad. Sci. USA*, 93: 6431–6436 (1996)). This mevalonate-independent pathway (FIG. 1) is characterized by, but not limited to, the enzymes encoded by the following genes: the "dxs" gene (encoding 1-deoxyxylulose-5-phosphate synthase); the "dxr" gene (encoding 1-deoxyxylulose-5-phosphate reductoisomerase; also known as ispC); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "lytB" gene (also known as ispH) involved in the formation of dimethylallyl diphosphate; the "gcpE" gene (also known as ispG) involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase). The synthesis of FPP occurs via the isomerization of IPP to dimethylallyl pyrophosphate (DMAPP). This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

The division between the upper carotenoid pathway and the lower carotenoid pathway is somewhat subjective. FPP synthesis is common in both carotenogenic and non-carotenogenic bacteria. As such, the first step in the lower carotenoid biosynthetic pathway is considered to begin with the conversion of farnesyl pyrophosphate (FPP) to compounds of two divergent pathways, which lead to the formation of either $C_{30}$ diapocarotenoids or $C_{40}$ carotenoids (FIG. 1).

For the biosynthesis of $C_{40}$ carotenoids, a series of enzymatic reactions catalyzed by CrtE and CrtB occur to convert FPP to geranylgeranyl pyrophosphate (GGPP) and then to phytoene, the first 40-carbon molecule of the lower carotenoid biosynthesis pathway. From the compound phytoene, a spectrum of $C_{40}$ carotenoids are produced by subsequent hydrogenation, dehydrogenation, cyclization, oxidation, or any combination of these processes. For example, lycopene is produced from phytoene through four sequential dehydrogenation reactions by the removal of eight atoms of hydrogen, catalyzed by phytoene desaturase (encoded by the gene crtI). Lycopene cyclase (encoded by the gene crtY) converts lycopene to β-carotene. β-carotene is converted to zeaxanthin via a hydroxylation reaction resulting from the activity of β-carotene hydroxylase (encoded by the crtZ gene). These examples are not limiting and many other carotenoid genes and products (e.g., crtX, crtW/O/bkt, crtZ) exist within this $C_{40}$ lower carotenoid biosynthetic pathway. For example, β-carotene can be converted to canthaxanthin by β-carotene ketolases encoded by crtW, bkt or crtO genes. Canthaxanthin can be converted to astaxanthin by β-carotene hydroxylase encoded by the crtZ gene, and zeaxanthin can be converted to astaxanthin by β-carotene ketolases encoded by crtW, bkt, or crtO genes.

In *Staphylococcus aureus*, it has been determined that the first committed reaction toward $C_{30}$ carotenoid biosynthesis is the head-to-head condensation of two molecules of FPP by CrtM, forming dehydrosqualene (Wieland, B., et al., *J. Bacteriol.*, 176(24): 7719–7726 (1994)). Subsequently, dehydrosqualene desaturase (encoded by crtN) is successively dehydrogenated in three steps to produce 4,4'-diaponeurosporene (Wieland et al., supra). However, at present time public databases include only one single gene (GenBank® Accession Number X73889) and 4 genomic sequences (NC002745, NC002758, AP003137, AP003365) of crtN and crtM, isolated from *S. aureus* strains N315 and Mu50. A single report exists concerning the heterologous overexpression of crtN from *S. aureus* in *E. coli* (Raisig, A., and G. Sandmann., *J. Bacteriol.*, 181(19):6184–6187 (1999)). Based on identification of carotenoid compounds, it is known that the next stages in the $C_{30}$ metabolic pathway for *S. aureus* involve introduction of oxygen functions on the terminal methyl group to produce aldehyde and carboxylic acid forms of the carotenoid (Marshall, J. H., and G. J. Wilmoth., *J. Bacteriol.*, 147: 900–913 (1981) and *J. Bacteriol.*, 147: 914–919 (1981); U.S. Ser. No. 10/860,291; hereby incorporated by reference).

Expression of Carotenoid Biosynthetic Pathway Genes

The carotenoid biosynthesis genes expressed in the exemplified microorganisms are various combinations of crt genes used to produce $C_{30}$ or $C_{40}$ carotenoids. In one embodiment, the crt genes produce $C_{40}$ carotenoids. Recombinant expression of genes in the lower carotenoid biosynthetic pathway is well known in the art. In one aspect, examples of suitable $C_{40}$ crt genes for use in the present invention include, but are not limited to crtE, crtB, crtI, crtY, crtZ and crtX (genes isolated from *Pectobacterium cypripedii*, as described by Cheng et al. in copending U.S. Ser. No. 10/804,677, incorporated herein by reference; crtE, crtB, crtI, crtY, crtZ and crtX genes isolated from a member of the Enterobacteriaceae family, as described by Cheng et al. in copending U.S. Ser. No. 10/808,979, incorporated herein by reference; crtE, idi, crtB, crtI, crtY, crtZ genes isolated from *Pantoea agglomerans*, as described by Cheng et al. in copending U.S. Ser. No. 10/808,8073, incorporated herein by reference; and crtE, idi, crtB, crtI, crtY, crtZ and crtX genes isolated from *Pantoea stewartii*, as described by Cheng et al. in copending U.S. Ser. No. 10/810,733, incorporated herein by reference).

Microbial expression systems and expression vectors containing regulatory sequences that direct high level expression of foreign proteins are well known to those skilled in the art. Any of these could be used to construct chimeric genes for production of a variety of gene products. These chimeric genes could then be introduced into the optimized hosts of the present invention via transformation to provide high level expression of the required enzymes.

Vectors or cassettes useful for the transformation of the optimized hosts of the present invention are well known in the art. Typically the vector or cassette contains sequences directing transcription and translation of the relevant gene(s), a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the desired ORFs in the optimized host cells of the present invention are numerous and familiar to those skilled in the art. Virtually any promoter capable of driving the desired genes is suitable for the present invention including, but not limited to: CYC1, HIS3, GAL1, GAL10, ADH1, PGK, PHO5, GAPDH, ADC1, TRP1, URA3, LEU2, ENO, TPI, AOX1, lac, ara, tet, trp, $IP_L$, $IP_R$, T7, tac, trc, amy, apr, hps, npr and various phage promoters. Additionally, the deoxy-xylulose phosphate synthase or methanol dehydrogenase operon promoter (Springer et al., *FEMS Microbiol Lett*, 160:119–124 (1998)), the promoter for polyhydroxyalkanoic acid synthesis (Foellner et al., *Appl. Microbiol. Biotechnol.*, 40:284–291 (1993)), promoters identified from native plasmids in methylotrophs (EP 296484), Plac (Toyama et al., *Microbiology*, 143:595–602 (1997); EP 62971), Ptrc (Brosius et al., *Gene*, 27:161–172 (1984)), and promoters associated with antibiotic resistance [e.g., kanamycin (Springer et al., *FEMS Microbiol Lett*, 160:119–124 (1998); Ueda et al., *Appl. Environ. Microbiol.*, 57:924–926 (1991)), tetracycline (U.S. Pat. No. 4,824,786) or chloramphenicol] are suitable for expression in a variety of microbial host cells. Promoters endogenous to *Methylomonas* sp. 16a have been reported (U.S. Ser. No. 10/689,200; hereby incorporated by reference).

It is necessary to include an artificial ribosomal binding site ("RBS") upstream of a gene to be expressed, when the RBS is not provided by the vector. This is frequently required for the second, third, etc. gene(s) of an operon to be expressed, when a single promoter is driving the expression of a first, second, third, etc. group of genes. Methodology to determine the preferred sequence of a RBS in a particular host organism will be familiar to one of skill in the art, as are means for creation of this synthetic site.

Termination control regions may also be derived from various genes native to the preferred hosts. Optionally, a termination site may be unnecessary; however, it is most preferred if included.

Merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: 1.) the nature of the relevant transcriptional promoter and terminator sequences; 2.) the strength of the ribosome binding site; 3.) the number of copies of the cloned gene and whether the gene is plasmid-borne or integrated into the genome of the host cell; 4.) the final cellular location of the synthesized foreign protein; 5.) the efficiency of translation in the host organism; 6.) the intrinsic stability of the cloned gene protein within the host cell; and 7.) the codon usage within the cloned gene, such that its frequency approaches the frequency of preferred codon usage of the host cell.

Transformation of Methylotrophic Bacteria

A preferred host for use in the present invention are the methylotrophs and the methanotrophs having the ability to use either methane or methanol as a sole carbon source. These organisms are have certain energetic advantages for the production of carotenoid compounds but also have some specific requirements with respect to genetic manipulation and transformation.

Electroporation has been used successfully for the transformation of: *Methylobacterium extorquens* AM1 (Toyama, H., et al., *FEMS Microbiol. Lett.*, 166:1–7 (1998)), *Methylophilus methylotrophus* AS1 (Kim, C. S., and T. K. Wood, *Appl. Microbiol. Biotechnol.*, 48:105–108 (1997)), and *Methylobacillus* sp. strain 12S (Yoshida, T., et al., *Biotechnol. Lett.*, 23: 787–791 (2001)).

Bacterial conjugation, relying on the direct contact of donor and recipient cells, is frequently more readily amenable for the transfer of genes into methylotrophic bacteria. Simplistically, this bacterial conjugation process involves mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

1. In some cases, only a donor and recipient are required for conjugation. This occurs when the plasmid to be transferred is a self-transmissible plasmid that is both conjugative and mobilizable (i.e., carrying both tra genes and genes encoding the Mob proteins). In general, the process involves the following steps: 1.) Double-strand plasmid DNA is nicked at a specific site in oriT; 2.) A single-strand DNA is released to the recipient through a pore or pilus structure; 3.) A DNA relaxase enzyme cleaves the double-strand DNA at oriT and binds to a released 5' end (forming a relaxosome as the intermediate structure); and 4.) Subsequently, a complex of auxiliary proteins assemble at oriT to facilitate the process of DNA transfer.
2. Alternatively, a "triparental" conjugation is required for transfer of the donor plasmid to the recipient. In this type of conjugation, donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins; however, the Mob proteins alone are not sufficient to achieve the transfer of the genome. Thus, mobilizable plasmids are not able to promote their own transfer unless an appropriate conjugation system is provided by a helper plasmid (located within the donor or within a "helper" cell). The conjugative plasmid is needed for the formation of the mating pair and DNA transfer, since the plasmid encodes proteins for transfer (Tra) that are involved in the formation of the pore or pilus.

Examples of successful conjugations involving methylotrophic bacteria include the work of: Stolyar et al. (*Mikrobiologiya*, 64(5): 686–691 (1995)); Motoyama, H. et al. (*Appl. Micro. Biotech.*, 42(1): 67–72 (1994)); Lloyd, J. S. et al. (*Archives of Microbiology*, 171(6): 364–370 (1999)); and Odom, J. M. et al. (U.S. Ser. No. 09/941,947).

Industrial Production Methodologies

The present invention describes the construction of a carotenogenic host having a disruption in the gene encoding glycogen synthase. Such hosts have shown and enhanced ability to make carogenoid compounds and are referred to herein as high flux carotenogenic hosts.

For commercial production of the desired product, e.g., $C_{40}$ carotenoids, using a high flux carotenogenic host, a variety of culture methodologies may be applied. For example, large-scale production of a specific gene product overexpressed from the carotenogenic microorganisms may be produced by batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur while adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Real time measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in *Biotechnology: A Textbook of Industrial Microbiology*, $2^{nd}$ ed. (1989) Sinauer Associates: Sunderland, Mass., or Deshpande, Mukund V., *Appl. Biochem. Biotechnol.*, 36:227 (1992).

Commercial production of the desired product, e.g., carotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art of industrial microbiology and a variety of methods are detailed by Brock, supra.

Fermentation media in the present invention must contain suitable carbon substrates. Suitable substrates may include, but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane and/or methanol for which metabolic conversion into key biochemical intermediates has been demonstrated (U.S. Ser. No. 09/941,947). In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.*, 153:485–489 (1990)). Hence, it is contemplated that the source of carbon utilized in the present invention may encompass a wide variety of carbon containing substrates and will only be limited by the choice of organism.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); by T. J. Silhavy, M. L. Bennan, and L. W. Enquist, *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "sec" means second(s), "min" means minute(s), "hr" means hour(s), "d" means day(s), "µL" means microliter(s), "mL" means milliliter(s), "L" means liter(s), "µM" means micromolar, "mM" means millimolar, "M" means molar, "mmol" means millimole(s), "µmol" mean micromole(s), "nmol" means nanomole(s), "g" means gram(s), "µg" means microgram(s), "ng" means nanogram(s), "nm" means nanometers, "U" means unit(s), "ppm" means parts per million, "bp" means base pair(s), "rpm" means revolutions per minute, "kB" means kilobase(s), "g" means the gravitation constant, "~" means approximately, "$OD_{600}$" means the optical density measured at 600 nm, "$OD_{260}/OD_{280}$" means the ratio of the optical density measured at 260 nm to the optical density measured at 280 nm, and "mAU" means milliabsorbance units.

Molecular Biology Techniques:

Methods for agarose gel electrophoresis were performed as described in Maniatis (supra). Polymerase Chain Reactions (PCR) techniques were found in White, B., *PCR Protocols: Current Methods and Applications*, Humana: Totowa, N.J. (1993), Vol. 15.

Media and Culture Conditions:

General materials and methods suitable for the maintenance and growth of bacterial cultures are found in: *Experiments in Molecular Genetics* (Jeffrey H. Miller), Cold Spring Harbor Laboratory: Cold Spring Harbor, N.Y. (1972); *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds.), American Society for Microbiology: Washington, D.C., pp 210–213; or in Brock, supra.

All reagents, materials, and equipment were obtained from one or more of the following sources: Aldrich Chemicals (Milwaukee, Wis.), BD Diagnostic Systems (Sparks, Md.), Invitrogen Corp. (Carlsbad, Calif.), Qiagen (Valencia, Calif.), Epicentre (Madison, Wis.), New England Biolabs (Beverly, Mass.), USB Corp. (Cleveland, Ohio), Applied Biosystems (Foster City, Calif.), Perkin Elmer (Boston, Mass.), Kendro Lab Products (Newtown, Conn.), Corning (Acton, Mass.), Gelman/Pall Life Science (Ann Arbor, Mich.), or Sigma Chemical Company (St. Louis, Mo.), unless otherwise specified.

Example 1

Growth of *Methylomonas* Sp. 16a

Example 1 summarizes the standard conditions used for growth of *Methylomonas* sp. 16a (ATCC# PTA-2402) and derivatives thereof, as described in U.S. Pat. No. 6,689,601; hereby incorporated by reference.

*Methylomonas* Strain and Culture Media

The growth conditions described below were used throughout the following experimental Examples for treatment of *Methylomonas* sp., unless conditions were specifically described otherwise.

*Methylomonas* sp. was typically grown in serum stoppered Wheaton bottles (Wheaton Scientific; Wheaton, Ill.) using a gas/liquid ratio of at least 8:1 (i.e., 20 mL of ammonium liquid "BTZ" growth medium in a Wheaton bottle of 160 mL total volume). The composition of the BTZ growth medium is given below. The standard gas phase for cultivation contained 25% methane in air, although methane concentrations can vary ranging from about 5–50% by volume of the culture headspace. These conditions comprise growth conditions and the cells are referred to as growing cells. In all cases, the cultures were grown at 30° C. with constant shaking in a rotary shaker (Lab-Line, Barnstead/Thermolyne; Dubuque, Iowa) unless otherwise specified.

BTZ Media for *Methylomonas* sp.

*Methylomonas* 16a typically grows in a defined medium composed of only minimal salts; no organic additions such as yeast extract or vitamins are required to achieve growth. This defined medium known as BTZ medium (also referred to herein as "ammonium liquid medium") consisted of various salts mixed with Solution 1, as indicated in Tables 3 and 4. Alternatively, the ammonium chloride was replaced with 10 mM sodium nitrate to give "BTZ (nitrate) medium", where specified. Solution 1 provides the composition for a 100-fold concentrated stock solution of trace minerals.

TABLE 3

Solution 1*

|  | Molecular Weight | Conc. (mM) | g per L |
|---|---|---|---|
| Nitriloacetic acid | 191.10 | 66.90 | 12.80 |
| $CuCl_2 \times 2H_2O$ | 170.48 | 0.15 | 0.0254 |
| $FeCl_2 \times 4H_2O$ | 198.81 | 1.50 | 0.30 |
| $MnCl_2 \times 4H_2O$ | 197.91 | 0.50 | 0.10 |
| $CoCl_2 \times 6H_2O$ | 237.90 | 1.31 | 0.312 |
| $ZnCl_2$ | 136.29 | 0.73 | 0.10 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.70 | 0.77 | 0.184 |

*Mix the gram amounts designated above in 900 mL of $H_2O$, adjust to pH = 7.0, and add $H_2O$ to a final volume of 1 L. Keep refrigerated.

TABLE 4

Ammonium Liquid Medium (BTZ)**

|  | MW | Conc. (mM) | g per L |
|---|---|---|---|
| $NH_4Cl$ | 53.49 | 10 | 0.537 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7.0) | 238.3 |  | 50 mL |
| Solution 1 |  |  | 10 mL |

**Dissolve in 900 mL $H_2O$. Adjust to pH = 7.0, and add $H_2O$ to give a final volume of 1 L. For agar plates: Add 15 g of agarose in 1 L of medium, autoclave, cool liquid solution to 50° C., mix, and pour plates.

Example 2

Construction of a Positive-Selection Suicide Vector

The construction of chromosomal mutations within the *Methylomonas* or *E. coli* genome was accomplished through the use of suicide vectors. Thus, a modified version of the conditional replication vector pGP704 was created, comprising a npr-sacB cassette (SEQ ID NO: 1). Preparation of the pGP704-sacB integration vector backbone has previously been described (U.S. Ser. No. 10/997,844; hereby incorporated by reference).

pGP704 as a Vector Backbone for Use as a Chromosomal Integration Vector.

The plasmid pGP704 (Miller and Mekalanos, *J. Bacteriol.*, (170): 2575–2583 (1988); FIG. 3) was chosen as a suitable vector backbone for use as a chromosomal integration vector for *Methylomonas* sp. 16a and *E. coli* MC1061, since it could be used as a vehicle to transfer replacement nucleotide sequences of interest (re-NSI) via conjugation. Plasmid pGP704 is a derivative of pBR322 that is $Amp^R$ (ampicillin resistance) but has a deletion of the pBR322 origin of replication (oriE1). Instead, the plasmid contains a cloned fragment containing the origin of replication of plasmid R6K. The R6K origin of replication (oriR6K) requires the Π protein, encoded by the pir gene. In *E. coli*, the Π protein can be supplied in trans by a prophage (λ pir) that carries a cloned copy of the pir gene. The pGP704 plasmid also contains a 1.9 kB BamHI fragment encoding the mob region of RP4. Thus, pGP704 can be mobilized into recipient strains by transfer functions provided by a derivative of RP4 integrated in the chromosome of *E. coli* strain SM10 or SY327. Once the plasmid is transferred, however, it is unable to replicate in recipients that lack the Π protein. This inability permits homologous recombination to occur between the replacement nucleotide sequences of interest (re-NSI) inserted on pGP704 and the intact chromosomal nucleotide sequences of interest (chr-NSI).

Thus, on the basis of the above characteristics, the pGP704 vector backbone met the following conditions for a chromosomal integration vector suitable for methylotrophic bacteria: 1.) it was conditional for replication, thus allowing selection for integration into the chromosome; 2.) it possessed at least one selectable marker; 3.) it had an origin of transfer that was expected to be suitable for the exemplified bacteria; 4.) it possessed mobilization genes; and 5.) it contained a variety of unique cloning sites. Other alternative chromosomal integration vectors having the characteristics listed above are expected to be suitable for use in the present invention, as described herein.

Plasmid pGP704 does not, however, permit easy detection and identification of clones that had undergone allelic exchange. Thus, pGP704 was modified to permit the positive selection of double-crossover events within exemplified bacteria.

Cloning of the npr-sacB Cassette

Plasmid pBE83 contained a *Bacillus amyloliquifaciens* sacB gene under the control of the neutral protease (npr) promoter (gift from V. Nagarajan, E. I. du Pont de Nemours and Co., Inc., Wilmington, Del.). The npr-sacB cassette (SEQ ID NO: 1) was PCR amplified from pBE83 using DNA primers DrdI/npr-sacB and TthIII/npr-sacB. The DNA primers were constructed to include unique restriction sites at each terminus of the PCR product to facilitate subsequent cloning (as indicated by the underlined sequences below):

```
DrdI/npr-sacB:                          (SEQ ID NO:2)
5'-GACATCGATGTCGAATTCGAGCTCGGTACCGATC-3'

TthIII/npr-sacB:                        (SEQ ID NO:3)
5'-GACCTCGTCGCTGTTATTAGTTGACTGTCAGC-3'
```

The PCR reaction mixture was composed of the following: 10 μL of 10×PCR buffer; 16 μL (4 μL each) of dNTPs (320 mM stock); 1 μL of *Methylomonas* chromosomal DNA solution (~500 ng/μL); 8 μL of MgCl$_2$ solution (25 mM); 0.5 μL of Taq polymerase (5 U/μL); 1 μL of DrdI/npr-sacB primer (~36 nmol); 1 μL of TthIII/npr-sacB primer (~35 nmol); and 71 μL of sterile deionized water (NANOpure® Water System, Barnstead International, Dubuque, Iowa). The PCR protocol was then performed on a 9600 Gene-Amp® PCR System (Perkin Elmer, Boston, Mass.), according to the thermocycling parameters below:

1 cycle: 94° C. (5 min);
1 cycle: 94° C. (5 min), 60° C. (2 min), 72° C. (3 min);
35 cycles: 94° C. (1 min), 60° C. (2 min), 72° C. (3 min);
1 cycle: 94° C. (1 min), 60° C. (2 min), 72° C. (10 min); and
Hold −4° C.

Afterward, the PCR product was ligated into the pCR®2.1-TOPO® vector per the manufacturer's instructions (Invitrogen; Carlsbad, Calif.). The ligation mixture was transformed into *E. coli* TOP10 One Shot® calcium chloride competent cells and transformants were screened as recommended by Invitrogen.

Plasmid DNA was isolated from positive clones (white colonies in a blue/white screen) using the QIAprep® Spin Mini-prep Kit (Qiagen; Valencia, Calif.) and the DNA was digested according to the manufacturer's instructions with restriction endonucleases DrdI and TthIII (New England Biolabs; Boston, Mass.). Initially, this PCR product was to be inserted into pGP704 digested with DrdI and TthIII; however, there were difficulties in cloning the DrdI/TthIII PCR product.

A modified cloning strategy was adopted, such that the PCR reaction described above was "repeated" using the Pfu DNA polymerase (Stratagene; La Jolla, Calif.). Specifically, the PCR reaction and protocol were performed exactly as described above, with the exception that Pfu polymerase and buffers from Stratagene were used. A PCR product having flush or blunt ends was produced. This PCR product was ligated directly into the XcaI site of pGP704 (FIG. 3). The ligation mixture was transformed into calcium chloride competent *E. coli* SY327 cells (Miller, V. L. and Mekalanos, J. J., *Proc. Natl. Acad. Sci.*, 81(11):3471–3475 (1984)).

The transformants were screened using the DrdI/npr-sacB and TthIII/npr-sacB PCR primers (SEQ ID NOs: 2 and 3, respectively) to identify vectors containing the npr-sacB insert. The PCR products were analyzed on a 0.8% agarose gel. Plasmid DNA was isolated from cells containing the pGP704::sacB vector (SEQ ID NO: 4).

Theory of the Conjugation

The mobilization of vector DNA into *Methylomonas* or *E. coli* MC1061 occurs through conjugation (tri-parental mating). The pGP704::sacB vector used to make chromosomal mutations has a R6K origin of replication, which requires the Π protein. This vector can replicate in *E. coli* strain SY327, which expresses the Π protein. However, this protein is not present in the *Methylomonas* or *E. coli* MC1061 genome. Therefore, once the vector DNA has entered into the recipient cell, it is unable to duplicate itself. If the vector also contains a DNA segment that shares homology to a region of the recipient cell's genome, the vector can be integrated into the host's genome through homologous recombination.

In the case of *Methylomonas* and *E. coli* MC1061, the mobilizable plasmid (pGP704::sacB) was used to transfer the re-NSI into these bacteria. The conjugative plasmid (pRK2013; ATCC No. 37159), which resided in a strain of *E. coli*, facilitated the DNA transfer.

Growth of *Methylomonas* sp.

The growth of *Methylomonas* sp. MWM1200 and *Methylomonas* sp. MWM1500, both derivatives of *Methylomonas* sp. 16a (ATCC PTA-2402), was initiated with the inoculation of a −80° C. frozen stock culture into 20 mL of BTZ medium containing 25% methane, as described in Example 1.

*Methylomonas* sp. MWM1200 was created by disrupting expression of genes involved in C$_{30}$ carotenoid production (i.e. crtN1, ald, crtN2, and crtN3), thereby creating an optimized host cell suitable for engineering C$_{40}$ carotenoid biosynthesis (U.S. Ser. No. 10/997,844). *Methylomonas* MWM1200 is comprised of a wild type glycogen synthase gene (glgA), capable of producing significant amounts of glycogen (up to about 55% dry cell weight).

The culture was grown at 30° C. with aeration until the density of the culture was saturated. This saturated culture was in turn used to inoculate 100-mL of fresh BTZ medium containing 25% methane. The 100-mL culture was grown at 30° C. with aeration until the culture reached an OD$_{600}$ between 0.7 to 0.8. To prepare the cells for the tri-parental mating, the *Methylomonas* sp. cells were washed twice in an equal volume of BTZ medium. The *Methylomonas* cell pellets were re-suspended in the minimal volume needed (approximately 200 to 250 μL). Approximately 40 μL of the re-suspended Methylomonas cells were used in each tri-parental mating experiment.

Preparation of the Astaxanthin Expression Plasmid pDCQ343

The astaxanthin expression plasmid pDCQ343 (SEQ ID NO: 5) was prepared by cloning into pBHR1 (MoBiTec GmbH, Goettingen, Germany) the crtW ketolase from *Sphingomonas melonis* DC18 (U.S. Ser. No. 11/015,433; hereby incorporated by reference; SEQ ID NO: 6) and the crtZ carotenoid hydroxylase (U.S. 60/601,947; SEQ ID NO: 7) from *Brevundimonas vesicularis* DC263 upstream of the crtEYIB gene cluster from Enterobacteriaceae DC260 (U.S. Ser. No. 10/808,979; hereby incorporated by reference). The resulting gene cluster, crtWZEYIB was operably linked to the chloramphenicol resistance promoter (Pcat) found on pBHR1.

Growth of the *Escherichia Coli* Donor and Helper Cells

Isolated colonies of the *E. coli* donor (pGP704::sacB::re-NSI) and helper (containing conjugative plasmid pRK2013) cells were used to inoculate 5 mL of LB broth containing 25 μg/mL Kan; these cultures were grown overnight at 30° C. with aeration. The following day, the *E. coli* donor and helper cells were mixed together and incubated at 30° C. for ~2 hours. Subsequently, the cells were washed twice in equal volumes of fresh LB broth to remove the antibiotics.

Tri-parental Mating: Mobilization of the Donor Plasmid into *Methylomonas* Strain MWM1200

Approximately 40 μL of the re-suspended *Methylomonas* cells were used to re-suspend the combined *E. coli* donor and helper cell pellets. After thoroughly mixing the cells, the cell suspension was spotted onto BTZ agar plates containing 0.05% yeast extract. The plates were incubated at 30° C. for 3 days in a jar containing 25% methane.

Following the third day of incubation, the cells were scraped from the plate and re-suspended in BTZ broth. The entire cell suspension was plated onto several BTZ agar plates containing Amp[35]. The plates were incubated at 30° C. in a jar containing 25% methane until colonies were visible (~4–7 days).

Individual colonies were streaked onto fresh BTZ+Amp[35] agar plates and incubated 1–2 days at 30° C. in the presence of 25% methane. These cells were used to inoculate bottles containing 20 mL of BTZ and 25% methane. After overnight growth, 5 mL of the culture was concentrated by centrifugation using a tabletop centrifuge. Then, to rid the cultures of *E. coli* cells that were introduced during the tri-parental mating, the cells were inoculated into 20 mL of BTZ liquid medium containing nitrate (10 mM) as the nitrogen source, methanol (200 mM), and 25% methane and grown overnight at 30° C. with aeration. Cells from the BTZ (nitrate) cultures were again inoculated into BTZ and 25% methane and grown overnight at 30° C. with aeration. The cultures were monitored for *E. coli* growth by plating onto LB agar plates to verify the success of the *E. coli* elimination.

Example 3

PCR Amplification and Cloning of the *Methylomonas* glgA DNA Fragments into pGP704::sacB For amplification of the subsequent PCR fragments [glgA deletion fragment #1 (~1.2 kb; SEQ ID NO: 8) and glgA deletion fragment #2 (~1.1 kb; SEQ ID NO: 9), the following DNA primers (Table 5) were used. The PCR reaction mixture was composed of the following: 5 μL of 10× MasterAmp™ Taq PCR buffer (Epicentre® Biotechnologies, Madison, Wis.); 4 μL (1 μL each) of dNTPs (10 mM stock); 1 μL of *Methylomonas* 16a (ATCC PTA-2402) chromosomal DNA solution (~500 ng/μL); 4 μL of $MgCl_2$ solution (25 mM); 15 μL MasterAmp™ 10×PCR Enhancer (3× final concentration), 0.25 μL MasterAmp™ Taq DNA Polymerase (5 U/μL) (Epicentre®), 1 μL of each primer pair [BglII/glgA (deletion) #1 (SEQ ID NO: 10)+XbaI, SpeI, MluI/glgA (deletion) #1 (SEQ ID NO: 11) or MluI, SpeI/glgA (deletion) #2 (SEQ ID NO: 12)+XbaI/glgA (deletion) #2 (SEQ ID NO: 13)], and sterile water (added to achieve a final volume of 50 μL). The PCR protocol was performed using a GeneAmp® PCR 9600 System (Perkin Elmer, Boston, Mass.), according to the thermocycling parameters below:

1 cycle: 95° C. (5 min);
30 cycles: 94° C. (15 sec), 60° C. (30 sec), 72° C. (30 sec)
1 cycle: 72° C. (6 min)

The PCR products were analyzed on a 0.8% agarose gel. As expected, an 1.2 kB DNA fragment was generated for the glgA deletion fragment #1 and an 1.1 kB generated for the glgA deletion fragment #2.

Fresh PCR products were cloned using the TOPO® TA Cloning® Kit (Invitrogen). The TOPO® reaction mixture contained 4 μL fresh PCR product, 1 μL Salt solution (from TOPO® TA Cloning® Kit), and 1 μL TOPO® vector (pCR®2.1), which was incubated at room temperature for 30 minutes. *E. coli* TOP10 ™ cells were transformed with 2 μL of the TOPO reaction mixture. A blue/white screen was used to identify insert-containing vectors. Eight white colonies were evaluated for glgA deletion fragment #1 and glgA deletion fragment #2 using a similar PCR method as described above. However the PCR protocol was done using the thermocycling parameters below:

1 cycle: 95° C. (5 min);
30 cycles: 95° C. (15 sec), 60° C. (30 sec), 72° C. (30 sec);
1 cycle: 72° C. (6 min)

The PCR products were evaluated on an 0.8% agarose gel. The insert was correct for all eight plasmids containing glgA deletion fragment #1 and was correct for seven out of the eight plasmids containing glgA deletion fragment #2. Plasmid mini-preps were done using the QIAquick® Spin Mini-preps (Qiagen). The plasmid DNA was eluted into 50 μL EB buffer (found in the QIAquick® Spin Mini-preps kit).

The glgA deletion fragment #1 and glgA deletion fragment #2 were excised from the TOPO® vector via digestions with restriction endonucleases (New England Biolabs, Beverly, Mass.). The glgA deletion fragment #1 was released from the TOPO® vector through digestion with EcoRI and the glgA deletion fragment #2 was acquired by digestion with BglII and XbaI. The DNA fragments were separated on a 0.8% agarose gel and the desired fragments were excised and the DNA was extracted using a QIAquick® Gel Extraction Kit (Qiagen). The EcoRI digested glgA deletion fragment #1 was subsequently digested with BglII and XbaI. Following the clean-up of the glgA deletion fragment #1 using the QIAquick® Gel Extraction Kit (Qiagen), the BglII/XbaI digested glgA deletion fragment #1 insert DNA was ligated with the BglII/XbaI digested pGP704-sacB vector DNA. The ligation reaction was performed using Fast-Link™ DNA ligase (Epicentre) which was incubated for ~4 hours in a water bath heated to room temperature. The ligation reaction was terminated by heat-inactivation of the ligase for 15 minutes at 70° C. and was used to transformed calcium chloride competent *E. coli* SY327 cells. The transformation mixture was plated onto LB+ampicillin (Amp[50]) (50 μg/mL) and several colonies were picked, grown in 10 mL of liquid LB+Amp[50] broth, and plasmid DNA was purified from cells the same as described previously.

The plasmid DNA was evaluated by restriction digestion with BglII and XbaI. As expected, colonies having vector+insert DNA (pGP704-sacB+glgA deletion fragment #1) produced two bands upon digestion that were 5.4 kB and 1.2 kB in size. The pGP704-sacB+glgA deletion fragment #1 was subsequently digested with MluI for ~3 hours at 37° C. followed by addition of XbaI and the digestion reaction continued for an additional hour. The dephosphorylation reaction was carried out in the digestion buffer by the addition of Shrimp Alkaline Phosphatase (E.C. 3.1.3.1; USB Corp., Cleveland, Ohio) and further incubation for 45 minutes at 37° C. The dephosphorylation reaction was terminated by heat-inactivation at 65° C. for 15 minutes. Afterward, the reaction was run on a 0.8% agarose gel, a 6.5 kB DNA fragment was excised and purified as described above. The dephosphorylated MluI/XbaI digested pGP704-sacB+glgA deletion fragment #1 vector DNA was ligated to the MluI/XbaI digested glgA deletion fragment #2, using the same ligation conditions described above. Next, the ligation reaction was heat-inactivated at 70° C. for 15 minutes and was used to transform calcium chloride competent *E. coli* SY327 cells. Colonies growing on LB+Amp[50] plates were grown in liquid medium for plasmid isolation. The plasmid DNA was purified the same as described above. Enzymatic digestion reactions were done with BglII and XbaI to identify pGP704-sacB vectors that contained both insert DNA fragments (glgA deletion fragment #1 and glgA deletion fragment #2). Seven out the eight DNA samples evaluated had both insert fragments. DNA samples containing the correct insert DNA produced two DNA fragments when digested with BglII and XbaI; the DNA fragment were 5.4 kB and 2.2 kB in size.

In vitro transposition was used (Epicentre's EZ::TN™ <KAN-2> insertion kit) to inactivate the ampicillin resistance gene that was present in the pGP704-sacB+glgA deletion fragment #1+glgA deletion fragment #2 vector for the kanamycin (Kan) resistance gene that was present on the EZ::TN™ <Kan-2> transposable element. The transposition reaction was carried out as described in the manufacturer's protocol (Epicentre). The transposition mixture was used to transform calcium chloride competent E. coli SY327 cells which were plated onto LB+Kan$^{50}$ (50 μg/mL) agar plates. Approximately 80 colonies were selected agar and patched onto fresh LB+Kan$^{50}$ and LB+Amp$^{50}$ agar plates. After overnight incubation at 37° C., cells that were unable to grow on the LB+Amp$^{50}$ agar plates were streaked for isolated colonies. The positive vectors (pGP704::sacB:: ΔglgA; SEQ ID NO: 14) were used as the donor cells in triparental mating experiments with Methylomonas.

washed twice in an equal volume of BTZ medium. The Methylomonas cell pellets were re-suspended in a minimal volume (approximately 200 to 250 μL). Approximately 40 μL of the resuspended Methylomonas cells were used in each tri-parental mating experiment.

Growth of the Escherichia Coli Donor and Helper Cells

Isolated colonies of the E. coli donor (pGP704::sacB:: ΔglgA) and helper (containing conjugative plasmid pRK2013) cells were used to inoculate 5 mL of LB broth containing 25 μg/mL Kan; these cultures were grown overnight at 30° C. with aeration. The following day, the E. coli donor and helper cells were mixed together and incubated at 30° C. for ~2 hr. Subsequently, the cells were washed twice in equal volumes of fresh LB broth to remove the antibiotics.

Tri-parental Mating: Mobilization of the Donor Plasmid into Methylomonas

Approximately 80 μL of the resuspended Methylomonas cells were used to re-suspend the combined E. coli donor and helper cell pellets. After thoroughly mixing the cells, the cell suspension was spotted onto BTZ agar plates containing

TABLE 5

PRIMERS UTILIZED FOR CLONING
THE METHYLOMONAS glgA DELETION DNA FRAGMENTS

| Deletion Fragment | Forward Primer | Reverse Primer | Size of PCR Fragment |
|---|---|---|---|
| glgA deletion fragment #1 | BglII/glgA (deletion) #1 5'-AGATCTTGACCGGT TGAAATAAGTCG-3' (SEQ ID NO: 10) | XbaI, SpeI, MluI/glgA(deletion) #1 5'-TCTAGAACTAGTACG CGTGAGCGGATTCG TCTTCAACG-3' (SEQ ID NO: 11) | 1.2 kB |
| glgA deletion fragment #2 | MluI, SpeI/glgA (deletion) #2 5'-ACGCGTACTAGTCA TCAAGGGATGGGTT TCGC-3' (SEQ ID NO: 12) | XbaI/glgA (deletion) #2 5'-TCTAGACTTCTGGCT GGAAGATTCC-3' (SEQ ID NO: 13) | 1.1 kB |

**Underlined sequences represent restriction endonuclease recognition sites.

Example 4

Tri-Parental Conjugation of the glgA Integration Vector into Methylomonas sp. 16A The pGP704::sacB::ΔglgA vector from Example 3 was transferred into Methylomonas sp. MWM1200 via triparental conjugation. Specifically, the following strains were used as recipient, donor, and helper, respectively: Methylomonas sp. MWM1200, E. coli SY327 containing the glgA integration vector, and E. coli containing pRK2013 (ATCC No. 37159).

Growth of Methylomonas sp.

The growth of Methylomonas sp. MWM1200 for tri-parental mating was initiated with the inoculation of an −80° C. frozen stock culture into 20 mL of BTZ medium containing 25% methane, as described in Example 1. The culture was grown at 30° C. with aeration until the density of the culture was saturated. This saturated culture was in turn used to inoculate 100 mL of fresh BTZ medium containing 25% methane. The 100 mL culture was grown at 30° C. with aeration until the culture reached an OD$_{600}$ between 0.7 to 0.8. To prepare the cells for the tri-parental mating, the Methylomonas sp. MWM1200 cells were 0.05% yeast extract. The plates were incubated at 30° C. for 3 days in a jar containing 25% methane.

Following the third day of incubation, the cells were scraped from the plate and re-suspended in 300 μL BTZ broth. The entire cell suspension was plated onto several BTZ agar plates containing Kan$^{25}$. The plates were incubated at 30° C. in a jar containing 25% methane until colonies were large enough to be re-streaked (~10 days) onto fresh BTZ+Kan$^{25}$ medium.

Twelve colonies were streaked onto fresh BTZ+Kan$^{25}$ agar plates and incubated for several days at 30° C. in the presence of 25% methane. The cells from different streaks were used to inoculate three 160 mL bottles containing 20 mL BTZ+Kan$^{25}$. The cells were grown to saturation and 0.5 mL was used to inoculate BTZ only liquid medium for three successive passages. Afterwards, dilutions ($10^{-3}$, $10^{-4}$, $10^{-5}$, $10^{-6}$) were made and plate onto BTZ+5% sucrose agar plates. Approximately 50 colonies were patched onto BTZ+Kan$^{25}$ and then BTZ alone agar plates. The cultures that were able to grow only on the BTZ medium were further evaluated using PCR methodology to determine if the second crossover event resulted in the deletion of glgA or if the second crossover event regenerated the wild-type Methylomonas glgA gene (SEQ ID NO: 15). The PCR reaction mixture was composed of the following components: MasterAmp™ Taq 10×PCR buffer [Epicentre®] (5 µL), 25 mM MgCl$_2$ (4 µL), MasterAmp™ 10×PCR Enhancer [Epicentre®] (15 µL), 1 ∆L each of [dATP, dCTP, dGTP, dTTP (Applied Biosystems, Foster City, Calif.), BglII/glgA deletion primer #1 and XbaI/glgA deletion primer #2], 0.25 µL MasterAmp™ Taq DNA Polymerase (Epicentre®) and 0.5 µL *Methylomonas* chromosomal DNA solution (~500 ng/µL). The PCR protocol was carried out using GeneAmp® PCR 9600 System (Perkin Elmer), consistence with the thermocycling parameters below:

1 cycle: 94° C. (5 min);
1 cycle: 94° C. (5 min), 60° C. (2 min), 72° C. (3 min);
35 cycles: 94° C. (1 min), 60° C. (2 min), 72° C. (3 min)
1 cycle: 94° C. (1 min), 60° C. (2 min), 72° C. (10 min)
Hold –4° C.

The PCR products were analyzed on a 0.8% agarose gel. The majority of the cultures produced a PCR fragment that was ~3.4 kb in size, which was consistent with the second crossover event occurring on the same side of the glgA deletion plasmid as the first crossover event (Table 6), thus the wild-type glgA gene remains unaltered. However, one culture produced a PCR fragment (~2.2 kb) which indicated that the glgA gene had been deleted.

Cells from the ∆glgA isolate (*Methylomonas* sp. MWM1500) were used to inoculate bottles containing 20 mL of BTZ and 25% methane. After overnight growth, 5 mL of the culture was concentrated by centrifugation using a tabletop centrifuge. Then, to rid the cultures of *E. coli* cells that were introduced during the tri-parental mating, the cells were inoculated into 20 mL of BTZ liquid medium containing nitrate (10 mM) as the nitrogen source, methanol (200 mM), and 25% methane and grown overnight at 30° C. with aeration. Cells from the BTZ (nitrate) cultures were again inoculated into BTZ and 25% methane and grown overnight at 30° C. with aeration. The cultures were monitored for *E. coli* growth by plating onto LB agar plates to verify the success of the *E. coli* elimination. Once the ∆glgA culture was shown to be *E. coli*-free, the effect of the glgA mutation on carotenoid synthesis was evaluated.

Donor: *E. coli* 10 G (Lucigen, Middleton, Wis.)(F$^-$ mcrA D(mrr-hsdRMS-mcrBC) f80dlacZDM15 DlacX74 endA1 recA1araD139 D(ara, leu)7697 galU galK rpsL nupG I-tonA) containing pDCQ343

Helper: *E. coli* containing the conjugation helper plasmid pRK2013

Recipients: *Methylomonas* strains MWM1200 (glgA$^+$) and MWM1500 (∆glgA)

For each mating, the saturated donor and helper cultures were combined into a single Falcon (14-mL polypropylene round-bottom) tube (Becton Dickinson Labware, Franklin Lakes, N.J.), since they had been grown in the same antibiotic and were centrifuged for 15 minutes at ~4300 rpm (Sorvall centrifuge; available from Kendro Lab Products, Newtown, Conn.)). The supernatant was discarded and the cells were washed with 4.5 mL of BTZ medium. The cells were centrifuged for a second time under the same conditions, the supernatant was removed and the cells were again re-suspended in 4.5 mL of BTZ medium and the cells were harvested as described above and the supernatant was discarded. The *E. coli* donor and helper cells were re-suspended in ~80 µL of the *Methylomonas* recipient cells (see below).

The *Methylomonas* recipient cultures were harvested by centrifugation of the cells in a 50-mL polypropylene tube (Corning Inc., Corning, N.Y.) for 15 minutes at ~4300 rpm (Sorvall centrifuge; available from Kendro Lab Products, Newtown, Conn.)). The supernatant was discarded and the cells were washed in 50 mL of BTZ medium. The cells were centrifuged for a second time under the same conditions, the supernatant was removed and the cells again re-suspended in 50 mL of BTZ medium and the cells were harvested as described above. The supernatant was discarded and the *Methylomonas* recipient cultures were re-suspended in the smallest possible volume needed (~250 µL of BTZ medium). The re-suspended *Methylomonas* recipient cells were then used to re-suspend the *E. coli* donor and helper cells (see above).

The *E. coli* donor:*E. coli* helper:*Methylomonas* recipient mixture was spotted onto BTZ+0.05% yeast extract (YE) agar plates and incubated at 30° C. for three days in an jar

TABLE 6

PRIMERS USED TO VERIFY THE DELETION OF THE
*METHYLOMONAS* MWM1200 glgA GENE

| Gene | Forward Primer | Reverse Primer | Intact Fragment | Deletion Fragment |
|---|---|---|---|---|
| glgA | Bg/II/glgA (deletion) #1 5'AGATCTTGACCGG TTGAAATAAGTCG3' (SEQ ID NO: 10) | XbaI/glgA (deletion) #2 5'TCTAGACTTCTGG CTGGAAGATTCC3' (SEQ ID NO: 13) | 3.4 kB | 2.2 kB |

**Underlined sequences represent restriction endonuclease recognition sites.

Tri-Parental Conjugation of the Astaxanthin Carotenoid Plasmid pDCQ343 into *Methylomonas* Strains MWM1200 and MWM1500

The astaxanthin reporter plasmid pDCQ343 (SEQ ID NO: 5) was mobilized into the glgA$^+$ (MWM1200) and glgA$^-$ (MWM1500) *Methylomonas* strains via triparental mating. The donor strain was grown per mating in 3 mL LB broth, the helper strains was grown per mating in 1.5 mL of LB broth and the recipient strains was grown in 100 mL of BTZ medium in a 500 mL serum bottle (Wheaton, Miliville, N.J.), each overnight in the appropriate antibiotic.

containing 25% methane. Following the third day of incubation, the cells were scraped from the plates and re-suspended in BTZ broth. The entire cell suspension was plated onto three BTZ agar plates containing 25 µg/mL kanamycin (Kan$^{50}$). The plates were incubated at 30° C. in a jar containing 25% methane until colonies were visible (~4–7 days).

Individual colonies were streaked onto fresh BTZ+Kan$^{50}$ agar plates and incubated 1–2 days at 30° C. in the presence of 25% methane. The cells were used to inoculate 1 mL of BTZ+Kan$^{50}$ and were grown overnight in a 24-well block with aeration. Approximately 25 µL of the saturated culture was used to inoculate 0.5 mL of BTZ(NO$_3$)+Kan$^{50}$+200 mM methanol liquid media, which was grown to saturation by incubation at 30° C. with aeration. To inoculate 1 mL of fresh BTZ+Kan$^{50}$ medium, 50 μL of the methanol grown culture was used. The culture was grown to saturation by incubation at 30° C. with aeration. The plates were monitored for *E. coli* contamination by plating onto LB agar plates. Following the first round of methanol growth, the LB plating revealed that *E. coli* cells were still present in the *Methylomonas* culture. The culture was again inoculated into BTZ(NO$_3$)+Kan$^{50}$+200 mM methanol liquid media. Following the second round of methanol culturing, plating onto LB agar plates revealed the *E. coli* have been eliminated.

Example 5

Analysis of C$_{40}$ Carotenoids Produced by *Methylomonas* glgA Mutant using HPLC-Photodiode Array To investigate the effect of deleting the glycogen synthase gene (glgA; SEQ ID NO: 15) on the synthesis of C$_{40}$ carotenoids, the carotenoids were extracted from the glgA$^-$ (*Methylomonas* MWM1500) strain and evaluated using high performance liquid chromatography with photodiode array detection (HPLC-photodiode array). As a control, the carotenoid from the parental strain, *Methylomonas* MWM1200, was also extracted and analyzed using similar methods.

Methanol Extraction Method

Both *Methylomonas* cultures (MWM1200 and MWM1500) were grown with aeration in two 500-mL bottles containing 100 mL of BTZ and 25% methane until they reached saturation (~24 hours). The cells were harvested by centrifugation for 15 min at 4000 rpm. The cell pellet was extracted twice with 10 mL of methanol for 15 min at room temperature with agitation. This step was followed by two extractions with 10 mL of a methanol/acetone (1:1) mixture for 15 min at room temperature also with agitation. The extracted C$_{40}$ carotenoids were dried with nitrogen and were subsequently re-dissolved in 1 mL of methanol.

THF/Methanol Extraction Method

The *Methylomonas* cultures to be analyzed were grown in two 500 mL bottles containing 100 mL of BTZ and 25% methane until saturation (~24 hr). The cells were split into two aliquots and harvested by centrifugation. For one aliquot, the cell pellets were dried in an oven at ~100° C. for ~24 hours and the dry cell mass was determined. The other aliquot was used for C$_{40}$ carotenoid extractions. The cells were lysed using glass beads (0.5 mL/sample). Also added to each sample was 150 μL of the internal standard, ethyl-β-apo-8'-carotene (trans) (100 mg/L stock solution) and 5 mL of a THF (tetrahydrofuran)/methanol (1:1) solution. This mixture was vortexed for ~2 min, followed by a 15 min centrifugation at 8,000 rpm. The supernatant was collected and the sample was vortexed again for ~2 min and centrifuged at 8,000 rpm for another 15 min. The supernatants were combined and were dried using nitrogen. The carotenoid samples were stored at –80° C. until analyzed using HPLC-photodiode array.

Analysis of Glycogen Production in *Methylomonas* Carotenoid Producing Strains

*Methylomonas* cells, glgA$^+$ (MWM1200) and glgA$^-$ (MWM1500), were prepared for glycogen determination. Approximately 30 mL of freshly collected supernatant (OD$_{600}$~10) from each reactor run was centrifuged for 15 min at 8000 rpm at 4° C. Each pellet sample was frozen on dry ice and lyophilized for 24 hours. The lyophilized sample was ground into powder. 50 mg of the powder was resuspended with 2 mL of deionized water in 25 mL glass vial. The pH of the sample was neutral. The sample was put into an aluminum crimp-sealed vial, boiled with gentle stirring for 3 minutes and then autoclaved for 40 min at 123° C. The solution was removed from the autoclave and the temperature was held at 60° C. to prevent precipitation of the sample. Deionized water was added to a total volume of 5 mL. The sample was mixed with a syringe and transferred to 15 mL conical tubes. Prior to removal of the sample for hydrolyses step, the sample was mixed by vortexing.

Starch Assay

The Starch Assay Kit, HK (catalog No. SA-20, Sigma-Aldrich, St. Louis, Mo.) was used to confirm the deletion of the *Methylomonas* glgA gene. This is a three-step enzymatic assay. In the first step, the starch is hydrolyzed to glucose by amyloglucosidase. The second step involves the phosphorylation of glucose by adenosine triphosphate, which is catalyzed by hexokinase. In the final step, glucose-6-phosphate dehydrogenase is added which catalyzed the oxidation of glucose-6-phosphate to 6-phosphogluconate in the presence of nicotinamide adenine dinucleotide (NAD). It is during the oxidation step that NAD is reduced to NADH, which causes an increase in absorbance at 340 nm and directly proportional to the concentration of glucose produced in the reaction.

In the starch assay (as per the manufacturer's protocol) half of the recommended volumes for all Sigma reagents was used. After hydrolyses, 50 μL of sample was added to a solution containing 450 μL of deionized water and 500 μL of Glucose Reagent (from the Starch Assay Kit). The hydrolyses step was done as described in the manufacturer's protocol with dilution factor 2. At Glucose Assay step (as per the manufacturer's protocol), tubes were incubated at 35° C. for 15 min. Calculations and preparations of standards were done as described by the manufacturer. One trait characteristic of *Methylomonas* sp. 16a is the production of large amounts of glycogen when cells are cultivated under certain grown conditions. *Methylomonas* strain MWM1200 (glgA$^+$) produced a significant amount of glycogen (~55% dry cell weight), whereas, in the *Methylomonas* strain MWM1500 (glgA$^-$) only 0.2% of the total cellular content was glycogen (Table 7).

TABLE 7

Evaluation of glycogen production in *Methylomonas* strains MWM1200 and MWM1500.

| *Methylomonas* 16a Derived Strain | Glycogen (%) dry cell weight |
|---|---|
| MWM1200 (glgA$^+$) | ~55 |
| MWM1500 (glgA$^-$) | 0.2 |

It was hypothesized that the deletion of glgA would block the ability of the cell to make glycogen. Theoretically, a knockout mutation resulting in the absence of the glycogen synthase activity should allow additional carbon to be pulled towards C$_{40}$ carotenoids synthesis (FIG. 2). The total carotenoid titer increased ~35% in strain MWM1500 (glgA$^-$) as compared to strain MWM1200 (glgA$^+$). In addition, a slight increase in growth rate for MWM1500 was detected (0.3 hr$^{-1}$ versus 0.26 hr$^{-1}$) (Table 8).

TABLE 8

Evaluation of total carotenoid production and growth rate in Methylomonas strains MWM1200 and MWM1500.

| Methylomonas Strain | Astaxanthin Plasmid | Total Carotenoid Titer (ppm) | Growth Rate (hr$^{-1}$) |
|---|---|---|---|
| MWM1200 (glgA$^+$) | pDCQ343 | 520 | 0.26 |
| MWM1500 (glgA$^-$) | pDCQ343 | 720 | 0.30 |

Example 6

PCR Amplification and Cloning of the E. coli glgA DNA Fragments into pGP704::sacB The PCR primers listed in Table 9 were used in the amplification of E. coli glgA deletion fragment #1 (SEQ ID NO: 19) and E. coli glgA deletion fragment #2 (SEQ ID NO: 20), both were ~1.0 kB in size. The PCR reaction mixture was composed of the following: 5 µL of 10× MasterAmp™ Taq PCR buffer (Epicentre®), 4 µL (1 µL each) of dNTPs (Applied Biosystems), 1 µL E. coli W3110 chromosomal DNA ( ), 4 µL of MgCl$_2$ (25 mM), 15 µL of 10× Master-Amp™ Enhancer (Epicentre®) (3× final concentration), 0.25 µL MasterAmp™ Taq DNA Polymerase (5 U/µL) (Epicentre®), 1 µL of each primer pair [E. coli BglII/glgA (deletion) #1 (SEQ ID NO: 21)+E. coli NotI, XbaI/glgA (deletion) #1 (SEQ ID NO: 22) or E. coli NotI/glgA (deletion) #2 (SEQ ID NO: 23)+E. coli XbaI/glgA (deletion) #2 (SEQ ID NO: 24)] and sterile water (added to achieve a final volume of 50 µL). The PCR reaction was performed using a GeneAmp® PCR 9700 System (Perkin Elmer), according to the thermocycling parameters below:

1 cycle: 95° C. (5 min);
30 cycle: 94° C. (15 sec), 60° C. (30 sec), 72° C. (30 sec)
1 cycle: 72° C. (6 min)

The PCR products were checked on a 0.8% agarose gel. As expected, ~1.0 kB fragments were produced for both the E. coli glgA deletion fragment #1 and E. coli glgA deletion fragment #2.

The fresh PCR products were cloned using the TOPO® TA Cloning® Kit (Invitrogen). The TOPO® reaction contained 4 µL fresh PCR product, 1 µL Salt solution (as provided in the TOPO® TA Cloning® Kit), and 1-µL TOPO® vector (pCR®2.1), which was incubated for 30 minutes at room temperature. E. coli TOP10™ cells were transformed with 2 µL of the TOPO® reaction. The transformation mixture was incubated on ice for 30 minutes and grown out for 30 minutes at 37° C. Subsequently the 50 µL and 100 µL of the transformation mixture were plated on to LB/Amp$^{100}$/X-gal$^{50}$ (50 µg/mL). A blue/white screen was used to identify insert-containing vectors. The white colonies were inoculated into a 96-well microtiter plated containing 150 µL of LB/Amp$^{50}$ that were used in a PCR screen to identify vectors that contain the correct insert DNA fragment. Additionally, 25 µL of the microtiter culture was used to inoculate eight culture tubes containing 2 mL of LB/Amp$^{50}$. These cultures were used for plasmid isolation, which was analyzed via restriction digestion to identify vectors that contain the correct insert DNA fragment (E. coli glgA deletion fragment #1 or E. coli glgA deletion fragment #2). The TOPO® clones containing the E. coli glgA deletion fragment #1 insert DNA was digested with EcoRV and KpnI and the TOPO® clones containing E. coli glgA deletion fragment #2 insert DNA was digested with NotI and XbaI.

Seven of eight sample were found to be correct for the E. coli glgA deletion fragment #1 samples and eight out of eight samples were correct for the E. coli glgA deletion fragment #2. Larger amounts of DNA were digested, separated on a 0.8% agarose gel, excised from the gel and purified using the QIAquick® gel extraction kit (Qiagen). The purified E. coli glgA deletion fragment #1 was subsequently digested with BglII and XbaI. Following the clean-up of the digestion using the Qiagen PCR purification kit, the BglII/XbaI digested E. coli glgA deletion fragment #1 insert DNA was used in the ligation reaction. The components of the ligation reaction were the following: 10× Fast-Link™ Ligation Buffer (1 µL; Epicentre®), 10 mM ATP (1 µL), BglII/XbaI digested pGP704-sacB vector DNA (4 µL), BglII/XbaI digested E. coli glgA deletion fragment #1 insert DNA and Fast-Link™ DNA ligase (1 µL). The ligation reaction was carried out at room temperature overnight. Prior to the transformation of calcium chloride competent E. coli SY327 cells, heating at 75° C. for 15 minutes inactivated the ligation mixture. The newly transformed E. coli SY327 cells (50 µL and 100 µL) were plated onto LB+Amp$^{50}$ agar plates.

Twelve colonies were selected and grown for plasmid isolation (QIAprep® Spin Mini-prep Kit; Qiagen). Digestion of the plasmid DNA with BglII and XbaI at 37° C. for 1.5 hours revealed that five of the 12 samples produced a restriction pattern that suggested the plasmid contained the correct first insert DNA (E. coli glgA deletion fragment #1). To confirm the presence of the E. coli glgA deletion fragment #1, additional digestion were performed using restriction endonucleases NotI/XbaI and EcoRI. DNA samples having the proper insert DNA were expected to produce a single band when digested with NotI/XbaI and three bands (3.2 kB, 2.5 kB & 0.7 kB) were predicted for the EcoRI digestion. One of the three samples produced bands of the expected sizes for both digestions. The NotI/XbaI sample was dephosphorylated by the addition of 3 µL of shrimp alkaline phosphatase (SAP; USB Corp.), which was incubated at 37° C. for 30 minutes. Afterward the dephosphorylation reaction was terminated via incubation at 65° C. for 15 minutes, the QIAquick® PCR purification kit (Qiagen) was used to clean-up the reaction. This SAP-treated pGP704-sacB+E. coli glgA deletion fragment #1 NotI/XbaI digested DNA served as the vector DNA in the ligation reaction. The E. coli glgA deletion fragment #2 DNA fragment previously digested with NotI/XbaI served as the insert DNA. Using the Fast-Link™ DNA ligase protocol described earlier, the ligation reaction was incubated for three hours in a room temperature water bath. After terminating the ligation reaction by heating to 70° C. for 15 minutes, the vector DNA was used to transform calcium chloride competent E. coli SY327 cells.

The transformation mixture (50 µL and 100 µL) was spread onto two LB+Amp$^{50}$ agar plates. Eight colonies were selected and inoculated into 5 mL of LB+Amp$^{50}$ broth of plasmid isolation. The plasmid DNA was isolated using the Qiagen QIAprep® Spin Mini-prep Kit as described previously. The plasmid DNA samples were evaluated for the correct insert DNA fragment by digestion with BglII and XbaI at 37° C. for 2.5 hours. All eight samples produced DNA fragments of the expected sizes (5.4 kB and 2.0 kB) indicating that both DNA inserts were present (E. coli glgA deletion fragment #1 & E. coli glgA deletion fragment #2). This plasmid (pGP704::sacB::E. coli ΔglgA; SEQ ID NO: 25) was transferred into E. coli MC1061 (F$^-$ hsdR2 hsdM$^+$ hsdS$^+$ mcrA mcrB1 araD9 Δ(ara-leu)7696 Δ(laclPOZY)X74 galE15 galU galK16 rpsL thi λ$^-$) (Casadaban, M. J. and Cohen, S. N., J. Mol. Biol. 138(2):179–207 (1980)) via tri-parental mating.

TABLE 9

PRIMERS UTILIZED FOR CLONING THE *E. coli* glgA DELETION DNA FRAGMENTS

| Deletion Fragment | Forward Primer | Reverse Primer | Size of PCR Fragment |
|---|---|---|---|
| *E. coli* glgA deletion fragment #1 | *E. coli* Bg/II/glgA (deletion) #1 5'-AGATCTATCCGCCAG GTTATCGTAGG-3' (SEQ ID NO: 21) | *E. coli* NotI, XbaI/glgA (deletion) #1 5'-TCTAGAATGCGGCCG CCGTCAGGCTATGGC AATGGA-3' (SEQ ID NO: 22) | ~1.0 kB |
| *E. coli* glgA deletion fragment #2 | *E. coli* NotI/glgA (deletion) #2 5'-GCGGCCGCTAAGCAG CGGGAACATCTCT-3' (SEQ ID NO: 23) | *E. coli* XbaI/glgA (deletion) #2 5'-TCTAGAAATACGTGGT GATCCTGGCGGG-3' (SEQ ID NO: 24) | ~1.0 kB |

Example 7

Tri-Parental Conjugation of the glgA Integration Vector into *E. Coli*

The conjugation method, tri-parental mating, used three different strains of *E. coli*. Each strain was grown in 25-mL volumes in a 125-mL shake flask overnight in the appropriate antibiotic.

Donor: *E. coli* SY327 (Miller, V. L. and Mekalanos, J. J., supra (1984))(F$^-$ araD Δ(lac-proAB) argE(Am) rif nalA recA56) containing the glgA deletion plasmid pGP704+sacB+*E. coli* glgA (Amp$^R$)

Recipient: *E. coli* MC1061 (Casadaban, M. J. and Cohen, S. N., supra) (F$^-$ hsdR2 hsdM$^+$ hsdS$^+$ mcrA mcrB1 araD139 Δ(ara-leu)7696 Δ(lacIPOZY)X74 galE15 galU galK16 rpsL thi λ$^-$)

Helper: *E. coli* DH5α (Invitrogen, Carlsbad, Calif.) (F$^-$ φ80dlacZΔM15 Δ(lacZYA-argF)U169 recA1 endA1 hsdR17($r_k^-$, $m_k^+$) phoA supE44 I- thi-1 gyrA96 relA1) containing the helper plasmid pRK2073 (Cm$^R$) (ATCC Number 37339)

The saturated cultures (2 mL) were transferred to Falcon (14-mL polypropylene round-bottom) tubes (Becton Dickinson Labware, Franklin Lakes, N.J.) and centrifuged of 5 minutes at ~4300 rpm (Sorvall centrifuge; available from Kendro Lab Products, Newtown, Conn.)). The supernatant was discarded and the cells were washed with 2 mL of LB broth. The cells were centrifuged for a second time under the same conditions, the supernatant was removed and the cells were again re-suspended in 2 mL of LB broth. The donor, helper and recipient cells were combined into a single tube and incubated at 37° C. without aeration for three hours. As a mating control, the helper and recipient cells were also mixed together. Following the incubation period, the cultures were centrifuged for five minutes at 4300 rpm. The supernatant again was discarded and the cells were washed in 2 mL of 1×M9 salts. After harvesting the cells using the same centrifugation conditions described previously, the cells were re-suspended in 2 mL of M9 salts medium. Dilutions of the mating mixture were plated on supplemented M9 agar plates (M9+Leucine (Leu)+Thiamine (B1)+Amp$^{50}$, M9+B1+Amp$^{50}$, and M9+Leu+B1), that were incubated at 37° C. for three days. Four colonies from the M9+Leu+B1+Amp$^{50}$ agar plates were grown in M9+Leu+B1 medium for two day at 37° C. with aeration and dilutions of the saturated culture were plated onto LB+sucrose (suc) agar plates (5% final concentration). One hundred colonies were patched onto LB+Amp$^{50}$ and LB agar plates. Growth of 99 patches was visible only on the LB agar plates, which indicated that the majority of the cultures had lost the integration vector backbone (pGP704-sacB). These cells either contained an intact glgA (SEQ ID NO: 17) or a glgA deletion. Forty-eight of the patches were screened for glgA deletion using PCR methodology and PCR primers *E. coli* BglII glgA deletion #1 and *E. coli* XbaI glgA deletion #2 (Table 10). The PCR was carried out using a GeneAmp® PCR System 9700 (Perkin Elmer) and the following PCR conditions: 94° C. 5 min.; 1 cycle (94° C. 5 min., 60° C. 2 min., 72° C. 3 min.); 35 cycles (94° C. 1 min., 60° C. 2 min., 72° C. 3 min.); 1 cycle (94° C. 1 min., 60° C. 2 min., 72° C. 10 min.); Hold (4° C.). Cells having an intact glgA gene (SEQ ID NO: 17) generated a 3.3 kB PCR fragment and cells having the glgA deletion produced a 2.0 kB PCR fragment. Three of the cultures were found to possess a chromosomal deletion in the glgA gene. The *E. coli* glgA$^-$ strain was used to evaluate the effect of glgA on carotenoid synthesis.

TABLE 10

PRIMERS USED TO VERIFY THE DELETION OF THE *E. coli* glgA GENE

| Gene | Forward Primer | Reverse Primer | Intact Fragment | Deletion Fragment |
|---|---|---|---|---|
| glgA | *E. coli* Bg/II/glgA (deletion) #1 5'-AGATCTATCCGCCAG GTTATCGTAGG-3' (SEQ ID NO: 21) | *E. coli* XbaI/glgA (deletion) #2 5'-TCTAGAAATACGTGG TGATCCTGGCGGG-3' (SEQ ID NO: 24) | 3.3 kB | 2.0 kB |

Example 8

Tri-Parental Conjugation of the Astaxanthin Expression Plasmid (pDCQ343) into E. Coli Strains (+/−glgA)

E. coli strains MC1061 and MC1061 (ΔglgA) were used to evaluate the effect of glgA on the carotenoid synthesis in E. coli. The carotenoid plasmid pDCQ343 (SEQ ID NO: 5) comprises the carotenoid genes (crtWZEYIB) required for astaxanthin production. The three strains used in the tri-parental mating are outlined below:

Donor: E. coli DH5α (Invitrogen) (F⁻ φ80dlacZΔM15 Δ(lacZYA-argF)U169 recA1 endA1 hsdR17($r_k^-$, $m_k^+$) phoA supE44 I- thi-1 gyrA96 relA1) containing the donor plasmid pDCQ343 (Kan$^R$)

Recipient: E. coli MC1061 (ΔglgA) [F⁻ hsdR2 hsdM⁺ hsdS⁺ mcrA mcrB1 araD139 Δ(ara-leu)7696 Δ(lacIPOZY)X74 galE15 galU galK16 rpsL thi λ⁻]

Helper: E. coli DH5α (F⁻ 80dlacZΔM15 Δ(lacZYA-argF) U169 recA1 endA1 hsdR17($r_k^-$, $m_k^+$) phoA supE44 I- thi-1 gyrA96 relA1) containing the helper plasmid pRK2073 (Cm$^R$) (ATCC Number 37339)

Each strain was grown in 25 mL volumes in a 125-mL shake flask overnight in the appropriate antibiotic. The saturated cultures (2 mL) were transferred to Falcon tubes and centrifuged of 5 minutes at ~4300 rpm. The supernatant was discarded and the cells were washed with 2 mL of LB broth. The cells were centrifuged for a second time under the same conditions, the supernatant was removed and the cells were again re-suspended in 2 mL of LB broth. The donor, helper and recipient cells were combined into a single tube and incubated at 37° C. without aeration for three hours. As a mating control, the helper and recipient cells were mixed together. Following the incubation period, dilutions of the mating mixture was plated onto LB+Kan$^{50}$+Streptomycin 50 μg/mL (Str$^{50}$) agar plates, which were incubated overnight at 37° C. A total of three orange colonies were detected. Each colony was streaked onto LB+Kan$^{50}$ agar plates to get isolated colonies, which were used for titer determination.

Example 9

Analysis of $C_{40}$ Carotenoids Produced by E. Coli glgA Mutant Using HPCL-Photodiode Array To analyze the effect of the glgA deletion on the production of $C_{40}$ carotenoid in E. coli, glgA⁺ and glgA⁻ cells were inoculated in 150 μL of LB broth in a 500 mL flask to a starting OD of 0.025. The cells were grown at 37° C. with aeration for five hours (late log phase). Cultures grown for 14 hours (stationary phase) were inoculated with 100 mL of the five-hour culture. To determine the total carotenoid titer for each culture, 30 mL was used to determine dry cell weight (DCW) and 100 mL was used to determine the total carotenoid composition of the cultures.

Once the cultures grew to the desired growth phase, the cells used to determine total carotenoid composition were harvested via centrifugation in a 50-mL polypropylene tube (Corning Life Sciences, Acton, Mass.). The supernatant was discarded and ~0.5 mL of 0.1 mm diameter glass beads were added to each pellet. Also added to each pellet was 2.5 mL of a 50:50 mixture of tetrahydrofuran (THF):methanol. The pellet was dissolved by vortexing for approximately two minutes or until the cells broke apart and the cell were free of clumps. The cell suspension was centrifuged for 10 minutes at 8000 rpm. The supernatant was transferred to a new 50 mL tube, which was dried nitrogen for ~2 hours or until all of the liquid evaporated. The sample residue was re-suspended in 300 μL of solvent (10% THF/90% methanol) by vortexing. Prior to injection into the HPLC machine, the sample was filtered using a 0.2 μm syringe filter (Teflon®; catalog # PN4423T, Gelman Pall Life Sciences, Ann Arbor, Mich.) into a glass insert that placed inside of a small HPLC screw-capped tube.

Five independent cultures of E. coli strains MC1061 (glgA⁺) and MC1061 (ΔglgA) were grown for either five hours or 14 hours were evaluated to ascertain the effect of glgA on total carotenoid synthesis. Cells were harvested during log phase growth and the presence or absence of the glycogen synthase (encoded by the glgA gene; SEQ ID NO: 17) did not have an impact on the amount (<1% increase) of $C_{40}$ carotenoid produced in E. coli. The total carotenoid titers of the glgA⁺ strain (E. coli MC1061 glgA⁺) ranged from ~460 to ~600 ppm; the average titer for the five glgA⁺ samples was 521+/−53 ppm. The MC1061 (ΔglgA) cultures (i.e. glgA⁻) had total carotenoid titers ranging form ~490 to 570 ppm; the average titer for the five glgA⁻ samples was 524+/−36 ppm.

However, the absence of glycogen synthesis was found to have a positive effect on carotenoid synthesis when E. coli cells were harvested during stationary phase. The level of carotenoid produced in the glgA⁺ E. coli strain when cells were harvested during stationary phase ranged from ~900 to ~1100 ppm. In contrast, the glgA⁻ samples had carotenoid titers that ranged between ~1200 and ~1900 ppm (Table 11). Thus, E. coli strains that were unable to make glycogen, exhibited an ~34% increase in total carotenoid synthesis.

TABLE 11

Evaluation of Carotenoid Production in E. coli glgA (+/−) strains.
Evaluation of Glycogen Production
in E. coli Carotenoid-Productions Strains (+/− glgA)

| | TOTAL CAROTENOID (ppm) | | |
|---|---|---|---|
| | MC1061 (pDCQ343) | MC1061 ΔglgA (pDCQ343) | Percent Increase |
| Log Growth* | | | |
| Culture B | 508 | 552 | |
| Culture C | 556 | 486 | |
| Culture D | 486 | 567 | |
| Culture E | 462 | 523 | |
| Culture F | 593 | 492 | |
| Average | 521 (+/−53) | 524 (+/−36) | <1 |
| Stationary Growth* | | | |
| Culture B | 1098 | 1176 | |
| Culture C | 1116 | 1195 | |
| Culture D | 1085 | 1924 | |
| Culture E | 904 | 1279 | |
| Culture F | 964 | 1336 | |
| Average | 1033 (+/−93) | 1382 (+/−309) | ~34 |

The (+) denotes that the cultures were grown for five hours.
The (*) denotes that the cultures were grown for 14 hours.

What is claimed is:

1. A method for the production of carotenoid compounds comprising:
    a) providing a carotenogenic microbial host cell, having a gene encoding a glycogen synthase polypeptide comprising;
        i) a carotenoid biosynthetic pathway comprising carotenoid biosynthetic pathway genes; and
        ii) a disruption in the glycogen synthase gene;
    b) growing the host cell of (a) under conditions whereby at least one carotenoid compound is produced; and
    c) optionally isolating the carotenoid compound produced at step (b).

2. A method according to claim 1 wherein at least one of the carotenoid biosynthetic pathway genes is heterologous to the carotenogenic microbial host cell.

3. A method according to claim 2 wherein at least one of the carotenoid biosynthesis pathway genes heterologous to the carotenogenic microbial host cell is selected from the group consisting of genes encoding: geranylgeranyl pyrophosphate synthase, lycopene cyclase, phytoene desaturase, phytoene synthase, carotenoid hydroxylase, and carotenoid ketolase.

4. A method according to claim 1 wherein the carotenogenic microbial host cell is selected from the group consisting of fungi, yeast, algae, and bacteria.

5. A method according to claim 4 wherein the carotenogenic microbial host cell is selected from the group consisting of *Aspergilus, Trichoderma, Saccharomyces, Pichia, Candida, Hansenula, Salmonella, Bacillus, Acinetobacter, Zymomonas, Agrobacterium, Erythrobacter, Erwinia, Chlorobium, Chromatium, Flavobacterium, Cytophaga, Rhodobacter, Rhodococcus, Streptomyces, Brevibacterium, Corynebacteria, Mycobacterium, Deinococcus, Erwinia, Pseudomonas, Sphingomonas, Alcaligenes, Synechocystis,*

Synechococcus, Anabaena, Thiobacilus, Methanobacterium, Kiebsiella, and Myxococcus.

6. A method according to claim 4 wherein the carotenogenic microbial host cell is selected from the group consisting of Phaffia, Haematococcus, Escherichia, Erwinia, Pantoea, methylotrophic bacteria, and methanotrophic bacteria.

7. A method according to claim 6 wherein the methylotrophic bacteria and methanotrophic bacteria are selected from the group consisting of Methylomonas, Methylobacter, Methylococcus, Methylosinus, Methylomicrobium and Methylocystis.

8. A method according to claim 7 wherein the Methylomonas is Methylomonas sp. 16a (ATCC PTA-2402) or derivatives thereof.

9. A method according to claim 1 wherein the carotenogenic microbial host cell has the ATCC designation, PTA-6888.

10. A method according to claim 1 wherein the at least one carotenoid compound is selected from the group consisting of $C_{30}$ carotenoids, $C_{40}$ carotenoids, antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin.

11. A method of optimizing carotenoid production by a carotenogenic microbial host comprising:
   a) providing a first carotenogenic microbial host cell comprising:
      i) a carotenoid biosynthetic pathway; and
      ii) a gene encoding a glycogen synthase polypeptide; wherein said carotenogenic microbial host produces at least one carotenoid compound;
   b) disrupting the gene encoding a glycogen synthase polypeptide to create a second, mutant carotenogenic microbial host cell;
   c) growing said second mutant carotenogenic microbial host cell under conditions whereby at least one carotenoid compound is produced, wherein carotenoid production of said second mutant host is optimized.

12. A method of producing a high flux carotenogenic microbial host cell comprising:
   a) providing a first carotenogenic microbial host cell comprising;
      i) a carotenoid biosynthetic pathway; and
      ii) a gene encoding a glycogen synthase polypeptide; wherein said carotenogenic microbial host cell produces at least one carotenoid compound; and
   b) disrupting the gene encoding a glycogen synthase polypeptide in the host cell of step (a) whereby a high flux carotenoid microbial host cell is produced.

13. A method according to either of claims 11 or 12 wherein the carotenogenic microbial host cell is selected from the group consisting of fungi, yeast, algae, and bacteria.

14. A method according to claim 13 wherein the carotenogenic microbial host cell is selected from the group consisting of Phaffia, Haematococcus, Escherichia, Erwinia, Pantoea, methylotrophic bacteria, and methanotrophic bacteria.

15. A method according to claim 13 wherein the methylotrophic bacteria and methanotrophic bacteria are selected from the group consisting of Methylomonas, Methylobacter, Methylococcus, Methylosinus, Methylomicrobium and Methylocystis.

16. A method according to claim 15 wherein the Methylomonas is Methylomonas sp. 16a (ATCC PTA-2402) or derivatives thereof.

17. A method according to either of claims 11 or 12 wherein the at least one carotenoid compound is selected from the group consisting of $C_{30}$ carotenoids, $C_{40}$ carotenoids, antheraxanthin, adonirubin, adonixanthin, astaxanthin, canthaxanthin, capsorubrin, β-cryptoxanthin, α-carotene, β-carotene, epsilon-carotene, echinenone, 3-hydroxyechinenone, 3'-hydroxyechinenone, γ-carotene, 4-keto-γ-carotene, ζ-carotene, α-cryptoxanthin, deoxyflexixanthin, diatoxanthin, 7,8-didehydroastaxanthin, fucoxanthin, fucoxanthinol, isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, 4-keto-torulene, 3-hydroxy-4-keto-torulene, uriolide, uriolide acetate, violaxanthin, zeaxanthin-β-diglucoside, and zeaxanthin.

18. A method according to claim 6 wherein the Escherichia carotenogenic microbial host cell is Escherichia coli.

19. A method according to claim 14 wherein the Escherichia carotenogenic microbial host cell is Escherichia coli.

* * * * *

SEQUENCE LISTING

<160> NUMBER OF SEQ ID NOS: 26

<210> SEQ ID NO 1
<211> LENGTH: 1696
<212> TYPE: DNA
<213> ORGANISM: artificial sequence
<220> FEATURE:
<223> OTHER INFORMATION: npr-sacB cassette

<400> SEQUENCE: 1

```
gaattcgagc tcggtaccga tcttaacatt tttcccctat cattttttccg tcttcatttg      60 tcatttttc cagaaaaaat cgcgtcattc gactcatgtc taatccaaca cgtgtctctc       120
ggcttatccc ctgacaccgc ccgccgacag cccgcatggg acgattctat caattcagcc      180
gcggagtcta gttttatatt gcagaatgcg agattgctgg tttattataa caatataagt      240
tttcattatt ttcaaaaagg gggatttatt gtgggtttag gtaagaaatt gtctgttgct      300
gtcgccgctt cctttatgag tttaaccatc agtctgccgg gtgttcaggc cgctgaggat      360
atcaataacc aaaaagcata caagaaacg tacggcgtct ctcatattac acgccatgat       420
atgctgcaga tccctaaaca gcagcaaaac gaaaaatacc aagtgcctca attcgatcaa      480
tcaacgatta aaatattga gtctgcaaaa ggacttgatg tgtccgacag ctggccgctg       540
caaaacgctg acggaacagt agcagaatac aacggctatc acgttgtgtt tgctcttgcg      600
ggaagcccga agacgctga tgacacatca atctacatgt tttatcaaaa ggtcggcgac       660
aactcaatcg acagctggaa aaacgcgggc cgtgtctta aagacagcga taagttcgac       720
gccaacgatc cgatcctgaa agatcagacg caagaatggt ccggttctgc aacctttaca      780
tctgacggaa aaatccgttt attctacact gactattccg gtaaacatta cggcaaacaa      840
agcctgacaa cagcgcaggt aaatgtgtca aaatctgatg acacactcaa atcaacgga       900 gtggaagatc acaaaacgat ttttgacgga gacggaaaaa catatcagaa cgttcagcag      960
tttatcgatg aaggcaatta tacatccgcc gacaaccata cgctgagaga ccctcactac     1020
gttgaagaca aaggccataa ataccttgta ttcgaagcca cacgggaac agaaaacgga      1080 taccaaggcg aagaatcttt atttaacaaa gcgtactacg gcggcggcac gaacttcttc     1140
cgtaaagaaa gccagaagct tcagcagagc gctaaaaac gcgatgctga gttagcgaac      1200
ggcgccctcg gtatcataga gttaaataat gattacacat gaaaaagt aatgaagccg       1260 ctgatcactt caaacacggt aactgatgaa atcgagcgcg cgaatgtttt caaaatgaac     1320
ggcaaatggt acttgttcac tgattcacgc ggttcaaaaa tgacgatcga tggtattaac      1380
tcaaacgata tttacatgct tggttatgta tcaaactctt taccggccc ttacaagccg       1440 ctgaacaaaa cagggcttgt gctgcaaatg ggtcttgatc caaacgatgt gacattcact      1500
tactctcact tcgcagtgcc gcaagccaaa ggcaacaatg tggttatcac aagctacatg     1560
acaaacagag gcttcttcga ggataaaaag gcaacatttg gcccaagctt cttaatcaac      1620
atcaaaggca ataaaacatc cgttgtcaaa acagcatcc tggagcaagg acagctgaca      1680
gtcaactaat aacagc                                                     1696
```

<210> SEQ ID NO 2
<211> LENGTH: 34
<212> TYPE: DNA
<213> ORGANISM: artificial sequence
<220> FEATURE:
<223> OTHER INFORMATION: Primer -continued

```
<400> SEQUENCE: 2
gacatcgatg tcgaattcga gctcggtacc gatc                               34

<210> SEQ ID NO 3
<211> LENGTH: 32
<212> TYPE: DNA
<213> ORGANISM: artificial sequence
<220> FEATURE:
<223> OTHER INFORMATION: Primer

<400> SEQUENCE: 3
gacctcgtcg ctgttattag ttgactgtca gc                                 32

<210> SEQ ID NO 4
<211> LENGTH: 5420
<212> TYPE: DNA
<213> ORGANISM: artificial sequence
<220> FEATURE:
<223> OTHER INFORMATION: Plasmid pGP704::sacB

<400> SEQUENCE: 4
gatcgctagt tgttttgac tccatccatt agggcttcta aaacgccttc taaggccatg    60
tcagccgtta agtgttcctg tgtcactgaa aattgctttg agaggctcta agggcttctc   120
agtgcgttac atccctggct tgttgtccac aaccgttaaa ccttaaaagc tttaaaagcc   180
ttatatattc tttttttct tataaaactt aaaaccttag aggctattta agttgctgat   240
ttatattaat tttattgttc aaacatgaga gcttagtacg tgaaacatga gagcttagta   300
cgttagccat gagagcttag tacgttagcc atgagggttt agttcgttaa acatgagagc   360
ttagtacgtt aaacatgaga gcttagtacg tgaaacatga gagcttagta cgtactatca   420
acaggttgaa ctgctggatc ctttttgtcc ggtgttgggt tgaaggtgaa gccggtcggg   480
gccgcagcgg gggccggctt ttcagccttg ccccccctgct tcggccgccg tggctccggc   540
gtcttgggtg ccggcgcggg ttccgcagcc ttggcctgcg gtgcgggcac atcggcgggc   600
ttggccttga tgtgccgcct ggcgtgcgag cggaacgtct cgtaggagaa cttgaccttc   660
cccgtttccc gcatgtgctc ccaaatggtg acgagcgcat agccggacgc taacgccgcc   720
tcgacatccg ccctcaccgc caggaacgca accgcagcct catcacgccg gcgcttcttg   780
gccgcgcggg attcaaccca ctcggccagc tcgtcggtgt agctctttgg catcgtctct   840
cgcctgtccc ctcagttcag taatttcctg catttgcctg tttccagtcg gtagatattc   900
cacaaaacag cagggaagca gcgcttttcc gctgcataac cctgcttcgg ggtcattata   960 gcgattttt cggtatatcc atccttttc gcacgatata caggattttg ccaaggggtt  1020
cgtgtagact ttccttggtg tatccaacgg cgtcagccgg gcaggatagg tgaagtaggc  1080
ccacccgcga gcgggtgttc cttcttcact gtcccttatt cgcacctggc ggtgctcaac  1140
gggaatcctg ctctgcgagg ctggccggct accgccggcg taacagatga gggcaagcgg  1200
atggctgatg aaaccaagcc aaccaggaag ggcagcccac ctatcaaggt gtactgcctt  1260
ccagacgaac gaagagcgat tgaggaaaag gcggcggcgg ccggcatgag cctgtcggcc  1320
tacctgctgg ccgtcggcca gggctacaaa atcacgggcg tcgtggacta tgagcacgtc  1380
cgcgagctgg cccgcatcaa tggcgacctg gccgcctgg cggcctgct gaaactctgg  1440 ctcaccgacg acccgcgcac ggcgcggttc ggtgatgcca cgatcctcgc cctgctggcg  1500
aagatcgaag agaagcagga cgagcttggc aaggtcatga tgggcgtggt ccgcccgagg  1560
gcagagccat gactttttta gccgctaaaa cggccgggg gtgcgcgtga ttgccaagca  1620
```

-continued

```
cgtccccatg cgctccatca agaagagcga cttcgcggag ctggtgaagt acatcaccga   1680
cgagcaaggc aagaccgagc gcctgggtca cgtgcgcgtc acgaactgcg aggcaaacac   1740
cctgcccgct gtcatggccg aggtgatggc gacccagcac ggcaaccccc gttccgaggc   1800
cgacaagacc tatcacctgc tggttagctt ccgcgcggga gagaagcccg acgcggagac   1860
gttgcgcgcg attgaggacc gcatctgcgc tgggcttggc ttcgccgagc atcagcgcgt   1920
cagtgccgtg catcacgaca ccgacaacct gcacatccat atcgccatca acaagattca   1980
cccgacccga acaccatcc atgagccgta tcgggcctac cgcgcccctcg ctgacctctg   2040
cgcgacgctc gaacgggact acgggcttga gcgtgacaat cacgaaacgc ggcagcgcgt   2100
ttccgagaac cgcgcgaacg acatggagcg gcacgcgggc gtggaaagcc tggtcggctg   2160
gatcctctac gccggacgca tcgtggccgg catcaccggc gccacaggtg cggttgctgg   2220
cgcctatatc gccgacatca ccgatgggga agatcgggct cgccacttcg ggctcatgag   2280
cgcttgtttc ggcgtgggta tggtggcagg ccccgtggcc gggggactgt tgggcgccat   2340
ctccttgctg cctcgcgcgt tcggtgatga cggtgaaaa cctctgacac atgcagctcc   2400
cggagacggt cacagcttgt ctgtaagcgg atgccgggag cagacaagcc cgtcagggcg   2460
cgtcagcggg tgttggcggg tgtcggggcg cagccatgac ccagtcacgt agcgatagcg   2520
gagtgatgac caggtcgaat tcgagctcgg taccgatctt aacatttttc ccctatcatt   2580
tttccgtctt catttgtcat tttttccaga aaaaatcgcg tcattcgact catgtctaat   2640
ccaacacgtg tctctcggct tatccctga caccgcccgc cgacagcccg catgggacga   2700
ttctatcaat tcagccgcgg agtctagttt tatattgcag aatgcgagat tgctggttta   2760
ttataacaat ataagttttc attattttca aaaggggga tttattgtgg gtttaggtaa   2820
gaaattgtct gttgctgtcg ccgcttcctt tatgagttta accatcagtc tgccgggtgt   2880
tcaggccgct gaggatatca ataaccaaaa agcatacaaa gaaacgtacg gcgtctctca   2940
tattacacgc catgatatgc tgcagatccc taaacagcag caaaacgaaa ataccaagt    3000
gcctcaattc gatcaatcaa cgattaaaaa tattgagtct gcaaaaggac ttgatgtgtc   3060
cgacagctgg ccgctgcaaa acgctgacgg aacagtagca gaatacaacg gctatcacgt   3120
tgtgtttgct cttgcgggaa gcccgaaaga cgctgatgac acatcaatct acatgtttta   3180
tcaaaaggtc ggcgacaact caatcgacag ctggaaaaac gcgggccgtg tctttaaaga   3240
cagcgataag ttcgacgcca acgatccgat cctgaaagat cagacgcaag aatggtccgg   3300
ttctgcaacc tttacatctg acggaaaaat ccgtttattc tacactgact attccggtaa   3360
acattacggc aaacaaagcc tgacaacagc gcaggtaaat gtgtcaaaat ctgatgacac   3420
actcaaaatc aacggagtgg aagatcacaa acgatttttt gacggagacg gaaaaacata   3480
tcagaacgtt cagcagttta tcgatgaagg caattataca tccgccgaca accatacgct   3540
gagagaccct cactacgttg aagacaaagg ccataaatac cttgtattcg aagccaacac   3600
gggaacagaa aacggatacc aaggcgaaga atctttattt aacaaagcgt actacggcgg   3660
cggcacgaac ttcttccgta aagaaagcca gaagcttcag cagagcgcta aaaacgcga    3720
tgctgagtta gcgaacggcg ccctcggtat catagagtta ataatgatt acacattgaa    3780
aaaagtaatg aagccgctga tcacttcaaa cacggtaact gatgaaatcg agcgcgcgaa   3840
tgttttcaaa atgaacggca atggtacttt gttcactgat tcacgcggtt caaaaatgac   3900
gatcgatggt attaactcaa acgatattta catgcttggt tatgtatcaa actctttaac   3960
cggcccttac aagccgctga acaaaacagg gcttgtgctg caaatgggtc ttgatccaaa   4020
```

```
cgatgtgaca ttcacttact ctcacttcgc agtgccgcaa gccaaaggca acaatgtggt    4080
tatcacaagc tacatgacaa acagaggctt cttcgaggat aaaaaggcaa catttggccc    4140
aagcttctta atcaacatca aaggcaataa acatccgtt  gtcaaaaaca gcatcctgga    4200
gcaaggacag ctgacagtca actaataaca gcgacatcga tgtctactgg cttaactatg    4260
cggcatcaga gcagattgta ctgagagtgc accaaaatta aaatgaagt  tttaaatcaa    4320 tctaaagtat atatgagtaa acttggtctg acagttacca atgcttaatc agtgaggcac    4380
ctatctcagc gatctgtcta tttcgttcat ccatagttgc ctgactcccc gtcgtgtaga    4440
taactacgat acgggagggc ttaccatctg gccccagtgc tgcaatgata ccgcgagacc    4500
cacgctcacc ggctccagat ttatcagcaa taaaccagcc agccggaagg gccgagcgca    4560
gaagtggtcc tgcaacttta tccgcctcca tccagtctat taattgttgc cgggaagcta    4620
gagtaagtag ttcgccagtt aatagtttgc gcaacgttgt tgccattgct gcaggcatcg    4680
tggtgtcacg ctcgtcgttt ggtatggctt cattcagctc cggttcccaa cgatcaaggc    4740
gagttacatg atcccccatg ttgtgcaaaa aagcggttag ctccttcggt cctccgatcg    4800
ttgtcagaag taagttggcc gcagtgttat cactcatggt tatggcagca ctgcataatt    4860
ctcttactgt catgccatcc gtaagatgct tttctgtgac tggtgagtac tcaaccaagt    4920
cattctgaga atagtgtatg cggcgaccga gttgctcttg cccggcgtca cacgggata     4980 ataccgcgcc acatagcaga actttaaaag tgctcatcat tggaaaacgt tcttcgggc     5040 gaaaactctc aaggatctta ccgctgttga gatccagttc gatgtaaccc actcgtgcac    5100
ccaactgatc ttcagcatct tttactttca ccagcgtttc tgggtgagca aaaacaggaa    5160
ggcaaaatgc cgcaaaaaag gaataagggc gacacggaa  atgttgaata ctcatactct    5220 tccttttca  atattattga agcatttatc agggttattg tctcatgagc ggatacatat    5280
ttgaatgtat ttagaaaaat aaacaaatag gggttccgcg cacatttccc cgaaaagtgc    5340
cacctgcaga tctgcaggtc gacggatccc aagcttctta tagaggtacc gcatgcgata    5400
tcgagctctc ccgggaattc                                                5420
```

<210> SEQ ID NO 5
<211> LENGTH: 11107
<212> TYPE: DNA
<213> ORGANISM: artificial sequence
<220> FEATURE:
<223> OTHER INFORMATION: Plasmid pDCQ343

<400> SEQUENCE: 5

```
accttcggga gcgcctgaag cccgttctgg acgccctggg gccgttgaat cgggatatgc     60
aggccaaggc cgccgcgatc atcaaggccg tgggcgaaaa gctgctgacg gaacagcggg    120
aagtccagcg ccagaaacag gcccagcgcc agcaggaacg cgggcgcgca catttccccg    180
aaaagtgcca cctgacgtct aagaaaccat tattatcatg acattaacct ataaaaatag    240
gcgtatcacg aggcccttg  cgccgaataa atacctgtga cggaagatca cttcgcagaa    300
taaataaatc ctggtgtccc tgttgatacc gggaagccct gggccaactt tggcgaaaa    360 tgagacgttg atcggcacgt aagaggttcc aactttcacc ataatgaaat aagatcacta    420
ccgggcgtat ttttttgagtt atcgagattt tcaggagcta aggaagctaa aatgagaaa    480 aaaatcactg gatataccac cgttgatata tcccaatggc atcgtaaaga acattttgag    540
gcatttcagt cagttgctca atgtacctat aaccagaccg ttcagctgga tattacggcc    600 ttttttaaaga ccgtaaagaa aaataagcac aagttttatc cggcctttat tcacattctt    660
```

```
gcccgcctga tgaatgctca tccggaattc actagaaagg aggaataaac catgaccgtc    720
gatcacgacg cacggatcag cctgctgctg gccgcagcca tcggcgccgc gtggctggcg    780
atccatgtcg gggcgatcgt gtggtggcga tggagcccgg cgacggcggt gctcgcgatc    840
cccgtcgtgc tcgtacaggc gtggctgagc accggcctgt tcatcgtcgc gcacgattgc    900
atgcacggat cgttcgtgcc cggccggccc gcggtcaacc ggaccgtcgg gacgctgtgc    960
ctcggcgcct atgcgggact gtcctatggc cagctccatc ccaagcatca tgcgcatcac   1020
gatgcgccgg gcaccgccgc cgaccccgat ttccatgccg gcgcgccgcg atccgcactg   1080
ccgtggttcg cgcgcttctt caccagctat tacacgcacg gccagatcct ccggatcacc   1140
gcggcggcgg tgctgtacat gctgctcggt gtgtcgctgc tcaacatcgt cgtgttctgg   1200
gcgttgccgg cgctgatcgc gctggcgcag ctgttcgtct tcggcaccht cctgccgcat   1260
cgccacggcg acacgccgtt cgcggacgcg cacaatgccc gcagcaacgg ctggccacgg   1320
ctggcgtcgc tggcgacctg cttccacttc ggcgcctatc atcacgaaca tcacctgagc   1380
ccgtggacgc cctggtggca gttgccgcgc gtcggccagc ctgccgccgg acaccggtcg   1440
ttaagcaaag accggtagac tagaaaggag gaataaaccca tgtcctggcc gacgatgatc   1500
ctgctgttcc tcgccaccht cctggggatg gaggtcttcg cctgggcgat gcatcgctat   1560
gtcatgcacg gcctgctgtg gacctggcac cgcagccatc atgagccgca cgacgacgtg   1620
ctggaaagga acgacctgtt cgcggtggtg ttcgccgccc cggccatcat cctcgtcgcc   1680
ttgggtctac atctgtggcc ttggatgctg ccgatcggcc tgggcgttac ggcctatgga   1740
ctggtttatt tcttctttca cgacgggctg gtgcatcgcc ggttcccgac agggatcgca   1800
gggcgctcgg cgttctggac gcgacgcatt caggcccacc ggctgcatca cgcggtgcgg   1860
acacgcgagg gctgcgtatc gttcggcttc cttgggtgc ggtcggcgcg cgcgctgaag   1920
gccgaactgt ctcagaaacg cggctcatcc agcaacggcg cctgaactag taccaaccat   1980
ggatagccat tatgaccacc catgtcgaca ccacagcaca tcagacaagc gaactccttc   2040
agctgcagca aattttacag gcgcatcttg aacatttact gcctgccgga cagcaaagcg   2100
atcgcgtgcg tgccgcgatg cgtgccggaa cgctggcgca gggcaaacgt attcgtcctt   2160
tattactgct gctggcagcg cgcgatatgg gttgcgagct gacgcaaaat ggcgttctcg   2220
atctcgcctg tgcagtggaa atggtgcacg cggcatcgct gattctggat gacattccct   2280
cgatggataa cgcgcagatg cgtcgtggtc gccctaccgt gcatcgcgaa tttggtgaaa   2340
acgtggcgat tctcgccgcc atcgcgctgc ttagccgcgc atttgaagtg attgccattg   2400
cacccggttt gcctgccata cataaatctg aagcgattgc tgaactctcc gctgccgtcg   2460
gcctgcaggg cttagtgcaa gggcaattcc aggatctgca cgacggcacg cagagccgca   2520
gcccggaagc gatcgccatg accaacgaac tgaaaaccag cgtgctgttt cgcgccacgc   2580
tgcaaatggc ggcgattgcc gctgacgctt caccgcaggt gcgcaaaga cttagcttct   2640 tcgcccagga tttgggccag gcgtttcaac tgctcgacga cctcgccgac ggttgcaaac   2700
acaccggtaa agatgtgcac caggatcagg gcaaatccac gctggtacag atgctcggtg   2760
ctgacggcgc ggaacgtcgc ctgcgcgatc acctgcgcag cgcagatgca caccttgcct   2820
gcgcctgcca tcgcggcatc gccactcgcc aatatatgca cgcgctgttt aatcaacagc   2880
tagcgatatt caactgaaag tcgtgctggc ggaggcgacc tgatgcgcac gcaatacgat   2940
gtgattttgg tcggtgctgg actggcgaat ggcttgattg cgctgcgtct gcgtcaattg   3000
cagccacaac tgaaatgcct gttgctggag agcgatgcgc atccggcagg caatcatacc   3060
```

```
tggtcgtttc atcacagcga tctcagcgcc gaacaacttc gctggctgca accgctgatt    3120
accgtgcgtt ggtcaggtta tcaggtgcgt tttcctgcgc tgcgccgcaa tctggacggg    3180
gattattgtt ccatcgcatc aggcgatttt gcccgccatc tttacgcggc gatgggtgac    3240
gatctgtgga caaacacagc cgtacaacag gtaaaaccca cgcaggtgac gctggcggat    3300
ggccgtgaac ttgctgcgca agtggtgatt gatggtcgcg gcctgcagcc gacgccacat    3360
ctgcagctgg gttatcaggt gtttcttgga caagagtggc agctggcgca gccgcacggc    3420
ctgcagcagc cgatcctgat ggatgccacc gtcgatcagc aagcgggtta tcgttttgtc    3480
tacacgctgc cgctcagcgc cgatcggcta ttgattgaag atacccatta cgttaaccag    3540
cccgcgctgg cggagaacac cgctcgtcag cacatcgccg actatgccaa tcagcaaggc    3600
tggacgctga gtacgctgct gcgtgaagag cacggcatat taccgattac cctgagcggc    3660
aacatcgatc gattctggca acagcagcgc ggccaagcgt gcagcggcct gcgcgccggg    3720
ctgtttcatg ccaccaccgg ttactccttg ccgtccgccg tggcgctagc ggagttggta    3780
gcagcgctgt tgcccaccga tgccctcacg ctcagccaac atatcgaacg ctttgcccgt    3840
cagcagtggc gcgaacagcg attttttccgt ctgctaaacc gcatgctgtt tttgccggt    3900
aagccgcagc agcgctggcg cgtgatgcaa cgttttacc ggctcgatgc cgggttaatt    3960
agccgctttt acgccgggca actgcgcctg cgcgataaaa cgcggattct gtgcggcaag    4020
ccgccggtgc ccatcggtga agcgctgcgc gcgctgttga actctgtcga accagggaag    4080
aaaaaatgaa acgcacttat gtgattggcg caggctttgg cggcctggcg ctggcgattc    4140
gcctgcaagc ggcgggcata ccaaccacct tactcgagca gcgcgacaaa ccgggcggac    4200
gcgcctatgt gtttgaggac agtggcttta ccttcgatgc cggacccacg gtgatcaccg    4260
atcccagcgc catcgaagag ttgttcacgc tggcaggaaa atcgctcagc gattacgtcg    4320
agctgatgcc ggtaacgccc ttctatcgcc tgtgctggga agatggcaaa cagcttgatt    4380
acgacaataa tcagccgctg ctggagcagc agatcgccac gttcaatccg caagatgtag    4440
aaggctatcg tcaatttctt gcctattcac gtgaagtatt tagagagggt tatctgaaac    4500
tcggcacggt gccgtttctg caggtgcgtg acatgctgcg cgtcgcgccg cagttgggac    4560
gtctgcaagc atggcgcagc gtctacagca tggtggcgaa atttattcag gacgatcatc    4620
tgcgtcaggc gttttccttc cactcattgc tggtgggcgg taatccttt gcaacgtcat    4680
cgatctatac cttaattcat gcgctggagc gtgaatgggg cgtgtggttt ccgcgcggcg    4740
gcaccggcgc gctggtgcag ggcatggcgc gactgttcga ggacttgggc ggcgagctgt    4800
tactgaatgc cgaagtgagc cagctggaaa ccagcggcaa tcgcattagc ggcgttcagt    4860
tagagggcgg acgacgcttc gatgccgccg ctgtggcctc caatgccgac gtggtgcata    4920
cctacgacaa actgcttcgc caccatccgc tggcaatgaa acgtgcgaca tcgctgaagc    4980
gtaagcgcat gagcaactcg ctgtttgtac tctatttgg cctgaatcag ccgcatgaac    5040
agctcgcgca ccacaccgtc tgttttggcc cgcgttatcg tgagttgatc gatgagattt    5100
tcaacagcag ccagctggca gacgattttt cactttacct gcacgcgccc tgcagcagcg    5160
atccgtcgct ggcaccgccc ggctgcggca gcttttatgt gttagcgccg gtgccgcatc    5220
tcggcaccgc tgcatcgac tggcaacagg aaggaccgcg cttgcgcgat cgaattttg    5280
cttatctgga gcagcactac atgccgggat tacgtcagca attagtgaca cacagaatgt    5340
ttacgccgtt tgattttcgc gacacgctgc atgcccatca cggctcggcg ttttcgctgg    5400
agccgatttt gacgcaaagc gcctggttcc gcccgcataa ccgcgatgcc gatatcagca    5460
```

```
atctctatct ggtgggtgcc ggtacgcatc caggcgcggg cgtgcccggc gtgatcggtt    5520
cggccaaggc caccgccagg ctgatgctgg aggatcgcgc gaatgaatc gacagccttt     5580 acttgagcaa gtaacgcaaa ccatggcggt gggctcgaag agtttcgcca ccgccgccaa    5640
gctgtttgat gcaccgacgc gccgcagcac gctgatgctg tatgcgtggt gtcgtcactg    5700
cgatgatgtg attgatgggc aaacgctggg cgaaggcggc acgcagcatg ccgtcgaaga    5760
cgcgcaggca cgtatgcagc atctgcaaat tgaaacccgc cgcgcctaca gcggcgcgca    5820
catggatgaa ccggcgttta gggcgtttca ggaagtggcg atcattcacc agctgccgca    5880
acaactggcg tttgatcatc tggaaggctt cgctatggat gcacgcaacg aacattacgc    5940
gagcttcgat gacacgctgc gttactgcta tcacgtcgcg ggcgtggtcg gtttgatgat    6000
ggcgcgcgta atgggcgtgc gcgacgaagc ggtgctcgat cacgcctgcg atttaggact    6060
ggcgttccag ctcactaaca ttgcgcgcga cattgtagaa gatgccgaaa atggtcgctg    6120
ctatctgccg caatcctggc tcgatcaggc gggattacgc gccgatacgc tgactgcacc    6180
gcaacatcgt gcagcgctcg cctcactggc agcgcgttta gtggcggagg cggaacccta    6240
ttatcactcg gcgcgatccg gtttaccggg tttaccgctg cgctcggcgt gggccatcgc    6300
tacggctcgc ggcgtttatc gcgaaattgg cgtcaaagtt cagcacgccg gtgtgcacgc    6360
ctgggattca cggcagcgca ccagtaaagg tgaaaaactg cgcgctgctgg tgaaaggggc    6420 aggtttggcg atcacttcgc gtgtgtctcg tcctgaaccg cgtccggctg gtctgtggca    6480
gcgtcctcgt tgaattccgt atggcaatga aagacggtga gctggtgata tgggatagtg    6540
ttcacccttg ttacaccgtt ttccatgagc aaactgaaac gttttcatcg ctctggagtg    6600
aataccacga cgatttccgg cagtttctac acatatattc gcaagatgtg gcgtgttacg    6660
gtgaaaacct ggcctatttc cctaaagggt ttattgagaa tatgtttttc gtctcagcca    6720
atccctgggt gagtttcacc agttttgatt taaacgtggc caatatggac aacttcttcg    6780
cccccgtttt caccatgggc aaatattata cgcaaggcga caaggtgctg atgccgctgg    6840
cgattcaggt tcatcatgcc gtctgtgatg gcttccatgt cggcagaatg cttaatgaat    6900
tacaacagta ctgcgatgag tggcagggcg gggcgtaatt ttttttaaggc agttattggt    6960 gcccttaaac gcctggtgct acgcctgaat aagtataata agcggatgaa tggcagaaat    7020
tcgaaagcaa attcgacccg gtcgtcggtt cagggcaggg tcgttaaata gccgcttatg    7080
tctattgctg gttaccggt ttattgacta ccggaagcag tgtgaccgtg tgcttctcaa    7140
atgcctgagg ccagtttgct caggctctcc ccgtggaggt aataattgac gatatgatca    7200
tttattctgc ctcccagagc ctgataaaaa cggtgaatcc gttagcgagg tgccgccggc    7260
ttccattcag gtcgaggtgg cccggctcca tgcaccgcga cgcaacgcgg ggaggcagac    7320
aaggtatagg gcggcgaggc ggctacagcc gatagtctgg aacagcgcac ttacgggttg    7380
ctgcgcaacc caagtgctac cggcgcggca gcgtgacccg tgtcggcggc tccaacggct    7440
cgccatcgtc cagaaaacac ggctcatcgg gcatcggcag gcgctgctgc ccgcgccgtt    7500
cccattcctc cgtttcggtc aaggctggca ggtctggttc catgcccgga atgccgggct    7560
ggctgggcgg ctcctcgccg gggccggtcg gtagttgctg ctcgcccgga tacagggtcg    7620
ggatgcggcg caggtcgcca tgccccaaca gcgattcgtc ctggtcgtcg tgatcaacca    7680
ccacggcggg actgaacacc gacaggcgca actggtcgcg gggctggccc cacgccacgc    7740
ggtcattgac cacgtaggcc gacacggtgc cgggggccgtt gagcttcacg acggagatcc    7800
agcgctcggc caccaagtcc ttgactgcgt attggaccgt ccgcaaagaa cgtccgatga    7860
```

```
gcttggaaag tgtcttctgg ctgaccacca cggcgttctg gtggcccatc tgcgccacga    7920
ggtgatgcag cagcattgcc gccgtgggtt tcctcgcaat aagcccggcc cacgcctcat    7980 gcgcttttgcg ttccgtttgc acccagtgac cgggcttgtt cttggcttga atgccgattt    8040
ctctggactg cgtggccatg cttatctcca tgcggtaggg tgccgcacgg ttgcggcacc    8100
atgcgcaatc agctgcaact tttcggcagc gcgacaacaa ttatgcgttg cgtaaaagtg    8160
gcagtcaatt acagattttc tttaacctac gcaatgagct attgcggggg gtgccgcaat    8220
gagctgttgc gtaccccct tttttaagtt gttgattttt aagtctttcg catttcgccc    8280
tatatctagt tctttggtgc ccaaagaagg gcacccctgc ggggttcccc cacgccttcg    8340
gcgcggctcc ccctccggca aaaagtggcc cctccggggc ttgttgatcg actgcgcggc    8400
cttcggcctt gcccaaggtg gcgctgcccc cttggaaccc ccgcactcgc cgccgtgagg    8460
ctcgggacct gcaggggggg gggggaaagc cacgttgtgt ctcaaaatct ctgatgttac    8520
attgcacaag ataaaatat atcatcatga acaataaaac tgtctgctta cataaacagt    8580
aatacaaggg gtgttatgag ccatattcaa cgggaaacgt cttgctcgag gccgcgatta    8640
aattccaaca tggatgctga tttatatggg tataaatggg ctcgcgataa tgtcgggcaa    8700
tcaggtgcga caatctatcg attgtatggg aagcccgatg cgccagagtt gtttctgaaa    8760
catggcaaag gtagcgttgc caatgatgtt acagatgaga tggtcagact aaactggctg    8820
acggaattta tgcctcttcc gaccatcaag cattttatcc gtactcctga tgatgcatgg    8880
ttactcacca ctgcgatccc cgggaaaaca gcattccagg tattagaaga atatcctgat    8940
tcaggtgaaa atattgttga tgcgctggca gtgttcctgc gccggttgca ttcgattcct    9000
gtttgtaatt gtccttttaa cagcgatcgc gtatttcgtc tcgctcaggc gcaatcacga    9060
atgaataacg gtttggttga tgcgagtgat tttgatgacg agcgtaatgg ctggcctgtt    9120
gaacaagtct ggaaagaaat gcataagctt ttgccattct caccggattc agtcgtcact    9180
catggtgatt tctcacttga taaccttatt tttgacgagg ggaaattaat aggttgtatt    9240
gatgttggac gagtcggaat cgcagaccga taccaggatc ttgccatcct atggaactgc    9300
ctcggtgagt tttctccttc attacagaaa cggctttttc aaaaatatgg tattgataat    9360
cctgatatga ataaattgca gtttcatttg atgctcgatg agttttttcta atcagaattg    9420 gttaattggt tgtaacactg gcagagcatt acgctgactt gacgggacgg cggctttgtt    9480
gaataaatcg aacttttgct gagttgaagg atcagatcac gcatcttccc gacaacgcag    9540
accgttccgt ggcaaagcaa aagttcaaaa tcaccaactg gtccacctac aacaaagctc    9600
tcatcaaccg tggctccctc actttctggc tggatgatgg ggcgattcag gcctggtatg    9660
agtcagcaac accttcttca cgaggcagac ctcagcgccc cccccccct gcaggtctcg    9720 gggggcaggc gggcgggctt cgccttcgac tgcccccact cgcataggct tgggtcgttc    9780
caggcgcgtc aaggccaagc cgctgcgcgg tcgctgcgcg agccttgacc cgccttccac    9840
ttggtgtcca accggcaagc gaagcgcgca ggccgcaggc cggaggcttt tccccagaga    9900
aaattaaaaa aattgatggg gcaaggccgc aggccgcgca gttggagccg gtgggtatgt    9960
ggtcgaaggc tgggtagccg gtgggcaatc cctgtggtca agctcgtggg caggcgcagc   10020
ctgtccatca gcttgtccag cagggttgtc cacgggccga cgaagcgag ccagccggtg   10080 gccgctcgcg gccatcgtcc acatatccac gggctggcaa gggagcgcag cgaccgcgca   10140
gggcgaagcc cggagagcaa gcccgtaggg cgccgcagcc gccgtaggcg gtcacggactt   10200 tgcgaagcaa agtctagtga gtatactcaa gcattgagtg gcccgccgga ggcaccgcct   10260
```

```
tgcgctgccc ccgtcgagcc ggttggacac caaaagggag gggcaggcat ggcggcatac    10320
gcgatcatgc gatgcaagaa gctggcgaaa atgggcaacg tggcggccag tctcaagcac    10380
gcctaccgcg agcgcgagac gcccaacgct gacgccagca ggacgccaga gaacgagcac    10440
tgggcggcca gcagcaccga tgaagcgatg gccgactgc gcgagttgct gccagagaag     10500
cggcgcaagg acgctgtgtt ggcggtcgag tacgtcatga cggccagccc ggaatggtgg    10560
aagtcggcca gccaagaaca gcaggcggcg ttcttcgaga aggcgcacaa gtggctggcg    10620
gacaagtacg gggcggatcg catcgtgacg ccagcatcc accgtgacga aaccagcccg      10680
cacatgaccg cgttcgtggt gccgctgacg caggacggca ggctgtcggc caaggagttc    10740
atcggcaaca aagcgcagat gacccgcgac cagaccacgt ttgcggccgc tgtggccgat    10800
ctagggctgc aacggggcat cgagggcagc aaggcacgtc acacgcgcat tcaggcgttc    10860
tacgaggccc tggagcggcc accagtgggc cacgtcacca tcagcccgca agcggtcgag    10920
ccacgcgcct atgcaccgca gggattggcc gaaaagctgg gaatctcaaa gcgcgttgag    10980
acgccggaag ccgtggccga ccggctgaca aaagcggttc ggcagggggta tgagcctgcc   11040 ctacaggccg ccgcaggagc gcgtgagatg cgcaagaagg ccgatcaagc caagagacg    11100 gcccgag                                                             11107

<210> SEQ ID NO 6
<211> LENGTH: 747
<212> TYPE: DNA
<213> ORGANISM: Sphingomonas melonis DC18

<400> SEQUENCE: 6
atgaccgtcg atcacgacgc acggatcagc ctgctgctgg ccgcagccat cggcgccgcg     60
tggctggcga tccatgtcgg ggcgatcgtg tggtggcgat ggagcccggc gacggcggtg    120
ctcgcgatcc ccgtcgtgct cgtacaggcg tggctgagca ccggcctgtt catcgtcgcg    180
cacgattgca tgcacggatc gttcgtgccc ggccggcccg cggtcaaccg gaccgtcggg    240
acgctgtgcc tcggcgccta tgcgggactg tcctatggcc agctccatcc caagcatcat    300
gcgcatcacg atgcgccggg caccgccgcc gaccccgatt ccatgccggg cgcgccgcga    360
tccgcactgc cgtggttcgc gcgcttcttc accagctatt acacgcacgg ccagatcctc    420
cggatcaccg cggcggcggt gctgtacatg ctgctcggtg tgtcgctgct caacatcgtc    480
gtgttctggg cgttgccggc gctgatcgcg ctggcgcagc tgttcgtctt cggcaccttc    540
ctgccgcatc gccacggcga cacgccgttc gcggacgcgc acaatgcccg cagcaacggc    600
tggccacggc tggcgtcgct ggcgacctgc ttccacttcg gcgcctatca tcacgaacat    660
cacctgagcc cgtggacgcc ctggtggcag ttgccgcgcg tcggccagcc tgccgccgga    720
caccggtcgt taagcaaaga ccggtag                                       747

<210> SEQ ID NO 7
<211> LENGTH: 486
<212> TYPE: DNA
<213> ORGANISM: Brevundimonas vesicularis DC263

<400> SEQUENCE: 7
atgtcctggc cgacgatgat cctgctgttc ctcgccacct tcctggggat ggaggtcttc     60
gcctgggcga tgcatcgcta tgtcatgcac ggcctgctgt ggacctggca ccgcagccat    120
catgagccgc acgacgacgt gctggaaagg aacgacctgt tcgcggtggt gttcgccgcc    180
ccggccatca tcctcgtcgc cttgggtcta catctgtggc cttggatgct gccgatcggc    240
```

```
ctgggcgtta cggcctatgg actggtttat tcttctttc acgacgggct ggtgcatcgc    300
cggttcccga cagggatcgc agggcgctcg gcgttctgga cgcgacgcat tcaggcccac    360
cggctgcatc acgcggtgcg gacacgcgag ggctgcgtat cgttcggctt cctttgggtg    420
cggtcggcgc gcgcgctgaa ggccgaactg tctcagaaac gcggctcatc cagcaacggc    480
gcctga                                                                486
```

<210> SEQ ID NO 8
<211> LENGTH: 1172
<212> TYPE: DNA
<213> ORGANISM: artificial sequence
<220> FEATURE:
<223> OTHER INFORMATION: glgA deletion fragment #1

<400> SEQUENCE: 8

```
agatcttgac cggttgaaat aagtcggtat gggctggatt gctcataggg atcgctcctg     60
cgaaggttga aggtaaagga gacgtcagtt taccagatcg attttgacca gaatccgtgt    120
ggcccggttt tgcgtgctgt aattccaggc agacaagccg cgttggtcag cctgttgccg    180
ttcggcgata ccgcctattt ctatccattc gccgagcctg gccgcaccg aggtatgcgc     240 gctttggctg tcgatgcggc cgccatggcg gaagcgttcg gcccagggag cgatgtcgag    300
catgacttca tcgttggctt gcaggcgcgg aatcaccgca aagccggtgc tggcttgctg    360
aaattgcgtg ccgctggtga caccggggta accgaaaccc gaatcgtaaa tcgtgacata    420
ctcgtaaggc cggagctggc cgatttctat tcgtgccggc tggccttcca aggtacgtaa    480
ctgttgcatc gcgcgctgct ctccggcgtc gcgggtatcg ccaaccatgc cctgcatccg    540
gatcgcgttg gggtaaaccg cgatggcggc ttcggcattc aattgttcgg ccgttttata    600
gctgctttgc aacacggaaa tgagcagatt gcgctgaggt ttatcgagtt gctggattaa    660
ctggccaatc tcttgcaggc gggccgggct ggctttgacg atcaaatcaa agccgttacc    720
ggtgacgact tcgttggctt ccaacaatgg catcaacaaa ggctggattt cggcggcagg    780
gcggtttcgt aatggaatca tctccatcac cgtttcttgc gcggcaacga cctgcagcca    840
aaacaggcta aagccggcga caaagcccgt cagcgctagt ttgcggtaat ggcgccaagc    900
cggcttggct tgccgtcgca ttgtgccgtg cgcaacccat cgatcaagcc aggcctgtga    960
acgacgaatg gagcctttag atttcacgat ataacgccag atactgattg gcgctgtttt   1020
cccaggaaaa atccttgcgc atcgcgttgc gctgcagctc ttgccagagc ttgggattgg   1080
cgtgcaccac cagcgcgcgc ttgatggttt ccagtaacgc gcccggtacg gcatcgttga   1140
agacgaatcc gctcacgcgt actagttcta ga                                 1172
```

<210> SEQ ID NO 9
<211> LENGTH: 1067
<212> TYPE: DNA
<213> ORGANISM: artificial sequence
<220> FEATURE:
<223> OTHER INFORMATION: glgA deletion fragment #2

<400> SEQUENCE: 9

```
acgcgtacta gtgatcaagg gatgggtttc gctactggcg aacaggattt ttttcatgtt     60
tcaaatctta cattttcagg atgatgccgg ccaagggcgg cagggtcacg gtaacggaat    120
ggttcatatt catccagggc aatggctctg aatgcacgta accattgccg atgttgctgc    180
catcgtaata ttcggagtcc gagttgaaga tttcatgata aacgccttcg cgcggcacgc    240
caatgcgata gttctcgcgt ggaaccggcg tgaagttcag tatcacgatc aagtcctcgt    300
```

```
tggcggattt acgccgatag ctgatgatcg attgctgata gtcatggcaa tcgatccatt       360
cgaaaccgtg atgatcgaaa tcgaattgat acagggccga atgagtggcg tagagtttgt       420
tcaggtcctt gaccagggtt tgcacgccgc gatgatgggg ataatcgagc acataccagt       480
ccagatcgcg gttcacactc cattcggtgc cctgggcgaa ttcgcagccc atgaacagca       540
gtttcttgcc ggggtaagtg aacatcaagg tgtacagcag gcgcagattg gcgaaacgct       600
gccattcgtc gcccggcatt ttgtttaata gggattgttt gccgtgcacg acttcgtcat       660
gcgaaaacgg cagtacgaaa ttctcggtga aggcatacag cagaccgaag gtcaacgagt       720
cgtggtgata ggaacgatgg atgggttgtt cctgcatgta atgcagaatg tcgtgcatcc       780
agcccatgtt ccatttcatc gagaatccca ggccgccggt ccaggtcggc cgggtgactt       840
gcggccagga ggtcgattct tccgccatga tcacggtgcc gggatgttgt tcgtgggtga       900
cggtgttcat gtggcgcagg aagtcgatgg cttccaggtt ttcgttgccg ccgtacatgt       960
tcggaatcca ttcgttggct tcgcgcgagt agtccagata cagcatcgag gccaccgcgt      1020
cgacgcgcaa gccgtccaga tggaattctt ccagccagaa gtctaga                    1067
```

```
<210> SEQ ID NO 10
<211> LENGTH: 26
<212> TYPE: DNA
<213> ORGANISM: artificial sequence
<220> FEATURE:
<223> OTHER INFORMATION: Primer

<400> SEQUENCE: 10
agatcttgac cggttgaaat aagtcg                                             26

<210> SEQ ID NO 11
<211> LENGTH: 38
<212> TYPE: DNA
<213> ORGANISM: artificial sequence
<220> FEATURE:
<223> OTHER INFORMATION: Primer

<400> SEQUENCE: 11
tctagaacta gtacgcgtga gcggattcgt cttcaacg                                38

<210> SEQ ID NO 12
<211> LENGTH: 32
<212> TYPE: DNA
<213> ORGANISM: artificial sequence
<220> FEATURE:
<223> OTHER INFORMATION: Primer

<400> SEQUENCE: 12
acgcgtacta gtcatcaagg gatgggtttc gc                                      32

<210> SEQ ID NO 13
<211> LENGTH: 25
<212> TYPE: DNA
<213> ORGANISM: artificial sequence
<220> FEATURE:
<223> OTHER INFORMATION: Primer

<400> SEQUENCE: 13
tctagacttc tggctggaag attcc                                              25

<210> SEQ ID NO 14
<211> LENGTH: 7604
<212> TYPE: DNA
<213> ORGANISM: artificial sequence
```

<220> FEATURE:
<223> OTHER INFORMATION: Plasmid pGP704::sacB::delta glgA

<400> SEQUENCE: 14

| | |
|---|---:|
| ctagaggtac cgcatgcgat atcgagctct cccgggaatt cgatcgctag tttgttttga | 60 |
| ctccatccat tagggcttct aaaacgcctt ctaaggccat gtcagccgtt aagtgttcct | 120 |
| gtgtcactga aaattgcttt gagaggctct aagggcttct cagtgcgtta catccctggc | 180 |
| ttgttgtcca caaccgttaa accttaaaag ctttaaaagc cttatatatt cttttttttc | 240 |
| ttataaaact taaaacctta gaggctattt aagttgctga tttatattaa ttttattgtt | 300 |
| caaacatgag agcttagtac gtgaaacatg agagcttagt acgttagcca tgagagctta | 360 |
| gtacgttagc catgagggtt tagttcgtta acatgagag cttagtacgt taaacatgag | 420 |
| agcttagtac gtgaaacatg agagcttagt acgtactatc aacaggttga actgctggat | 480 |
| cctttttgtc cggtgttggg ttgaaggtga agccggtcgg ggccgcagcg ggggccggct | 540 |
| tttcagcctt gcccccctgc ttcggccgcc gtggctccgg cgtcttgggt gccggcgcgg | 600 |
| gttccgcagc cttggcctgc ggtgcgggca tcggcgggg cttggccttg atgtgccgcc | 660 |
| tggcgtgcga gcggaacgtc tcgtaggaga acttgacctt ccccgtttcc cgcatgtgct | 720 |
| cccaaatggt gacgagcgca tagccggacg ctaacgccgc ctcgacatcc gccctcaccg | 780 |
| ccaggaacgc aaccgcagcc tcatcacgcc ggcgcttctt ggccgcgcgg gattcaaccc | 840 |
| actcggccag ctcgtcggtg tagctctttg gcatcgtctc tcgcctgtcc cctcagttca | 900 |
| gtaatttcct gcatttgcct gtttccagtc ggtagatatt ccacaaaaca gcagggaagc | 960 |
| agcgctttt cgctgcataa ccctgcttcg gggtcattat agcgattttt tcggtatatc | 1020 |
| catccttttt cgcacgatat acaggatttt gccaaagggt tcgtgtagac tttccttggt | 1080 |
| gtatccaacg gcgtcagccg ggcaggatag gtgaagtagg cccacccgcg agcgggtgtt | 1140 |
| ccttcttcac tgtcccttat tcgcacctgg cggtgctcaa cgggaatcct gctctgcgag | 1200 |
| gctggccggc taccgccggc gtaacagatg agggcaagcg gatggctgat gaaaccaagc | 1260 |
| caaccaggaa gggcagccca cctatcaagg tgtactgcct tccagacgaa cgaagagcga | 1320 |
| ttgaggaaaa ggcggcggcg gccggcatga gcctgtcggc ctacctgctg gccgtcggcc | 1380 |
| agggctacaa aatcacgggc gtcgtggact atgagcacgt ccgcgagctg gcccgcatca | 1440 |
| atggcgacct gggccgcctg gcggcctgc tgaaactctg gctcaccgac gacccgcgca | 1500 |
| cggcgcggtt cggtgatgcc acgatcctcg ccctgctggc gaagatcgaa gagaagcagg | 1560 |
| acgagcttgg caaggtcatg atgggcgtgg tccgcccgag ggcagagcca tgactttttt | 1620 |
| agccgctaaa acgccggggg ggtgcgcgtg attgccaagc acgtccccat gcgctccatc | 1680 |
| aagaagagcg acttcgcgga gctggtgaag tacatcaccg acgagcaagg caagaccgag | 1740 |
| cgcctgggtc acgtgcgcgt cacgaactgc gaggcaaaca ccctgcccgc tgtcatggcc | 1800 |
| gaggtgatgg cgacccagca cggcaacacc cgttccgagg ccgacaagac ctatcacctg | 1860 |
| ctggttagct ccgcgcggg agagaagccc gacgcggaga cgttgcgcgc gattgaggac | 1920 |
| cgcatctgcg ctgggcttgg cttcgccgag catcagcgcg tcagtgccgt gcatcacgac | 1980 |
| accgacaacc tgcacatcca tatcgccatc aacaagattc acccgacccg aaacaccatc | 2040 |
| catgagccgt atcgggccta ccgcgccctc gctgacctct gcgcgacgct cgaacgggac | 2100 |
| tacgggcttg agcgtgacaa tcacgaaacg cggcagcgcg tttccgagaa ccgcgcgaac | 2160 |
| gacatggagc ggcacgcggg cgtggaaagc ctggtcggct ggatcctcta cgccggacgc | 2220 |

```
atcgtggccg gcatcaccgg cgccacaggt gcggttgctg gcgcctatat cgccgacatc    2280
accgatgggg aagatcgggc tcgccacttc gggctcatga gcgcttgttt cggcgtgggt    2340
atggtggcag gccccgtggc cgggggactg ttgggcgcca tctccttgct gcctcgcgcg    2400
tttcggtgat gacggtgaaa acctctgaca catgcagctc ccggagacgg tcacagcttg    2460
tctgtaagcg gatgccggga gcagacaagc ccgtcagggc gcgtcagcgg gtgttggcgg    2520 gtgtcgggc gcagccatga cccagtcacg tagcgatagc ggagtgatga ccaggtcgaa    2580
ttcgagctcg gtaccgatct aacatttttt cccctatcat ttttccgtct tcatttgtca    2640
ttttttccag aaaaaatcgc gtcattcgac tcatgtctaa tccaacacgt gtctctcggc    2700
ttatcccctg acaccgcccg ccgacagccc gcatgggacg attctatcaa ttcagccgcg    2760
gagtctagtt ttatattgca gaatgcgaga ttgctggttt attataacaa tataagtttt    2820
cattattttc aaaagggggg atttattgtg ggtttaggta agaaattgtc tgttgctgtc    2880
gccgcttcct ttatgagttt aaccatcagt ctgccgggtg ttcaggccgc tgaggatatc    2940
aataaccaaa aagcatacaa agaaacgtac ggcgtctctc atattacacg ccatgatatg    3000
ctgcagatcc ctaaacagca gcaaaacgaa aaataccaag tgcctcaatt cgatcaatca    3060
acgattaaaa atattgagtc tgcaaaagga cttgatgtgt ccgacagctg gccgctgcaa    3120
aacgctgacg gaacagtagc agaatacaac ggctatcacg ttgtgtttgc tcttgcggga    3180
agcccgaaag acgctgatga cacatcaatc tacatgtttt atcaaaaggt cggcgacaac    3240
tcaatcgaca gctggaaaaa gcgggccgt gtctttaaag acagcgataa gttcgacgcc    3300
aacgatccga tcctgaaaga tcagacgcaa gaatggtccg gttctgcaac ctttacatct    3360
gacgaaaaaa tccgtttatt ctacactgac tattccggta acattacgg caaacaaagc    3420 ctgacaacag cgcaggtaaa tgtgtcaaaa tctgatgaca cactcaaaat caacggagtg    3480
gaagatcaca aaacgatttt tgacggagac ggaaaaacat atcagaacgt tcagcagttt    3540
atcgatgaag gcaattatac atccgccgac aaccatacgc tgagagaccc tcactacgtt    3600
gaagacaaag gccataaata ccttgtattc gaagccaaca cgggaacaga aaacggatac    3660
caaggcgaag aatcttttat taacaaagcg tactacggcg gcggcacgaa cttcttccgt    3720
aaagaaagcc agaagcttca gcagagcgct aaaaaacgcg atgctgagtt agcgaacggc    3780
gccctcggta tcatagagtt aaataatgat tacacattga aaaagtaat gaagccgctg    3840 atcacttcaa acacggtaac tgatgaaatc gagcgcgcga atgttttcaa aatgaacggc    3900
aaatggtact tgttcactga ttcacgcggt tcaaaaatga cgatcgatgg tattaactca    3960
aacgatattt acatgcttgg ttatgtatca aactctttaa ccggcccta caagccgctg    4020 aacaaaacag ggcttgtgct gcaaatgggt cttgatccaa acgatgtgac attcacttac    4080
tctcacttcg cagtgccgca agccaaaggc aacaatgtgg ttatcacaag ctacatgaca    4140
aacagaggct tcttcgagga taaaaaggca acatttggcc caagcttctt aatcaacatc    4200
aaaggcaata aacatccgt tgtcaaaaac agcatcctgg agcaaggaca gctgacagtc    4260
aactaataac agcgacatcg atgtctactg gcttaactat gcggcatcag agcagattgt    4320
actgagagtg caccaaaatt aaaaatgaag ttttaaatca atctaaagta tatatgagta    4380
aacttggtct gacagttacc aatgcttaat cagtgaggca cctatctcag cgatctgtct    4440
atttcgttca tccatagttg cctgactccc cgtcgtgtag ataactacga tacgggaggg    4500
cttaccatct ggccccagtg ctgcaatgat accgcgagac ccacgctcac cggctccaga    4560
tttatcagca ataaaccagc cagccggaag ggccgagcgc agaagtggtc ctgcaacttt    4620
```

```
atccgcctcc atccagtcta ttaattgttg ccgggaagct agagtaagta gttcgccagt    4680
taatagtttg cgcaacgttg ttgccattgc tgcaggcatc gtggtgtcac gctcgtcgtt    4740
tggtatggct tcattcagct ccggttccca acgatcaagg cgagttacat gatcccccat    4800
gttgtgcaaa aaagcggtta gctccttcgg tcctccgatc gttgtcagaa gtaagttggc    4860
cgcagtgtta tcactcatgg ttatggcagc actgcataat tctcttactg tcatgccatc    4920
cgtaagatgc ttttctgtga ctggtgagta ctcaaccaag tcattctgag aatagtgtat    4980
gcggcgaccg agttgctctt gcccggcgtc aacacgggat aataccgcgc cacatagcag    5040
aactttaaaa gtgctcatca ttggaaaacg ttcttcgggg cgaaaactct caaggatctt    5100
accgctgttg agatccagtt cgatgtaacc cactcgtgca cccaactgat cttcagcatc    5160
ttttactttc accagcgttt ctgggtgagc aaaaacagga aggcaaaatg ccgcaaaaaa    5220
gggaataagg gcgacacgga aatgttgaat actcatactc ttcctttttc aatattattg    5280
aagcatttat cagggttatt gtctcatgag cggatacata tttgaatgta tttagaaaaa    5340
taaacaaata ggggttccgc gcacatttcc ccgaaaagtg ccacctgcag atcttgaccg    5400
gttgaaataa gtcggtatgg gctggattgc tcatagggat cgctcctgcg aaggttgaag    5460
gtaaaggaga cgtcagttta ccagatcgat tttgaccaga atccgtgtgg cccggttttg    5520
cgtgctgtaa ttccaggcag acaagccgcg ttggtcagcc tgttgccgtt cggcgatacc    5580
gcctatttct atccattcgc cgagcctggc ccgcaccgag gtatgcgcgc tttggctgtc    5640
gatgcggccg ccatggcgga agcgttcggc caggagcg atgtcgagca tgacttcatc    5700
gttggcttgc aggcgcggaa tcaccgcaaa gccggtgctg gcttgctgaa attgcgtgcc    5760
gctggtgaca ccggggtaac cgaaacccga atcgtaaatc gtgacatact cgtaaggccg    5820
gagctggccg atttctattc gtgccggctg gccttccaag gtacgtaact gttgcatcgc    5880
gcgctgctct ccgcgtcgc gggtatcgcc aaccatgccc tgcatccgga tcgcgttggg    5940
gtaaaccgcg atggcggctt cggcattcaa ttgttcggcc gttttatagc tgctttgcaa    6000
cacgaaaatg agcagattgc gctgaggttt atcgagttgc tggattaact ggccaatctc    6060
ttgcaggcgg gccgggctgg ctttgacgat caaatcaaag ccgttaccgg tgacgacttc    6120
gttggcttcc aacaatggca tcaacaaagg ctggatttcg gcggcagggc ggtttcgtaa    6180
tggaatcatc tccatcaccg tttcttgcgc ggcaacgacc tgcagccaaa acaggctaaa    6240
gccggcgaca agcccgtca gcgctagttt gcggtaatgg cgccaagccg gcttggcttg    6300
ccgtcgcatt gtgccgtgcg caacccatcg atcaagccag gcctgtgaac gacgaatgga    6360
gcctttagat ttcacgatat aacgccagat actgattggc gctgttttcc caggaaaaat    6420
ccttgcgcat cgcgttgcgc tgcagctctt gccagagctt gggattggcg tgcaccacca    6480
gcgcgcgctt gatggtttcc agtaacgcgc ccggtacggc atcgttgaag acgaatccgc    6540
tcacgcgtac tagtgatcaa gggatggggtt tcgctactgg cgaacaggat ttttttcatg    6600
tttcaaatct tacatttttca ggatgatgcc ggccaagggc ggcagggtca cggtaacgga    6660
atggttcata ttcatccagg gcaatggctc tgaatgcacg taaccattgc cgatgttgct    6720
gccatcgtaa tattcggagt ccgagttgaa gatttcatga taaacgcctt cgcgcggcac    6780
gccaatgcga tagttctcgc gtggaaccgg cgtgaagttc agtatcacga tcaagtcctc    6840
gttggcggat ttacgccgat agctgatgat cgattgctga tagtcatggc aatcgatcca    6900
ttcgaaaccg tgatgatcga aatcgaattg atacagggcc gaatgagtgg cgtagagttt    6960
gttcaggtcc ttgaccaggg tttgcacgcc gcgatgatgg ggataatcga gcacatacca    7020
```

-continued

```
gtccagatcg cggttcacac tccattcggt gccctgggcg aattcgcagc ccatgaacag    7080
cagtttcttg ccggggtaag tgaacatcaa ggtgtacagc aggcgcagat tggcgaaacg    7140
ctgccattcg tcgcccggca ttttgtttaa tagggattgt ttgccgtgca cgacttcgtc    7200
atgcgaaaac ggcagtacga aattctcggt gaaggcatac agcagaccga aggtcaacga    7260
gtcgtggtga taggaacgat ggatgggttg ttcctgcatg taatgcagaa tgtcgtgcat    7320
ccagcccatg ttccatttca tcgagaatcc caggccgccg gtccaggtcg gccgggtgac    7380
ttgcggccag gaggtcgatt cttccgccat gatcacggtg ccgggatgtt gttcgtgggt    7440
gacggtgttc atgtggcgca ggaagtcgat ggcttccagg ttttcgttgc cgccgtacat    7500
gttcggaatc cattcgttgg cttcgcgcga gtagtccaga tacagcatcg aggccaccgc    7560
gtcgacgcgc aagccgtcca gatggaattc ttccagccag aagt                     7604
```

<210> SEQ ID NO 15
<211> LENGTH: 1434
<212> TYPE: DNA
<213> ORGANISM: Methylomonas sp. 16a
<220> FEATURE:
<221> NAME/KEY: CDS
<222> LOCATION: (1)..(1434)

<400> SEQUENCE: 15

```
atg aaa aaa atc ctg ttc gcc agt agc gaa acc cat ccc ttg atc aaa      48
Met Lys Lys Ile Leu Phe Ala Ser Ser Glu Thr His Pro Leu Ile Lys
1               5                   10                  15 acc ggc ggg ctg gcc gat gtc gcc ggc agc ctg ccg att gcg ctg acc      96
Thr Gly Gly Leu Ala Asp Val Ala Gly Ser Leu Pro Ile Ala Leu Thr
            20                  25                  30 agc cta gac cag gac gtg cgc gtc atc atg ccc cat tat caa ggc atc     144
Ser Leu Asp Gln Asp Val Arg Val Ile Met Pro His Tyr Gln Gly Ile
        35                  40                  45 aaa aac tgc gag ccc ggt cgt tat ttg tgc acg gtg cgg gtc aac aat     192
Lys Asn Cys Glu Pro Gly Arg Tyr Leu Cys Thr Val Arg Val Asn Asn
    50                  55                  60 tgc gac gtc aac ctg ctg gaa acg cat tta ccg gaa agc gat gtc atc     240
Cys Asp Val Asn Leu Leu Glu Thr His Leu Pro Glu Ser Asp Val Ile
65                  70                  75                  80 gtt tgg ctg gtc gat tat ccg ccg ttc ttc aat cat cca ggc aat cca     288
Val Trp Leu Val Asp Tyr Pro Pro Phe Phe Asn His Pro Gly Asn Pro
                85                  90                  95 tac cat gat gaa aac ggc acg ccc tgg ccc gac atc ggc gac cgt ttc     336
Tyr His Asp Glu Asn Gly Thr Pro Trp Pro Asp Ile Gly Asp Arg Phe
            100                 105                 110 gcg ctg ttt tgc cgc atc gtg gtc gaa gta gcg atg aac cgg gcc tac     384
Ala Leu Phe Cys Arg Ile Val Val Glu Val Ala Met Asn Arg Ala Tyr
        115                 120                 125 ttg gac tgg aaa ccg gac gtc gtg cat tgc aac gac tgg caa acc ggc     432
Leu Asp Trp Lys Pro Asp Val Val His Cys Asn Asp Trp Gln Thr Gly
    130                 135                 140 ctg gtc cct gct ctg ctg tca ttg gaa gag cat agg ccg gcc acg gtg     480
Leu Val Pro Ala Leu Leu Ser Leu Glu Glu His Arg Pro Ala Thr Val
145                 150                 155                 160 ttt acg ata cat aac atg gct tac cag ggt gtc ttt ccc agc aat gcc     528
Phe Thr Ile His Asn Met Ala Tyr Gln Gly Val Phe Pro Ser Asn Ala
                165                 170                 175 tac act ttg ctg aat ctg cct ggc cag ctc tgg cat ccg gac ggt ctg     576
Tyr Thr Leu Leu Asn Leu Pro Gly Gln Leu Trp His Pro Asp Gly Leu
            180                 185                 190
```

```
gaa tac cat ggc atg ctg tcc ttc atc aag ggc ggc ttg agc tat tcc      624
Glu Tyr His Gly Met Leu Ser Phe Ile Lys Gly Gly Leu Ser Tyr Ser
            195                 200                 205 gac tgg atc acc acc gtc agc ccg acc tat gcc cag gaa atc cag acc      672
Asp Trp Ile Thr Thr Val Ser Pro Thr Tyr Ala Gln Glu Ile Gln Thr
210                 215                 220 ccg gaa ttc ggt tac ggc ctg gaa ggc ttg ttg gcc cac cgg cag ccg      720
Pro Glu Phe Gly Tyr Gly Leu Glu Gly Leu Leu Ala His Arg Gln Pro
225                 230                 235                 240 acc ttg tcc ggc atc atc aac ggg att gac acc aaa gtc tgg aat ccg      768
Thr Leu Ser Gly Ile Ile Asn Gly Ile Asp Thr Lys Val Trp Asn Pro
            245                 250                 255 gaa acc gac ccc ttc atc gcg caa act tac agc ggc aag act ctc ggc      816
Glu Thr Asp Pro Phe Ile Ala Gln Thr Tyr Ser Gly Lys Thr Leu Gly
            260                 265                 270 aaa aaa gtg ctg aac aaa acc gca ttg cag gcg cgt ttg gga tta ccg      864
Lys Lys Val Leu Asn Lys Thr Ala Leu Gln Ala Arg Leu Gly Leu Pro
            275                 280                 285 gtc aac gcg gat ttg ccg ctg ttg ggc ttg atc ggc cga ctg gtc gat      912
Val Asn Ala Asp Leu Pro Leu Leu Gly Leu Ile Gly Arg Leu Val Asp
290                 295                 300 cag aaa ggc ata gac ctg gtg ctg ggc tgc ttg aag gaa ttg gtc aac      960
Gln Lys Gly Ile Asp Leu Val Leu Gly Cys Leu Lys Glu Leu Val Asn
305                 310                 315                 320 atg ccc ttg cag ttc gcc ttg ctc ggc agc ggc gac aac agc ata cag     1008
Met Pro Leu Gln Phe Ala Leu Leu Gly Ser Gly Asp Asn Ser Ile Gln
            325                 330                 335 gtg cgt ttg cag gat ttc gcc cgc ctg tat ccg gag aag gtt tcg gtg     1056
Val Arg Leu Gln Asp Phe Ala Arg Leu Tyr Pro Glu Lys Val Ser Val
            340                 345                 350 acc atc ggg tac gac gaa aat ctg gcc cac caa atc gaa gcc ggc tcc     1104
Thr Ile Gly Tyr Asp Glu Asn Leu Ala His Gln Ile Glu Ala Gly Ser
            355                 360                 365 gac ctg ttt ctg atg ccg tcg cgc ttc gaa ccc tgc ggc ttg aac cag     1152
Asp Leu Phe Leu Met Pro Ser Arg Phe Glu Pro Cys Gly Leu Asn Gln
370                 375                 380 atg tat agc cag cgt tac ggt acc ctg ccc gtc gtc aga aaa acc ggc     1200
Met Tyr Ser Gln Arg Tyr Gly Thr Leu Pro Val Val Arg Lys Thr Gly
385                 390                 395                 400 ggt ctg gcc gac acc gtg gta gac aca ttg ccc gac acg atc aaa aac     1248
Gly Leu Ala Asp Thr Val Val Asp Thr Leu Pro Asp Thr Ile Lys Asn
            405                 410                 415 ggc acc gcg agc gga ttc gtc ttc aac gat gcc gta ccg ggc gcg tta     1296
Gly Thr Ala Ser Gly Phe Val Phe Asn Asp Ala Val Pro Gly Ala Leu
            420                 425                 430 ctg gaa acc atc aag cgc gcg ctg gtg gtg cac gcc aat ccc aag ctc     1344
Leu Glu Thr Ile Lys Arg Ala Leu Val Val His Ala Asn Pro Lys Leu
            435                 440                 445 tgg caa gag ctg cag cgc aac gcg atg cgc aag gat ttt tcc tgg gaa     1392
Trp Gln Glu Leu Gln Arg Asn Ala Met Arg Lys Asp Phe Ser Trp Glu
            450                 455                 460 aac agc gcc aat cag tat ctg gcg tta tat cgt gaa atc taa             1434
Asn Ser Ala Asn Gln Tyr Leu Ala Leu Tyr Arg Glu Ile
465                 470                 475

<210> SEQ ID NO 16
<211> LENGTH: 477
<212> TYPE: PRT
<213> ORGANISM: Methylomonas sp. 16a
```

<400> SEQUENCE: 16

```
Met Lys Lys Ile Leu Phe Ala Ser Ser Glu Thr His Pro Leu Ile Lys
1               5                   10                  15
Thr Gly Gly Leu Ala Asp Val Ala Gly Ser Leu Pro Ile Ala Leu Thr
            20                  25                  30
Ser Leu Asp Gln Asp Val Arg Val Ile Met Pro His Tyr Gln Gly Ile
        35                  40                  45
Lys Asn Cys Glu Pro Gly Arg Tyr Leu Cys Thr Val Arg Val Asn Asn
    50                  55                  60
Cys Asp Val Asn Leu Leu Glu Thr His Leu Pro Glu Ser Asp Val Ile
65                  70                  75                  80
Val Trp Leu Val Asp Tyr Pro Pro Phe Phe Asn His Pro Gly Asn Pro
                85                  90                  95
Tyr His Asp Glu Asn Gly Thr Pro Trp Pro Asp Ile Gly Asp Arg Phe
            100                 105                 110
Ala Leu Phe Cys Arg Ile Val Val Glu Val Ala Met Asn Arg Ala Tyr
        115                 120                 125
Leu Asp Trp Lys Pro Asp Val Val His Cys Asn Asp Trp Gln Thr Gly
    130                 135                 140
Leu Val Pro Ala Leu Leu Ser Leu Glu Glu His Arg Pro Ala Thr Val
145                 150                 155                 160
Phe Thr Ile His Asn Met Ala Tyr Gln Gly Val Phe Pro Ser Asn Ala
                165                 170                 175
Tyr Thr Leu Leu Asn Leu Pro Gly Gln Leu Trp His Pro Asp Gly Leu
            180                 185                 190
Glu Tyr His Gly Met Leu Ser Phe Ile Lys Gly Gly Leu Ser Tyr Ser
        195                 200                 205
Asp Trp Ile Thr Thr Val Ser Pro Thr Tyr Ala Gln Glu Ile Gln Thr
    210                 215                 220
Pro Glu Phe Gly Tyr Gly Leu Glu Gly Leu Leu Ala His Arg Gln Pro
225                 230                 235                 240
Thr Leu Ser Gly Ile Ile Asn Gly Ile Asp Thr Lys Val Trp Asn Pro
                245                 250                 255
Glu Thr Asp Pro Phe Ile Ala Gln Thr Tyr Ser Gly Lys Thr Leu Gly
            260                 265                 270
Lys Lys Val Leu Asn Lys Thr Ala Leu Gln Ala Arg Leu Gly Leu Pro
        275                 280                 285
Val Asn Ala Asp Leu Pro Leu Leu Gly Leu Ile Gly Arg Leu Val Asp
    290                 295                 300
Gln Lys Gly Ile Asp Leu Val Leu Gly Cys Leu Lys Glu Leu Val Asn
305                 310                 315                 320
Met Pro Leu Gln Phe Ala Leu Leu Gly Ser Gly Asp Asn Ser Ile Gln
                325                 330                 335
Val Arg Leu Gln Asp Phe Ala Arg Leu Tyr Pro Glu Lys Val Ser Val
            340                 345                 350
Thr Ile Gly Tyr Asp Glu Asn Leu Ala His Gln Ile Glu Ala Gly Ser
        355                 360                 365
Asp Leu Phe Leu Met Pro Ser Arg Phe Glu Pro Cys Gly Leu Asn Gln
    370                 375                 380
Met Tyr Ser Gln Arg Tyr Gly Thr Leu Pro Val Val Arg Lys Thr Gly
385                 390                 395                 400
Gly Leu Ala Asp Thr Val Val Asp Thr Leu Pro Asp Thr Ile Lys Asn
                405                 410                 415
```

```
Gly Thr Ala Ser Gly Phe Val Phe Asn Asp Ala Val Pro Gly Ala Leu
            420                 425                 430

Leu Glu Thr Ile Lys Arg Ala Leu Val Val His Ala Asn Pro Lys Leu
        435                 440                 445

Trp Gln Glu Leu Gln Arg Asn Ala Met Arg Lys Asp Phe Ser Trp Glu
    450                 455                 460

Asn Ser Ala Asn Gln Tyr Leu Ala Leu Tyr Arg Glu Ile
465                 470                 475

<210> SEQ ID NO 17
<211> LENGTH: 1431
<212> TYPE: DNA
<213> ORGANISM: Escherichia coli
<220> FEATURE:
<221> NAME/KEY: CDS
<222> LOCATION: (1)..(1431)

<400> SEQUENCE: 17
```

| | | | | | | | | | | | | | | | | |
|---|---|---|---|---|---|---|---|---|---|---|---|---|---|---|---|---|
| atg | cag | gtt | tta | cat | gta | tgt | tca | gag | atg | ttc | ccg | ctg | ctt | aaa | acc | 48 |
| Met | Gln | Val | Leu | His | Val | Cys | Ser | Glu | Met | Phe | Pro | Leu | Leu | Lys | Thr | |
| 1 | | | | 5 | | | | | 10 | | | | | 15 | | |
| ggc | ggt | ctg | gct | gat | gtt | att | ggg | gca | tta | ccc | gca | gca | caa | atc | gca | 96 |
| Gly | Gly | Leu | Ala | Asp | Val | Ile | Gly | Ala | Leu | Pro | Ala | Ala | Gln | Ile | Ala | |
| | | | 20 | | | | | 25 | | | | | 30 | | | |
| gac | ggc | gtt | gac | gct | cgc | gta | ctg | ttg | cct | gca | ttt | ccc | gat | att | cgc | 144 |
| Asp | Gly | Val | Asp | Ala | Arg | Val | Leu | Leu | Pro | Ala | Phe | Pro | Asp | Ile | Arg | |
| | | 35 | | | | | 40 | | | | | 45 | | | | |
| cgt | ggc | gtg | acc | gat | gcg | cag | gta | gta | tcc | cgt | cgt | gat | acc | ttc | gcc | 192 |
| Arg | Gly | Val | Thr | Asp | Ala | Gln | Val | Val | Ser | Arg | Arg | Asp | Thr | Phe | Ala | |
| | 50 | | | | | 55 | | | | | 60 | | | | | |
| ggg | cat | atc | acg | ctg | ttg | ttc | ggt | cat | tac | aac | ggg | gtt | ggc | ata | tac | 240 |
| Gly | His | Ile | Thr | Leu | Leu | Phe | Gly | His | Tyr | Asn | Gly | Val | Gly | Ile | Tyr | |
| 65 | | | | | 70 | | | | | 75 | | | | | 80 | |
| ctg | att | gac | gcg | ccg | cat | ctc | tat | gat | cgt | ccg | gga | agc | ccg | tat | cac | 288 |
| Leu | Ile | Asp | Ala | Pro | His | Leu | Tyr | Asp | Arg | Pro | Gly | Ser | Pro | Tyr | His | |
| | | | | 85 | | | | | 90 | | | | | 95 | | |
| gat | acc | aac | tta | ttt | gcc | tat | acc | gac | aac | gta | ttg | cgt | ttt | gcg | ctg | 336 |
| Asp | Thr | Asn | Leu | Phe | Ala | Tyr | Thr | Asp | Asn | Val | Leu | Arg | Phe | Ala | Leu | |
| | | | 100 | | | | | 105 | | | | | 110 | | | |
| ctg | ggg | tgg | gtt | ggg | gca | gaa | atg | gcc | agc | ggg | ctt | gac | cca | ttc | tgg | 384 |
| Leu | Gly | Trp | Val | Gly | Ala | Glu | Met | Ala | Ser | Gly | Leu | Asp | Pro | Phe | Trp | |
| | | 115 | | | | | 120 | | | | | 125 | | | | |
| cgt | cct | gat | gtg | gtg | cat | gcg | cac | gac | tgg | cat | gca | ggc | ctt | gcg | cct | 432 |
| Arg | Pro | Asp | Val | Val | His | Ala | His | Asp | Trp | His | Ala | Gly | Leu | Ala | Pro | |
| | 130 | | | | | 135 | | | | | 140 | | | | | |
| gcg | tat | ctg | gcg | gcg | cgc | ggg | cgt | ccg | gcg | aag | tcg | gtg | ttt | act | gtg | 480 |
| Ala | Tyr | Leu | Ala | Ala | Arg | Gly | Arg | Pro | Ala | Lys | Ser | Val | Phe | Thr | Val | |
| 145 | | | | | 150 | | | | | 155 | | | | | 160 | |
| cac | aac | ctg | gcc | tat | caa | ggc | atg | ttt | tat | gca | cat | cac | atg | aat | gac | 528 |
| His | Asn | Leu | Ala | Tyr | Gln | Gly | Met | Phe | Tyr | Ala | His | His | Met | Asn | Asp | |
| | | | | 165 | | | | | 170 | | | | | 175 | | |
| atc | caa | ttg | cca | tgg | tca | ttc | ttt | aat | att | cat | ggg | ctg | gaa | ttc | aac | 576 |
| Ile | Gln | Leu | Pro | Trp | Ser | Phe | Phe | Asn | Ile | His | Gly | Leu | Glu | Phe | Asn | |
| | | | 180 | | | | | 185 | | | | | 190 | | | |
| gga | caa | atc | tct | ttc | ctg | aag | gcc | ggt | ctg | tac | tat | gcc | gat | cac | att | 624 |
| Gly | Gln | Ile | Ser | Phe | Leu | Lys | Ala | Gly | Leu | Tyr | Tyr | Ala | Asp | His | Ile | |
| | | 195 | | | | | 200 | | | | | 205 | | | | |
| acg | gcg | gtc | agt | cca | acc | tac | gct | cgc | gag | atc | acc | gaa | ccg | cag | ttt | 672 |
| Thr | Ala | Val | Ser | Pro | Thr | Tyr | Ala | Arg | Glu | Ile | Thr | Glu | Pro | Gln | Phe | |
| | 210 | | | | | 215 | | | | | 220 | | | | | |

| | | | |
|---|---|---|---|
| gcc tac ggt atg gaa ggt ttg ttg caa cag cgt cat cgt gaa ggg cgt<br>Ala Tyr Gly Met Glu Gly Leu Leu Gln Gln Arg His Arg Glu Gly Arg<br>225            230                235              240 | 720 |
| ctt tcc ggc gta ctg aac ggc gtg gac gag aaa atc tgg agt cca gag<br>Leu Ser Gly Val Leu Asn Gly Val Asp Glu Lys Ile Trp Ser Pro Glu<br>               245               250              255 | 768 |
| acg gac tta cta ttg gcc tcg cgt tac acc cgc gat acg ttg gaa gat<br>Thr Asp Leu Leu Leu Ala Ser Arg Tyr Thr Arg Asp Thr Leu Glu Asp<br>260            265               270 | 816 |
| aaa gcg gaa aat aag cgc cag tta caa atc gca atg ggg ctt aag gtt<br>Lys Ala Glu Asn Lys Arg Gln Leu Gln Ile Ala Met Gly Leu Lys Val<br>          275               280              285 | 864 |
| gac gat aaa gtg ccg ctt ttt gca gtg gtg agc cgt ctg acc agc cag<br>Asp Asp Lys Val Pro Leu Phe Ala Val Val Ser Arg Leu Thr Ser Gln<br>290            295               300 | 912 |
| aaa ggc ctc gac ctg gtg ctg gag gcc tta ccg ggt ctt ctg gag cag<br>Lys Gly Leu Asp Leu Val Leu Glu Ala Leu Pro Gly Leu Leu Glu Gln<br>305            310               315              320 | 960 |
| ggc ggg cag ctg gcg cta ctc ggc gcg ggc gat ccg gtg ctg cag gaa<br>Gly Gly Gln Leu Ala Leu Leu Gly Ala Gly Asp Pro Val Leu Gln Glu<br>                      325               330              335 | 1008 |
| ggt ttc ctt gcg gcg gca gcg gaa tac ccc ggc cag gtg ggc gtt cag<br>Gly Phe Leu Ala Ala Ala Ala Glu Tyr Pro Gly Gln Val Gly Val Gln<br>                    340               345              350 | 1056 |
| att ggc tat cac gaa gca ttt tcg cat cgc att atg ggc ggt gcg gac<br>Ile Gly Tyr His Glu Ala Phe Ser His Arg Ile Met Gly Gly Ala Asp<br>               355              360              365 | 1104 |
| gtc att ctg gtg ccc agc cgt ttt gaa ccg tgc ggc tta acg caa ctt<br>Val Ile Leu Val Pro Ser Arg Phe Glu Pro Cys Gly Leu Thr Gln Leu<br>370            375               380 | 1152 |
| tat gga ttg aag tac ggt acg ctg ccg tta gtg cgg cgc acc ggt ggg<br>Tyr Gly Leu Lys Tyr Gly Thr Leu Pro Leu Val Arg Arg Thr Gly Gly<br>385            390               395              400 | 1200 |
| ctt gct gat acg gtt tct gac tgt tct ctt gag aac ctt gca gat ggc<br>Leu Ala Asp Thr Val Ser Asp Cys Ser Leu Glu Asn Leu Ala Asp Gly<br>                    405               410              415 | 1248 |
| gtc gcc agt ggg ttt gtc ttt gaa gat agt aat gcc tgg tcg ctg tta<br>Val Ala Ser Gly Phe Val Phe Glu Asp Ser Asn Ala Trp Ser Leu Leu<br>                    420               425              430 | 1296 |
| cgg gct att cga cgt gct ttt gta ctg tgg tcc cgt cct tct ctg tgg<br>Arg Ala Ile Arg Arg Ala Phe Val Leu Trp Ser Arg Pro Ser Leu Trp<br>               435              440              445 | 1344 |
| cgg ttt gtg caa cgt cag gct atg gca atg gat ttt agc tgg cag gtc<br>Arg Phe Val Gln Arg Gln Ala Met Ala Met Asp Phe Ser Trp Gln Val<br>450            455               460 | 1392 |
| gcg gcg aag tcg tac cgt gag ctt tac tat cgc ttg aaa<br>Ala Ala Lys Ser Tyr Arg Glu Leu Tyr Tyr Arg Leu Lys<br>465            470               475 | 1431 |

<210> SEQ ID NO 18
<211> LENGTH: 477
<212> TYPE: PRT
<213> ORGANISM: Escherichia coli

<400> SEQUENCE: 18

Met Gln Val Leu His Val Cys Ser Glu Met Phe Pro Leu Leu Lys Thr
1               5                    10                 15

Gly Gly Leu Ala Asp Val Ile Gly Ala Leu Pro Ala Ala Gln Ile Ala
                  20                  25                  30

```
Asp Gly Val Asp Ala Arg Val Leu Leu Pro Ala Phe Pro Asp Ile Arg
        35                  40                  45

Arg Gly Val Thr Asp Ala Gln Val Val Ser Arg Arg Asp Thr Phe Ala
        50                  55                  60

Gly His Ile Thr Leu Leu Phe Gly His Tyr Asn Gly Val Gly Ile Tyr
65                  70                  75                  80

Leu Ile Asp Ala Pro His Leu Tyr Asp Arg Pro Gly Ser Pro Tyr His
                85                  90                  95

Asp Thr Asn Leu Phe Ala Tyr Thr Asp Asn Val Leu Arg Phe Ala Leu
            100                 105                 110

Leu Gly Trp Val Gly Ala Glu Met Ala Ser Gly Leu Asp Pro Phe Trp
        115                 120                 125

Arg Pro Asp Val Val His Ala His Asp Trp His Ala Gly Leu Ala Pro
        130                 135                 140

Ala Tyr Leu Ala Ala Arg Gly Arg Pro Ala Lys Ser Val Phe Thr Val
145                 150                 155                 160

His Asn Leu Ala Tyr Gln Gly Met Phe Tyr Ala His His Met Asn Asp
                165                 170                 175

Ile Gln Leu Pro Trp Ser Phe Phe Asn Ile His Gly Leu Glu Phe Asn
            180                 185                 190

Gly Gln Ile Ser Phe Leu Lys Ala Gly Leu Tyr Tyr Ala Asp His Ile
        195                 200                 205

Thr Ala Val Ser Pro Thr Tyr Ala Arg Glu Ile Thr Glu Pro Gln Phe
210                 215                 220

Ala Tyr Gly Met Glu Gly Leu Leu Gln Gln Arg His Arg Glu Gly Arg
225                 230                 235                 240

Leu Ser Gly Val Leu Asn Gly Val Asp Glu Lys Ile Trp Ser Pro Glu
                245                 250                 255

Thr Asp Leu Leu Leu Ala Ser Arg Tyr Thr Arg Asp Thr Leu Glu Asp
            260                 265                 270

Lys Ala Glu Asn Lys Arg Gln Leu Gln Ile Ala Met Gly Leu Lys Val
        275                 280                 285

Asp Asp Lys Val Pro Leu Phe Ala Val Val Ser Arg Leu Thr Ser Gln
290                 295                 300

Lys Gly Leu Asp Leu Val Leu Glu Ala Leu Pro Gly Leu Leu Glu Gln
305                 310                 315                 320

Gly Gly Gln Leu Ala Leu Leu Gly Ala Gly Asp Pro Val Leu Gln Glu
                325                 330                 335

Gly Phe Leu Ala Ala Ala Glu Tyr Pro Gly Gln Val Gly Val Gln
            340                 345                 350

Ile Gly Tyr His Glu Ala Phe Ser His Arg Ile Met Gly Gly Ala Asp
        355                 360                 365

Val Ile Leu Val Pro Ser Arg Phe Glu Pro Cys Gly Leu Thr Gln Leu
370                 375                 380

Tyr Gly Leu Lys Tyr Gly Thr Leu Pro Leu Val Arg Arg Thr Gly Gly
385                 390                 395                 400

Leu Ala Asp Thr Val Ser Asp Cys Ser Leu Glu Asn Leu Ala Asp Gly
                405                 410                 415

Val Ala Ser Gly Phe Val Phe Glu Asp Ser Asn Ala Trp Ser Leu Leu
            420                 425                 430

Arg Ala Ile Arg Arg Ala Phe Val Leu Trp Ser Arg Pro Ser Leu Trp
        435                 440                 445
```

```
Arg Phe Val Gln Arg Gln Ala Met Ala Met Asp Phe Ser Trp Gln Val
    450                 455                 460

Ala Ala Lys Ser Tyr Arg Glu Leu Tyr Tyr Arg Leu Lys
465                 470                 475

<210> SEQ ID NO 19
<211> LENGTH: 1057
<212> TYPE: DNA
<213> ORGANISM: artificial sequence
<220> FEATURE:
<223> OTHER INFORMATION: E. coli glgA deletion fragment #1

<400> SEQUENCE: 19
agatctatcc gccaggttat cgtaggtttt atgcaactga taatgcggc ttaaaatgtc      60
ctgaatggtc gaggaaacca ggaagtattc ctgacgcagg cgcagctcac gcccggagta    120
ggtggagtca tccggataca gtacgcgaga tacgttctcg gagtggtttt tatcttccac    180
tgccgcgaag tagtcaccct ggttgaattt accgaggtta atttcgctac tggcttgcgc    240
actccacaaa cgcagcgtgt tggtcgcgtc ggtgtcgtaa ccaggggatta tctgatcgta    300
agcgactccc agaatctctt cggtttcaat ccagcgcgtt ttttaccctt cctgctgaat    360
gcgaccacca aaacggactt tatagcgcgt gttgtggcgt ttgaattccc acgggttacc    420
atattccagc cagtagtcag gcgactcttt ctggctaccg ttaacgatgt tctgcttgaa    480
cataccgtag tcatagcgga tgccgtaacc gcgccccggc aaccctaacg tcgccagaga    540
atcgaggaag caagccgcca gacgtccag gccaccgtta ccgaggcccg ggtcattttc    600
ttcatcaatc agctcttcga gatttaaccc catcgcttcc agtgcgccct gtacatcttc    660
gtaaattcct agcgacaaca tggcgttgga gagcgtacgg ccaatcaaaa actccatcga    720
caggtagtaa acctgacgag tttcttgcga caactgggca cggtttgaac gtaaccagcg    780
ctccacgaga cgatcgcgca cagcaaataa cgttgcgttc agccattcat gtttattggc    840
gacgaccggg tccttttccaa tcgtaaacat cagcttgtaa gcgatagagt gcttaagagc    900
ttctacgcta agcgtgggcg atgaatatgt aaacggagca ttcatatagg cgtttcctga    960
aaactatttc aagcgatagt aaagctcacg gtacgacttc gccgcgacct gccagctaaa   1020
atccattgcc atagcctgac ggcggccgca ttctaga                             1057

<210> SEQ ID NO 20
<211> LENGTH: 952
<212> TYPE: DNA
<213> ORGANISM: artificial sequence
<220> FEATURE:
<223> OTHER INFORMATION: E. coli glgA deletion fragment #2

<400> SEQUENCE: 20
gcggccgcta agcagcggga acatctctga acatacatgt aaaacctgca ttatcgctcc     60
tgtttatgcc ctaacttccg tagcatttcg cgcgttacca gcacgatgcc ttcttctgaa    120
cgatagaaac gacgtgcatc ttcctctgcg ttttcaccaa tcaccatgcc ttccggaata    180
acacaagcac gatcgatgac gcagcggcgc agacggcacg agcgacctac ccatacttcc    240
ggtaacaata cggcggaatc aatgttgcag aatgaattca gcgaacgcg cgagaacaga    300
acggactgca ccaccaccga accggagatc acacaaccgc cggaaaccag tgagttaagg    360
gtcatcccgt ggctaccgga gcgatcctgc acgaatttcg ctggcggtaa tgattcattg    420
taggtgcgaa ttggccaatt gcgatcgtac atatccagtt ccggcaccac agaggccaga    480
tcgaggttcg ctttccagta agcttccagc gtacccacat cgcgccagta cggctcggca    540
```

```
tccggatcgg attgtacgca agagagcggg aacgggtgcg cataggccag accggcttcg      600
gtgatcttgg gaatcaaatc tttgccaaag tcgtggctgg agttctcatc gcgatcgtct      660
tcttccagca gttcatacag atagtcggcg tcaaagacgt agatacccat actcgccaga      720
gatttgctcg gatcgttcgg cattgacggc gggttagcag gttttttcaac gaattcgata     780 attttatcgt tctcatcaac cgccataacg ccaaatgcgg aggcttcttc aatcggtact      840
ggcatacaag caacggtgca acgtgcgcct ttttcgacgt gatcgataag catacgcgag      900
tagtcttgct tgtagatatg gtcgcccgcc aggatcacca cgtatttcta ga              952
```

```
<210> SEQ ID NO 21
<211> LENGTH: 26
<212> TYPE: DNA
<213> ORGANISM: artificial sequence
<220> FEATURE:
<223> OTHER INFORMATION: Primer

<400> SEQUENCE: 21
agatctatcc gccaggttat cgtagg                                           26

<210> SEQ ID NO 22
<211> LENGTH: 36
<212> TYPE: DNA
<213> ORGANISM: artificial sequence
<220> FEATURE:
<223> OTHER INFORMATION: Primer

<400> SEQUENCE: 22
tctagaatgc ggccgccgtc aggctatggc aatgga                                36

<210> SEQ ID NO 23
<211> LENGTH: 28
<212> TYPE: DNA
<213> ORGANISM: artificial sequence
<220> FEATURE:
<223> OTHER INFORMATION: Primer

<400> SEQUENCE: 23
gcggccgcta agcagcggga acatctct                                         28

<210> SEQ ID NO 24
<211> LENGTH: 28
<212> TYPE: DNA
<213> ORGANISM: artificial sequence
<220> FEATURE:
<223> OTHER INFORMATION: Primer

<400> SEQUENCE: 24
tctagaaata cgtggtgatc ctggcggg                                         28

<210> SEQ ID NO 25
<211> LENGTH: 7376
<212> TYPE: DNA
<213> ORGANISM: artificial sequence
<220> FEATURE:
<223> OTHER INFORMATION: Plasmid pGP704::sacB::E.coli delta glgA

<400> SEQUENCE: 25
ctagaggtac cgcatgcgat atcgagctct cccgggaatt cgatcgctag tttgttttga      60
ctccatccat tagggcttct aaaacgcctt ctaaggccat gtcagccgtt aagtgttcct      120
gtgtcactga aaattgcttt gagaggctct aagggcttct cagtgcgtta catccctggc      180
ttgttgtcca caaccgttaa accttaaaag ctttaaaagc cttatatatt cttttttttc      240
```

-continued

| | | | | | |
|---|---|---|---|---|---|
| ttataaaact | taaaaccttta | gaggctattt | aagttgctga | tttatattaa | ttttattgtt | 300 |
| caaacatgag | agcttagtac | gtgaaacatg | agagcttagt | acgttagcca | tgagagctta | 360 |
| gtacgttagc | catgagggtt | tagttcgtta | acatgagag | cttagtacgt | taaacatgag | 420 |
| agcttagtac | gtgaaacatg | agagcttagt | acgtactatc | aacaggttga | actgctggat | 480 |
| ccttttttgtc | cggtgttggg | ttgaaggtga | agccggtcgg | ggccgcagcg | ggggccggct | 540 |
| tttcagcctt | gcccccctgc | ttcggccgcc | gtggctccgg | cgtcttgggt | gccggcgcgg | 600 |
| gttccgcagc | cttggcctgc | ggtgcgggca | catcggcggg | cttggccttg | atgtgccgcc | 660 |
| tggcgtgcga | gcgaacgtc | tcgtaggaga | acttgacctt | ccccgtttcc | cgcatgtgct | 720 |
| cccaaatggt | gacgagcgca | tagccggacg | ctaacgccgc | ctcgacatcc | gccctcaccg | 780 |
| ccaggaacgc | aaccgcagcc | tcatcacgcc | ggcgcttctt | ggccgcgcgg | gattcaaccc | 840 |
| actcggccag | ctcgtcggtg | tagctctttg | gcatcgtctc | tcgcctgtcc | cctcagttca | 900 |
| gtaatttcct | gcatttgcct | gtttccagtc | ggtagatatt | ccacaaaaca | gcagggaagc | 960 |
| agcgcttttc | cgctgcataa | ccctgcttcg | gggtcattat | agcgattttt | tcggtatatc | 1020 |
| catccttttt | cgcacgatat | acaggatttt | gccaaaggt | tcgtgtagac | tttccttggt | 1080 |
| gtatccaacg | gcgtcagccg | ggcaggatag | gtgaagtagg | cccacccgcg | agcgggtgtt | 1140 |
| ccttcttcac | tgtcccttat | tcgcacctgg | cggtgctcaa | cgggaatcct | gctctgcgag | 1200 |
| gctggccggc | taccgccggc | gtaacagatg | agggcaagcg | gatggctgat | gaaaccaagc | 1260 |
| caaccaggaa | gggcagccca | cctatcaagg | tgtactgcct | tccagacgaa | cgaagagcga | 1320 |
| ttgaggaaaa | ggcggcggcg | gccggcatga | gcctgtcggc | ctacctgctg | gccgtcggcc | 1380 |
| agggctacaa | aatcacgggc | gtcgtggact | atgagcacgt | ccgcgagctg | gcccgcatca | 1440 |
| atggcgacct | gggccgcctg | gcggcctgc | tgaaactctg | gctcaccgac | gacccgcgca | 1500 |
| cggcgcggtt | cggtgatgcc | acgatcctcg | ccctgctggc | gaagatcgaa | gagaagcagg | 1560 |
| acgagcttgg | caaggtcatg | atgggcgtgg | tccgcccgag | ggcagagcca | tgactttttt | 1620 |
| agccgctaaa | acggcggggg | ggtgcgcgtg | attgccaagc | acgtccccat | gcgctccatc | 1680 |
| aagaagagcg | acttcgcgga | gctggtgaag | tacatcaccg | acgagcaagg | caagaccgag | 1740 |
| cgcctgggtc | acgtgcgcgt | cacgaactgc | gaggcaaaca | ccctgcccgc | tgtcatggcc | 1800 |
| gaggtgatgg | cgacccagca | cggcaacacc | cgttccgagg | ccgacaagac | ctatcacctg | 1860 |
| ctggttagct | tccgcgcggg | agagaagccc | gacgcggaga | cgttgcgcgc | gattgaggac | 1920 |
| cgcatctgcg | ctgggcttgg | cttcgccgag | catcagcgcg | tcagtgccgt | gcatcacgac | 1980 |
| accgacaacc | tgcacatcca | tatcgccatc | aacaagattc | acccgacccg | aaacaccatc | 2040 |
| catgagccgt | atcgggccta | ccgcgccctc | gctgacctct | gcgcgacgct | cgaacgggac | 2100 |
| tacgggcttg | agcgtgacaa | tcacgaaacg | cggcagcgcg | tttccgagaa | ccgcgcgaac | 2160 |
| gacatggagc | ggcacgcggg | cgtggaaagc | ctggtcggct | ggatcctcta | cgccggacgc | 2220 |
| atcgtggccg | gcatcaccgg | cgccacaggt | gcggttgctg | gcgcctatat | cgccgacatc | 2280 |
| accgatgggg | aagatcgggc | tcgccacttc | gggctcatga | gcgcttgttt | cggcgtgggt | 2340 |
| atggtggcag | gccccgtggc | cggggactg | ttgggcgcca | tctccttgct | gcctcgcgcg | 2400 |
| tttcggtgat | gacggtgaaa | acctctgaca | catgcagctc | ccgagacgg | tcacagcttg | 2460 |
| tctgtaagcg | gatgccggga | gcagacaagc | ccgtcagggc | gcgtcagcgg | gtgttggcgg | 2520 |
| gtgtcggggc | gcagccatga | cccagtcacg | tagcgatagc | ggagtgatga | ccaggtcgaa | 2580 |
| ttcgagctcg | gtaccgatct | taacatttt | cccctatcat | ttttccgtct | tcatttgtca | 2640 |

-continued

```
tttttttccag aaaaaatcgc gtcattcgac tcatgtctaa tccaacacgt gtctctcggc    2700
ttatcccctg acaccgcccg ccgacagccc gcatgggacg attctatcaa ttcagccgcg    2760
gagtctagtt ttatattgca gaatgcgaga ttgctggttt attataacaa tataagtttt    2820
cattattttc aaaagggggg atttattgtg ggtttaggta agaaattgtc tgttgctgtc    2880
gccgcttcct ttatgagttt aaccatcagt ctgccgggtg ttcaggccgc tgaggatatc    2940
aataaccaaa aagcatacaa agaaacgtac ggcgtctctc atattacacg ccatgatatg    3000
ctgcagatcc ctaaacagca gcaaaacgaa aaataccaag tgcctcaatt cgatcaatca    3060
acgattaaaa atattgagtc tgcaaaagga cttgatgtgt ccgacagctg gccgctgcaa    3120
aacgctgacg gaacagtagc agaatacaac ggctatcacg ttgtgtttgc tcttgcggga    3180
agcccgaaag acgctgatga cacatcaatc tacatgtttt atcaaaaggt cggcgacaac    3240
tcaatcgaca gctggaaaaa cgcgggccgt gtctttaaag acagcgataa gttcgacgcc    3300
aacgatccga tcctgaaaga tcagacgcaa gaatggtccg gttctgcaac ctttacatct    3360
gacggaaaaa tccgtttatt ctacactgac tattccggta acattacgg caaacaaagc    3420
ctgacaacag cgcaggtaaa tgtgtcaaaa tctgatgaca cactcaaaat caacggagtg    3480
gaagatcaca aaacgatttt tgacggagac ggaaaaacat atcagaacgt tcagcagttt    3540
atcgatgaag gcaattatac atccgccgac aaccatacgc tgagagaccc tcactacgtt    3600
gaagacaaag gccataaata ccttgtattc gaagccaaca cgggaacaga aaacggatac    3660
caaggcgaag aatctttatt taacaaagcg tactacggcg gcggcacgaa cttcttccgt    3720
aaagaaagcc agaagcttca gcagagcgct aaaaaacgcg atgctgagtt agcgaacggc    3780
gccctcggta tcatagagtt aaataatgat tacacattga aaaagtaat gaagccgctg    3840
atcacttcaa acacggtaac tgatgaaatc gagcgcgcga atgttttcaa aatgaacggc    3900
aaatggtact tgttcactga ttcacgcggt tcaaaaatga cgatcgatgg tattaactca    3960
aacgatattt acatgcttgg ttatgtatca aactctttaa ccggcccctta caagccgctg    4020
aacaaaacag gcttgtgct gcaaatgggt cttgatccaa acgatgtgac attcacttac    4080
tctcacttcg cagtgccgca agccaaaggc aacaatgtgg ttatcacaag ctacatgaca    4140
aacagaggct tcttcgagga taaaaaggca acatttggcc caagcttctt aatcaacatc    4200
aaaggcaata aacatccgt tgtcaaaaac agcatcctgg agcaaggaca gctgacagtc    4260
aactaataac agcgacatcg atgtctactg gcttaactat gcggcatcag agcagattgt    4320
actgagagtg caccaaaatt aaaatgaag ttttaaatca atctaaagta tatatgagta    4380
aacttggtct gacagttacc aatgcttaat cagtgaggca cctatctcag cgatctgtct    4440
atttcgttca tccatagttg cctgactccc cgtcgtgtag ataactacga tacgggaggg    4500
cttaccatct ggccccagtg ctgcaatgat accgcgagac ccacgctcac cggctccaga    4560
tttatcagca ataaaccagc cagccggaag ggccgagcgc agaagtggtc ctgcaacttt    4620
atccgcctcc atccagtcta ttaattgttg ccgggaagct agagtaagta gttcgccagt    4680
taatagtttg cgcaacgttg ttgccattgc tgcaggcatc gtggtgtcac gctcgtcgtt    4740
tggtatggct tcattcagct ccggttccca acgatcaagg cgagttacat gatcccccat    4800
gttgtgcaaa aaagcggtta gctccttcgg tcctccgatc gttgtcagaa gtaagttggc    4860
cgcagtgtta tcactcatgg ttatggcagc actgcataat tctcttactg tcatgccatc    4920
cgtaagatgc ttttctgtga ctggtgagta ctcaaccaag tcattctgag aatagtgtat    4980
gcggcgaccg agttgctctt gcccggcgtc aacacgggat aataccgcgc cacatagcag    5040
```

```
aactttaaaa gtgctcatca ttggaaaacg ttcttcgggg cgaaaactct caaggatctt    5100
accgctgttg agatccagtt cgatgtaacc cactcgtgca cccaactgat cttcagcatc    5160
ttttactttc accagcgttt ctgggtgagc aaaaacagga aggcaaaatg ccgcaaaaaa    5220
gggaataagg gcgacacgga aatgttgaat actcatactc ttccttttc aatattattg     5280
aagcatttat cagggttatt gtctcatgag cggatacata tttgaatgta tttagaaaaa    5340
taaacaaata ggggttccgc gcacatttcc ccgaaaagtg ccacctgcag atctatccgc    5400
caggttatcg taggttttat gcaactgata atggcggctt aaaatgtcct gaatggtcga    5460
ggaaaccagg aagtattcct gacgcaggcg cagctcacgc ccggagtagg tggagtcatc    5520
cggatacagt acgcgagata cgttctcgga gtggttttta tcttccactg ccgcgaagta    5580
gtcaccctgg ttgaatttac cgaggttaat ttcgctactg gcttgcgcac tccacaaacg    5640
cagcgtgttg gtcgcgtcgg tgtcgtaacc agggattatc tgatcgtaag cgactcccag    5700
aatctcttcg gtttcaatcc agcgcgtttt tttaccttcc tgctgaatgc gaccaccaaa    5760
acggacttta tagcgcgtgt tgtggcgttt gaattcccac gggttaccat attccagcca    5820
gtagtcaggc gactctttct ggctaccgtt aacgatgttc tgcttgaaca taccgtagtc    5880
atagcggatg ccgtaaccgc gccccggcaa ccctaacgtc gccagagaat cgaggaagca    5940
agccgccaga cgtcccaggc caccgttacc gaggcccggg tcattttctt catcaatcag    6000
ctcttcgaga tttaaccca tcgcttccag tgcgccctgt acatcttcgt aaattcctag     6060
cgacaacatg gcgttggaga gcgtacggcc aatcaaaaac tccatcgaca ggtagtaaac    6120
ctgacgagtt tcttgcgaca actgggcacg gtttgaacgt aaccagcgct ccacgagacg    6180
atcgcgcaca gcaaataacg ttgcgttcag ccattcatgt ttattggcga cgaccgggtc    6240
ctttccaatc gtaaacatca gcttgtaagc gatagagtgc ttaagagctt ctacgctaag    6300
cgtgggcgat gaatatgtaa acggagcatt catataggcg tttcctgaaa actatttcaa    6360
gcgatagtaa agctcacggt acgacttcgc cgcgacctgc cagctaaaat ccattgccat    6420
agcctgacgg cggccgctaa gcagcgggaa catctctgaa catacatgta aaacctgcat    6480
tatcgctcct gtttatgccc taacttccgt agcatttcgc gcgttaccag cacgatgcct    6540
tcttctgaac gatagaaacg acgtgcatct tcctctgcgt tttcaccaat caccatgcct    6600
tccggaataa cacaagcacg atcgatgacg cagcggcgca gacggcacga gcgacctacc    6660
catacttccg gtaacaatac ggcggaatca atgttgcaga atgaattcac gcgaacgcgc    6720
gagaacagaa cggactgcac caccaccgaa ccggagatca cacaaccgcc ggaaaccagt    6780
gagttaaggg tcatcccgtg gctaccggag cgatcctgca cgaatttcgc tggcggtaat    6840
gattcattgt aggtgcgaat tggccaattg cgatcgtaca tatccagttc cggcaccaca    6900
gaggccagat cgaggttcgc tttccagtaa gcttccagcg tacccacatc gcgccagtac    6960
ggctcggcat ccggatcgga ttgtacgcaa gagagcggga acgggtgcgc ataggccaga    7020
ccggcttcgg tgatcttggg aatcaaatct ttgccaaagt cgtggctgga gttctcatcg    7080
cgatcgtctt cttccagcag ttcatacaga tagtcggcgt caaagacgta gatacccata    7140
ctcgccagag atttgctcgg atcgttcggc attgacggcg ggttagcagg ttttcaacg     7200
aattcgataa tttatcgtt ctcatcaacc gccataacgc caaatgcgga ggcttcttca     7260
atcggtactg gcatacaagc aacggtgcaa cgtgcgcctt tttcgacgtg atcgataagc    7320
atacgcgagt agtcttgctt gtagatatgg tcgcccgcca ggatcaccac gtattt        7376
```

```
<210> SEQ ID NO 26
<211> LENGTH: 1429
<212> TYPE: DNA
<213> ORGANISM: Methylomonas sp. 16a

<400> SEQUENCE: 26
cggtatgctt aacacatgca agtcgaacgc tgaagggtgc ttgcacctgg atgagtggcg        60
gacgggtgag taatgcatag gaatctgcct attagtgggg gataacgtgg ggaaactcac       120
gctaataccg catacgctct acggaggaaa gccggggacc ttcgggcctg gcgctaatag       180
atgagcctat gtcggattag ctagttggtg gggtaaaggc ctaccaaggc gacgatccgt       240
agctggtctg agaggatgat cagccacact gggactgaga cacggcccag actcctacgg       300
gaggcagcag tggggaatat tggacaatgg gcgcaagcct gatccagcaa taccgcgtgt       360
gtgaagaagg cctgagggtt gtaaagcact ttcaatggga aggaacacct atcggttaat       420
acccggtaga ctgacattac ccatacaaga agcaccggct aactccgtgc cagcagccgc       480
ggtaatacgg agggtgcaag cgttaatcgg aattactggg cgtaaagcgt gcgtaggcgg       540 tttttttaagt cagatgtgaa agccctgggc ttaacctggg aactgcattt gatactgggg       600
aactagagtt gagtagagga gagtggaatt tcaggtgtag cggtgaaatg cgtagagatc       660
tgaaggaaca ccagtggcga aggcggctct ctggactcaa actgacgctg aggtacgaaa       720
gcgtgggtag caaacaggat tagataccct ggtagtccac gccgtaaacg atgtcaacta       780
accgttgggt tcttaaagaa cttagtggtg gagctaacgt attaagttga ccgcctgggg       840 agtacgccg caaggctaaa actcaaatga attgacgggg gcccgcacaa gcggtggagc       900
atgtggttta attcgatgca acgcgaagaa ccttacctac ccttgacatc ctcggaactt       960
gtcagagatg acttggtgcc ttcgggaacc gagagacagg tgctgcatgg ctgtcgtcag      1020
ctcgtgtcgt gagatgttgg gttaagtccc gtaacgagcg caacccttat ccttagttgc      1080
cagcgcgtca tggcgggaac tctagggaga ctgccggtga taaaccggag gaaggtgggg      1140
acgacgtcaa gtcatcatgg cccttatggg tagggctaca cacgtgctac aatggtcggt      1200
acagagggtt gcgaactcgc gagagccagc caatcccaaa aagccgatcc tagtccggat      1260
tgcagtctgc aactcgactt gcatgaagtc ggaatcgcta gtaatcgcgg atcagaatgc      1320
cgcggtgaat acgttcccgg gccttgtaca caccgcccgt cacaccatgg gagtgggttg      1380
caaaagaagt aggtagttta accttcggga gggcgcttac cactttgtg               1429
```